(12) United States Patent
Babb et al.

(10) Patent No.: US 11,235,048 B2
(45) Date of Patent: Feb. 1, 2022

(54) STREPTOCOCCAL VACCINE

(71) Applicant: GPN Vaccines Pty Ltd, Yarralumla (AU)

(72) Inventors: Rachelle Babb, Tennyson (AU); Mohammed Alsharifi, Hillbank (AU); Austen Yannis Chen, Belair (AU); Shannon Christa David, Sommerton Park (AU); Timothy Raymond Hirst, Yarralumla (AU); Abiodun David Ogunniyi, Manningham (AU); James Cleland Paton, Parkside (AU)

(73) Assignee: GPN Vaccines Pty Ltd, Yarralumla (AU)

( * ) Notice: Subject to any disclaimer, the term of this patent is extended or adjusted under 35 U.S.C. 154(b) by 0 days.

(21) Appl. No.: 17/001,474

(22) Filed: Aug. 24, 2020

(65) Prior Publication Data

US 2021/0170011 A1 Jun. 10, 2021

Related U.S. Application Data

(63) Continuation of application No. 15/561,910, filed as application No. PCT/AU2016/050231 on Mar. 24, 2016, now Pat. No. 10,821,168.

(30) Foreign Application Priority Data

Mar. 26, 2015 (AU) ................................ 2015901098

(51) Int. Cl.
| | | |
|---|---|---|
| *A61K 39/09* | (2006.01) | |
| *C12N 15/01* | (2006.01) | |
| *C12N 13/00* | (2006.01) | |
| *C12N 1/36* | (2006.01) | |
| *A61P 31/04* | (2006.01) | |
| *A61K 39/00* | (2006.01) | |

(52) U.S. Cl.
CPC ............ *A61K 39/092* (2013.01); *A61P 31/04* (2018.01); *C12N 1/36* (2013.01); *C12N 13/00* (2013.01); *C12N 15/01* (2013.01); *A61K 2039/521* (2013.01); *A61K 2039/523* (2013.01); *A61K 2039/54* (2013.01); *A61K 2039/541* (2013.01); *A61K 2039/543* (2013.01); *A61K 2039/55544* (2013.01); *A61K 2039/58* (2013.01)

(58) Field of Classification Search
None
See application file for complete search history.

(56) References Cited

U.S. PATENT DOCUMENTS 10,821,168 B2 11/2020 Babb et al.
2007/0128215 A1 6/2007 Grisez et al.

FOREIGN PATENT DOCUMENTS

| WO | WO-2012/100302 A1 | 8/2012 | |
|---|---|---|---|
| WO | WO-2012100302 A1 * | 8/2012 | ............. A61K 39/12 |
| WO | WO-2012/145491 A2 | 10/2012 | |
| WO | WO-2012/145491 A3 | 10/2012 | |

OTHER PUBLICATIONS

Babb, R. et al. (May 2016, e-published Feb. 1, 2016). "Intranasal vaccination with γ-irradiated *Streptococcus pneumoniae* whole-cell vaccine provides serotype-independent protection mediated by B-cells and innate IL-17 responses," *Clin Sci* 130(9):697-710.
Berry, A.M. et al. (Feb. 1999). "Comparative virulence of *Streptococcus pneumoniae* strains with insertion-duplication, point, and deletion mutations in the pneumolysin gene," *Infect Immun* 67(2):981-985.
Datta, S.K. et al. (Jul. 2006). "Vaccination with irradiated *Listeria* induces protective T cell immunity," *Immunity* 25(1):143-152.
International Search Report dated Jun. 6, 2016, for PCT Application No. PCT/AU2016/050231, filed Mar. 24, 2016, 6 pages.
Johnson, M. et al. (Oct. 1997). "Murine model of interleukin-8-induced otitis media," *Laryngoscope* 107(10):1405-1408.
Johnston, J.W. et al. (Oct. 2004). "Lipoprotein PsaA in virulence of *Streptococcus pneumoniae*: surface accessibility and role in protection from superoxide," *Infect Immun* 72(10):5858-5867.
Lu, Y.J. et al. (Jun. 2010, e-published Apr. 28, 2010). "Options for inactivation, adjuvant, and route of topical administration of a killed, unencapsulated pneumococcal whole-cell vaccine," *Clin Vaccine Immunol* 17(6):1005-1012.
Malley, R. et al. (Aug. 2001). "Intranasal immunization with killed unencapsulated whole cells prevents colonization and invasive disease by capsulated pneumococci," *Infect Immun* 69(8):4870-4873.
McDaniel, L.S. et al. (Oct. 1998). Comparison of the PspA sequence from *Streptococcus pneumoniae* EF5668 to the previously identified PspA sequence from strain Rx1 and ability of PspA from EF5668 to elicit protection against pneumococci of different capsular types, *Infect Immun* 66(10):4748-4754.
Murray, M. (1939). "The Antigenic Properties of Streptococci Killed by Ultraviolet Light," *Journal of Laboratory and Clinical Medicine* 24:1245-1246.
Ogunniyi, A.D. et al. (Jan. 2007, e-published Nov. 6, 2006). "Development of a vaccine against invasive pneumococcal disease based on combinations of virulence proteins of *Streptococcus pneumonia*," *Infect Immun* 75(1):350-357.
Paterson, G.K. et al. (May 2010, e-published May 30, 2010). "Recent advances in the field of *Salmonella typhi* vaccines," *Hum Vaccin* 6(5):379-384.
Rass, U. et al. (Sep. 21, 2007). "Defective DNA repair and neurodegenerative disease," *Cell* 130(6):991-1004.
Sanakkayala, N. et al. (Dec. 2005). "Induction of antigen-specific Th 1-type immune responses by gamma-irradiated recombinant *Brucella abortus* RB51," *Clin Diagn Lab Immunol* 12(12):1429-1436.

(Continued)

*Primary Examiner* — Brian Gangle
(74) *Attorney, Agent, or Firm* — Mintz Levin Cohn Ferris Glovsky and Popeo, P.C.; Terri Shieh-Newton; David V. Dang

(57) ABSTRACT

The present invention relates to photon-irradiated streptococcal vaccine preparations and methods for their use.

20 Claims, 33 Drawing Sheets

Specification includes a Sequence Listing.

(56) References Cited

OTHER PUBLICATIONS

Thoms, K-M. et al. (Jun. 2007). "Lessons learned from DNA repair defective syndromes," *Exp Dermatol* 16(6):532-544.
Tuasikal, B.J. (2012). "Kandidat vaksin iradiasi *Streptococcus agalactiae* untuk pencegahan mastitis subklinis pada ruminansia [*Streptococcus agalactiae* irradiated vaccine candidate for ubclinical mastitis prevention in ruminants]" Doctoral dissertation, located at <http://repository.ipb.ac.id/handle/123456789/61095> last visited Jun. 2, 2016, 104 pages (Translation of Abstract only).
Written Opinion dated Jun. 6, 2016, for PCT Application No. PCT/AU2016/050231, filed Mar. 24, 2016, 6 pages.
Yother, J. et al. (Apr. 1998). "Generation and properties of a *Streptococcus pneumoniae* mutant which does not require choline or analogs for growth," *J Bacteriol* 180(8):2093-2101.

\* cited by examiner

SEQ ID NO: 7

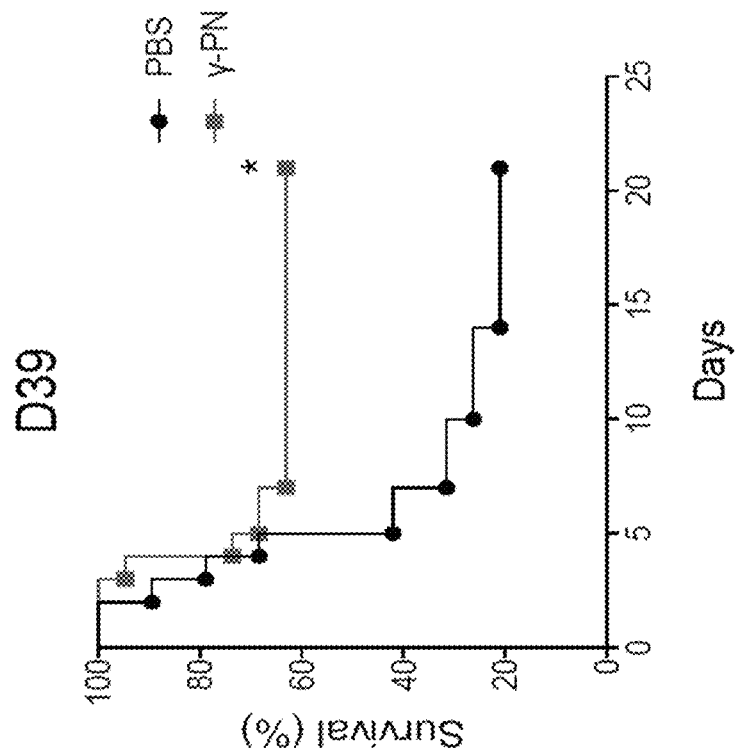
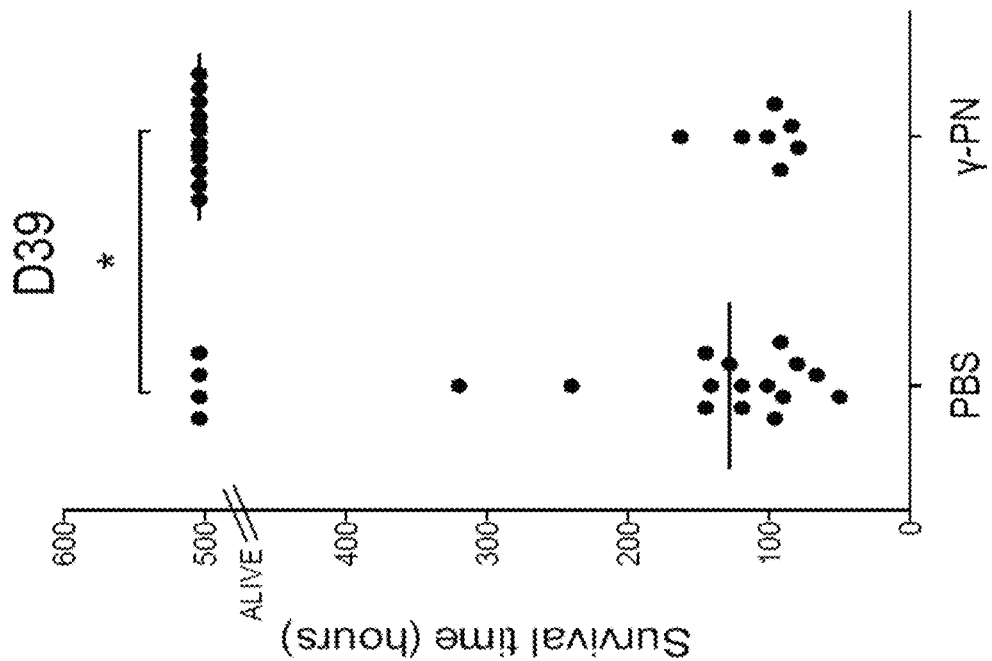
FIG. 7A
FIG. 7B

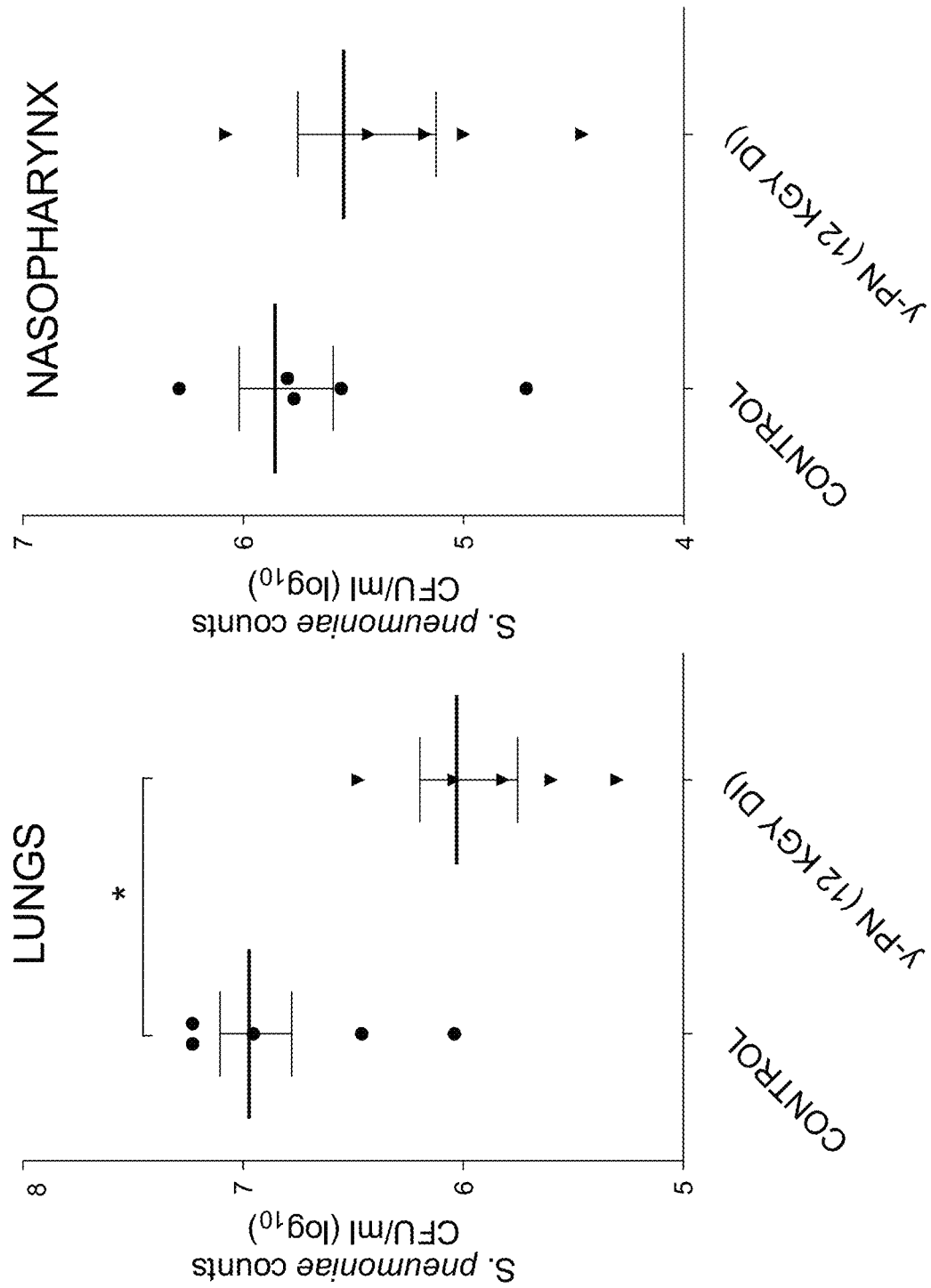

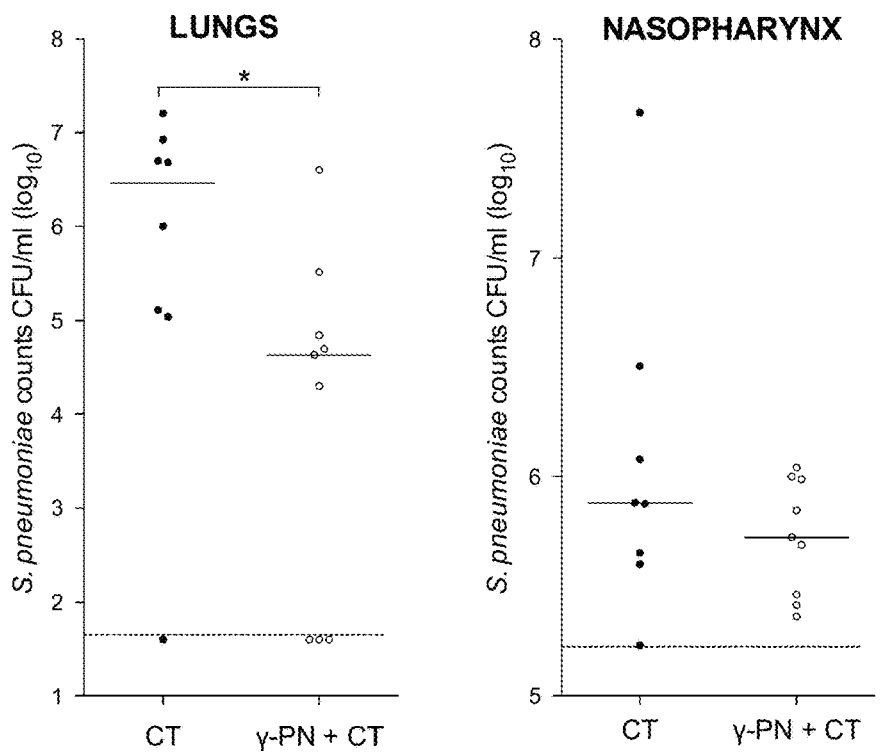
FIG. 14A
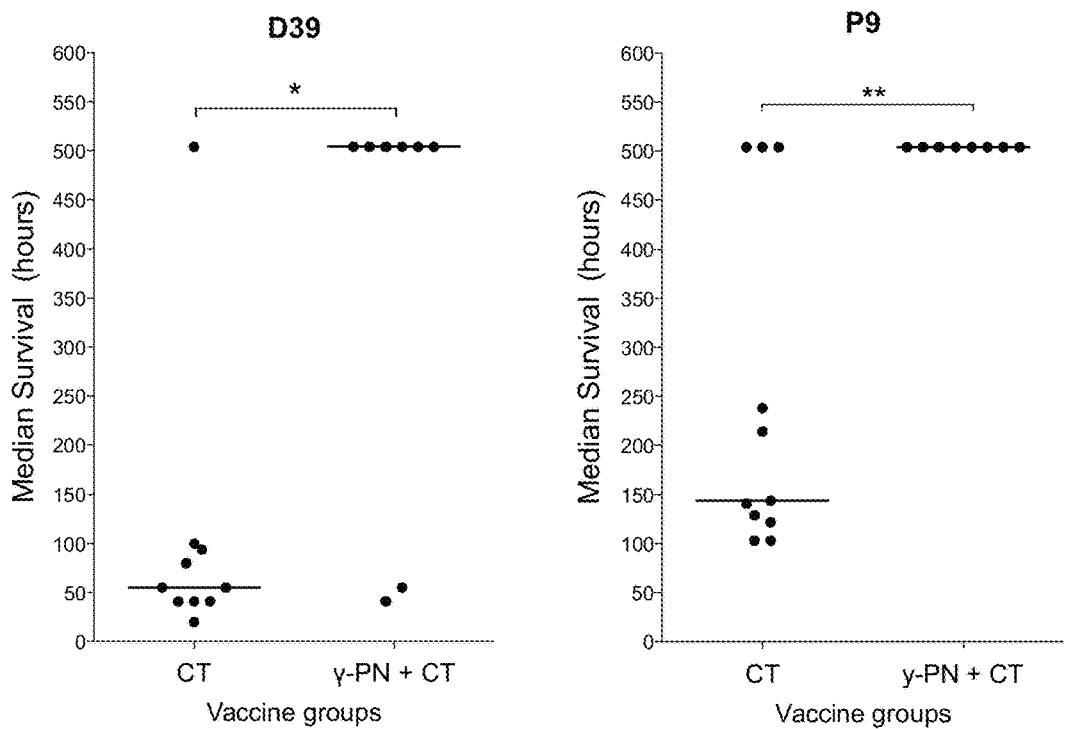
FIG. 14C  FIG. 14D

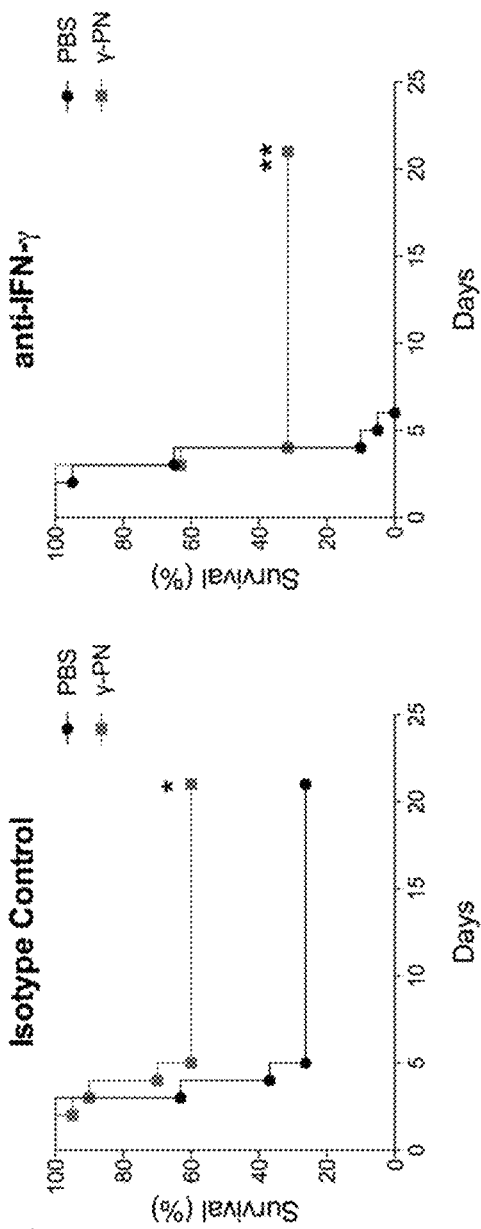
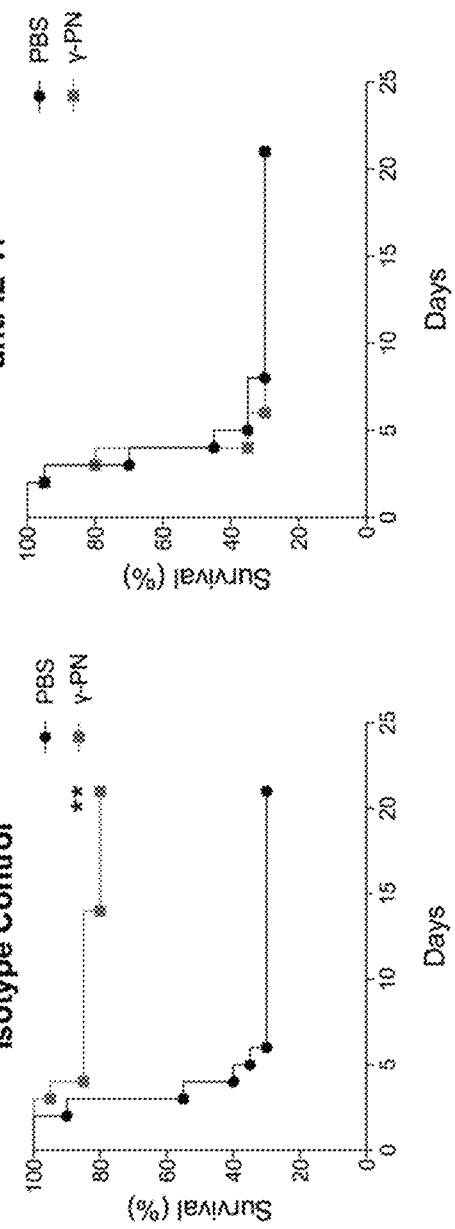
FIG. 17A
FIG. 17B

SEQ ID NO: 8

SEQ ID NO: 1

TGAAAATAGTTAACAGACTTTTGACTTCTTTTATATGATATAATAAAGTATAGTA
                                                    -35
TTTATGAAAAGGACATATAGAGACTGTAAAAATATACTTTTGAAAATCTTTTTAGT
      -10
CTGGGGTGTTATTGTAGATAGAATGCAGACCTGTCAGTCCTATTTACAGTGTCAAAA
TAGTGCGTTTTGAAGTTCTATCTACAAGCCTAATCGTGACTAAGATTGTCTTCTTTGTA
AGGTAGAAATAAGGAGTTTCTGGTTCTGGATTGTAAAAATGAGTTGTTT
                                  *lytA start*
TAATTGATAAGGAGTAGAATATGGAAATTAATGTGAGTAAATTAAGAACAGATTTGCC
TCAAGTCGGCGTGCAACCATATAGGCAAGTACACGCACACTCAACTGGGAATCCGCATT
CAACCGTACAGAATGAAGCGGATTATCACTGGCGGAAAGACCCAGAATTAGGTTTTTTC
TCGCACATTGTTGGGAACGGTTGCATCATGCAGGTAGGACCTGTTGATAATGGTGCCTG
GGACGTTGGGGCGGTTGGAATGCTGAGACCTATGCAGCGGTTGAACTGATTGAAAGCC
ATTCAACCAAAGAAGAGTTCATGACGGACTACCGCCTTTATATCGAACTCTTACGCAAT
CTAGCAGATGAAGCAGGTTTGCCGAAAACGCTTGATACAGGGAGTTTAGCTGGAATTAA
AACGCACGAGTATTGCACGAATAACCAACCAAACAACCACTCAGACCACGTTGACCCTT
ATCCATATCTTGCTAAATGGGGCATTAGCCGTGAGCAGTTTAAGCATGATATTGAGAAC
GGCTTGACGATTGAAACAGGCTGGCAGAAGAATGACACTGGCTACTGGTACGTACATTC
AGACGGCTCTTATCCAAAGACAAGTTTGAGAAAATCAATGGCACTTGGTACTACTTTG
ACAGTTCAGGCTATATGCTTGCAGACCGCTGGAGGAAGCACACAGACGGCAACTGGTAC
TGGTTCGACAACTCAGGCGAAATGGCTACAGGCTGGAAGAAAATCGCTGATAAGTGGTA
CTATTTCAACGAAGAAGGTGCCATGAAGACAGGCTGGGTCAAGTACAAGGACACTTGGT
ACTACTTAGACGCTAAAGAAGGCGCCATGGTATCAAATGCCTTTATCCAGTCAGCGGAC
GGAACAGGCTGGTACTACCTCAAACCAGACGGAACACTGGCAGACAAGCCAGAATTCAC
AGTAGAGCCAGATGGCTTGATTACAGTAAAATAATAATGGAATGTCTTTCAAATCAGA
                                    *lytA stop*
ACAGCGCATATTATTAGGTCTTGAAAAGCTTAATAGTATGCG

SEQ ID NO: 2

TGAAAATAGTTTAACAGACTTTGACTTCTTTTATATGATATAATAAAGTATAGTA
                                    -35
TTTATGAAAAGGACATATAGAGACTGTAAAAATATACTTTTGAAAATCTTTTTAGT
  -10
CTGGGGTGTTATTGTA GATAGA A TGC AGACCTTGTCAGTCCTATTTACAGTGTCAAAA
TAGTGCGTTTTGAAGTTCTATCTACAAGCCTAATCGTGACTAAGATTGTCTTCTTTGTA
AGGTAGAAATAAAGGAGTTTCTGGTTCTGGATTGTAAAAATGAGTTGTTTTAATT GA
TAAGGAGTAGAATTAATGGAATGTCTTTC AAATCAGAACAG**CGCATATTATTAGGTCT
TGAAAAGCTTAATAGTATGCG**

FIG. 24B

SEQ ID NO: 3

5'-A AUGC AGACCUUGUCAGUCCUAUUUACAGUGUCAAAAUAGUGCGUUUUGAAGUUC
UAUCUACAAGCCUAAUCGUGACUAAGAUUGUCUUCUUUGUAAGGUAGAAAUAAAGGAGU
UUCUGGUUCUGGAUUGUAAAAAUGAGUUGUUUUAAUU GAUAAGGAGUAGAAUUAAUG
GAAUGUCUUUC AAAUCAGAACAG**CGCAUAUUAUUAGGUCUUGAAAAGCUUAAUAGUA
UGCG**-3'

SEQ ID NO: 4

CAGTTTTGGGACTCTTTATTGGCTATAGTTTTAATGTTGCGGCAGGTTCTAGTATCGTGC
                                                    -35
TTACAGCTGCTAGTTTCTTTCTCATTAGCTTCTTTATCGCTCCCAAACAACGATATTTGA
                      -10
AACTGAAAAATAAACATTTGTTAAAATAAGGGGCAAAGCCCTAA`TAAATTGG`AGGATCTA
ATGAAAAAATTAGGTACATTACTCGTTCTCTTTCTTTCTGCAATCATTCTTGTAGCATGT
psaA start
GCTAGCGGAAAAAAGATACAACTTCTGGTCAAAAACTAAAAGTTGTTGCTACAAACTCA
ATCATCGCTGATATTACTAAAATATTGCTGGTGACAAAATTGACCTTCATAGTATCGTT
CCGATTGGGCAAGACCCACACGAATACGAACCACTTCCTGAAGACGTTAAGAAACTTCT
GAGGCTGATTGATTTTCTATAACGGTATCAACCTTGAAACAGGTGGCAATGCTTGGTTT
ACAAAATTGGTAGAAAATGCCAAGAAAACTGAAAACAAAGACTACTTCGCAGTCAGCGAC
GGCGTTGATGTTATCTACCTTGAAGGTCAAAATGAAAAAGGAAAAGAAGACCCACACGCT
TGGCTTAACCTTGAAAACGGTATTATTTTTGCTAAAAATATCGCCAAACAATTGAGCGCC
AAAGACCCTAACAATAAAGAATTCTATGAAAAAAATCTCAAAGAATATACTGATAAGTTA
GACAAACTTGATAAAGAAAGTAAGGATAAATTTAATAAGATCCCTGCTGAAAAGAAACTC
ATTGTAACCAGCGAAGGAGCATTCAAATACTTCTCTAAAGCCTATGGTGTTCCAAGTGCC
TACATCTGGGAAATCAATACTGAAGAAGAAGGAACTCCTGAACAAATCAAGACCTTGGTT
GAAAAACTTCGCCAAACAAAAGTTCCATCACTCTTTGTAGAATCAAGTGTGGATGACCGT
CCAATGAAAACTGTTTCTCAAGACACAAACATCCCAATCTACGCACAAATCTTTACTGAC
TCTATCGCAGAACAA`GGTAAAGAAGGCGACA`GCTACTACAGCATGATGAAATACAACCTT
GACAAGATTGCTGAAGGATTGGCAAAATAAGCCTCTGAAAAACGTCATTCTCATGTGAGC
                      psaA stop
TGGCG

SEQ ID NO: 5

CAGTTTTGGACTCTTTATTGGCTATAGTTTAATGTTGCGGCAGGTTCTAGTATCGTGC

-35

TTACAGCTGCTAGTTTCTTTCTCATTAGCTTCTTTATCGCTCCAAACAACGATATTTGA

-10

AACTGAAAATAAACATTTGTTAAAATAAGGGGCAAAGCCCTAATAAATTGGGTAAAGAA

GGCGACAGCTACTACAGCATGATGAAATACAACCTTGACAAGATTGCTGAAGGATTGGCA

AAATAAGCCTCTGAAAACGTCATTCTCATGTGAGCTGGCG psaA stop

FIG. 27B

SEQ ID NO: 6

5'-GGUAAAGAA

GGCGACAGCUACUACAGCAUGAUGAAAUACAACCUUGACAAGAUUGCUGAAGGAUUGGCA

AAAUAAGCCUCUGAAAACGUCAUUCUCAUGUGAGCUGGCG-3' psaA stop

STREPTOCOCCAL VACCINE

INCORPORATION BY CROSS-REFERENCE

This application is a continuation application of U.S. patent application Ser. No. 15/561,910 filed on Sep. 26, 2017, which is the U.S. National Phase of International Application No. PCT/AU2016/050231, filed on Mar. 24, 2016, which designated the United States, and which claims priority from Australian Provisional patent Application No. 2015901098 entitled "Streptococcal Vaccine" filed on Mar. 26, 2015. The disclosures of the above-referenced applications are incorporated herein by reference in their entireties, including any drawings.

SEQUENCE LISTING STATEMENT

The present application contains a Sequence Listing, which is being submitted via EFS-Web on even date herewith. The Sequence Listing is submitted in a file entitled "Sequence Listing_045172-501C01US.txt," which was created on Aug. 24, 2020, and is approximately 8 kb in size. This Sequence Listing is hereby incorporated by reference.

TECHNICAL FIELD

The present invention relates generally to the field of vaccines. More specifically, the present invention relates to streptococcal vaccine preparations and methods for their use.

BACKGROUND

Streptococci are a genus of spheroidal bacteria belonging to the family Streptococcaceae. There are many different species of streptococci, some of which cause disease in humans and animals. Others are important in the manufacture of various fermented products.

Individual streptococcal species are classified into two key groups based on their haemolytic properties (alpha- and beta-haemolytic). Alpha-haemolytic streptococci include *Streptococcus pneumoniae* and *Viridans* streptococci. The beta-haemolytic group is made up of Group A and Group B streptococci. Group B streptococci usually inhabit the digestive system and the vagina of women without adverse effect. Most people quickly develop a natural immunity to Group B streptococci although they can cause more serious types of infection in newborn infants. Group A streptococci commonly inhabit the throat and skin surface, and are a common cause of infection in adults and children. Although most Group A infections do not usually pose a serious threat to health (e.g. throat infections, cellulitis, impetigo, sinusitis, middle ear infections) Group A Streptococci can establish a more serious invasive infection by penetrating deeper into the tissues and organs of the body (e.g. pneumonia, sepsis, meningitis, necrotising fasciitis) and can trigger serious sequelae including acute post-streptococcal glomerulonephritis and acute rheumatic fever.

In addition, Enterococcal (faecal) streptococcal species occur in significant numbers in the bowel and can cause endocarditis and urinary tract infections.

*Streptococcus pneumoniae* (also called pneumococcus) is an important human pathogen accounting for significant morbidity and mortality in human and animal populations. It causes serious conditions including pneumonia, meningitis, sinusitis, and otitis media. An estimated 1.6 million people die globally from invasive pneumococcal disease each year and approximately one million of those are children. There are many different serotypes of *S. pneumoniae* (>90) distinguishable on the basis of capsule chemical structure and immunogenicity. The capsular polysaccharide is considered to be an essential virulence factor of *S. pneumoniae* as non-encapsulated strains are virtually absent among *S. pneumoniae* that are responsible for non-invasive pneumococcal disease. Capsular polysaccharides are thus used as vaccine antigens in current pneumococcal vaccines.

Current pneumococcal conjugate vaccines cover only a selected set of serotypes, (e.g. PCV7 (7 serotypes), PCV10 (10 serotypes) and PCV13 (13 serotypes)). In many populations the introduction of the PCV7 vaccine targeting serotypes 4, 6B, 9V, 14, 18C, 19F, and 23F significantly reduced the burden of pneumococcal disease. However, despite their efficacy against disease caused by targeted vaccine serotypes, serotype replacement often reduces the net effect of vaccination. For example, in a number of locations including the USA, England, Germany, Wales, and The Netherlands, serotype 19A was reported to be a common emerging non-vaccine serotype after PCV7 introduction. The emergence of non-vaccine serotypes upon the implementation of pneumococcal conjugate vaccines thus raises a problem.

In consideration of the emergence of non-vaccine serotypes associated with pneumococcal conjugate vaccines, a need exists for new streptococcal vaccines capable of inducing immunity against a broader range of serotypes.

Colonisation of the upper respiratory tract is the obligatory first step in the pathogenesis of pneumococcal disease, and therefore considered the most important risk factor for invasive pneumococcal disease. It also provides the basis for horizontal spread of pneumococci in the community, making it an important target for preventive measures.

Accordingly, a need exists for vaccines capable of inducing immunity against a broad range of pneumococcal serotypes and which are suited to upper respiratory tract administration.

SUMMARY OF THE INVENTION

The invention relates to an improved streptococcal vaccine that reduces or alleviates at least one deficiency of existing streptococcal vaccines.

Accordingly, the invention relates to at least the following embodiments:

Embodiment 1. A method for preventing or treating an infection by streptococcal bacteria in a subject, the method comprising administering a therapeutically effective amount of photon-irradiated streptococcal bacteria to the subject to thereby prevent or treat the infection.

Embodiment 2. The method according to embodiment 1, wherein the method prevents or treats infection by a plurality of different streptococcal species and/or serotypes.

Embodiment 3. The method according to embodiment 2, wherein the photon-irradiated streptococcal bacteria comprise different: *Streptococcus* species, streptococcal serotypes, and/or streptococcal derivatives.

Embodiment 4. The method according to any one of embodiments 1 to 3, wherein the streptococcal infection comprises infection by one or more serotypes of *Streptococcus pneumoniae*.

Embodiment 5. The method according to any one of embodiments 1 to 4, wherein the infection by streptococcal bacteria is any one or more of a respiratory tract infection, pneumonia, an ear infection, an ear-ache, a middle ear infection, otitis media, sinusitis, meningitis, conjunctivitis, bacteraemia, septicaemia, a joint infection, a bone infection, septic arthritis, sepsis, osteomyelitis, a soft tissue infection, cellulitis, myositis, periorbital cellulitis, an abscess, necrotising fasciitis, impetigo, peritonitis, a cardiac infection, endocarditis, and/or pericarditis.

Embodiment 6. A method of inducing an immune response against streptococcal bacteria in a subject, the method comprising administering a therapeutically effective amount of photon-irradiated streptococcal bacteria to the subject to thereby induce the immune response.

Embodiment 7. The method according to embodiment 6, wherein the immune response comprises a heterotypic immune response against a different streptococcal species and/or serotype to that administered to the subject.

Embodiment 8. The method according to embodiment 6 or embodiment 7, wherein the therapeutically effective amount of photon-irradiated streptococcal bacteria comprise different: *Streptococcus* species, streptococcal serotypes, and/or streptococcal derivatives.

Embodiment 9. The method according to embodiment 7 or embodiment 8, wherein the different streptococcal species and/or serotype is a *Streptococcus pneumoniae* serotype.

Embodiment 10. The method according to any one of embodiments 6 to 9, wherein the immune response comprises any one or more of:
  (i) a B-lymphocyte response;
  (ii) an innate immune response induced at least in part by interaction of double-stranded RNA from the photon-irradiated streptococcal bacteria with Toll-like receptors;
  (iii) a T-lymphocyte response.

Embodiment 11. The method according to any one of embodiments 1 to 10, wherein the photon-irradiated streptococcal bacteria comprise at least one *Streptococcus pneumoniae* serotype, or at least one unencapsulated derivative of a *Streptococcus pneumoniae* serotype.

Embodiment 12. The method according to any one of embodiments 1 to 11, wherein the photon-irradiated streptococcal bacteria comprise mutant streptococcal bacteria comprising:
  (i) one or more defective DNA repair proteins; and/or
  (ii) a genetic alteration causing defective DNA repair capacity.

Embodiment 13. The method according to embodiment 12, wherein the photon-irradiated mutant streptococcal bacteria comprise a defect in at least one gene that encodes a DNA repair protein.

Embodiment 14. The method according to embodiment 13, wherein the photon-irradiated mutant streptococcal bacteria are *Streptococcus pneumoniae* mutants comprising a defect in one or more genes selected from a gene encoding a DNA alkylation repair protein, a gene encoding DNA polymerase 4, hexA, hexB, mutS, radC, recA, recF, recN, recO, uvrA, uvrB, uvrC or uvrD.

Embodiment 15. The method according to any one of embodiments 12 to 14, wherein the defective DNA repair protein is mutated, truncated or absent in the photon-irradiated mutant streptococcal bacteria.

Embodiment 16. The method according to any one of embodiments 12 to 15, wherein the photon-irradiated mutant streptococcal bacteria comprise streptococcal Rx1 strain derivatives in which:
  (i) any one or more of autolysin, hemolysin, pneumolysin, and/or PsaA protein is/are defective; and/or
  (ii) any one or more of autolysin, hemolysin, and/or a PsaA protein is/are absent. Embodiment 17. The method according to embodiment 16, wherein the photon-irradiated streptococcal Rx1 strain derivatives:

(i) comprise any one or more of a gene encoding a defective autolysin protein, a gene encoding defective hemolysin, a gene encoding defective pneumolysin, and/or a gene encoding defective PsaA protein; or
  (ii) are derivatives in which any one or more of a gene encoding autolysin, a gene encoding hemolysin, and/or a gene encoding PsaA protein, is/are absent.

Embodiment 18. The method according to embodiment 16 or embodiment 17, wherein the autolysin is LytA.

Embodiment 19. The method according to any one of embodiments 16 to 18, wherein the photon-irradiated streptococcal Rx1 strain derivatives:
  (i) comprise a gene encoding defective LytA protein, and a gene encoding defective pneumolysin; or
  (ii) do not contain the lytA gene, and comprise a gene encoding a defective pneumolysin.

Embodiment 20. The method according to any one of embodiments 12 to 19, wherein the photon-irradiated mutant streptococcal bacteria require a reduced dosage of photon-irradiation for inactivation compared to that required by corresponding non-mutant streptococcal bacteria.

Embodiment 21. The method according to any one of embodiments 1 to 20, wherein some or all of the photon-irradiated streptococcal bacteria comprise modified streptococcal bacteria comprising a sequence of DNA encoding an RNA transcript, wherein the RNA transcript comprises a region of self-complementarity capable of forming a double-stranded portion after transcription.

Embodiment 22. The method according to embodiment 21, wherein the portion of the double-stranded RNA transcript is at least: 10, 15, 20, 25, 30, 35, 40, 45, 50, 55, 60, 65 or 70 base pairs in length.

Embodiment 23. The method according to embodiment 21 or embodiment 22, wherein the double-stranded RNA transcript initiates an innate immune response in the subject comprising Toll-like receptor activation.

Embodiment 24. The method according to embodiment 23, wherein the Toll-like receptor is Toll-like receptor-3 (TLR-3).

Embodiment 25. The method according to any one of embodiments 1 to 24, wherein the photon-irradiated streptococcal bacteria comprise auxotrophic mutant streptococcal bacteria.

Embodiment 26. The method according to any one of embodiments 1 to 24, wherein the photon-irradiated streptococcal bacteria comprise at least one recombinant DNA portion encoding an antigen or a component thereof that:
  (i) inactivates or attenuates the bacteria; and/or
  (ii) induces or enhances an immune response in the subject.

Embodiment 27. The method according to embodiment 26, wherein the recombinant DNA portion replaces or disrupts an endogenous gene necessary for pathogenicity, infection, multiplication, growth in vivo, or any combination thereof.

Embodiment 28. The method according to any one of embodiments 1 to 27, wherein the photon-irradiated streptococcal bacteria comprise whole killed streptococcal bacteria.

Embodiment 29. The method according to any one of embodiments 1 to 28, wherein the photon-irradiated streptococcal bacteria are administered to the subject mucosally or intranasally.

Embodiment 30. The method according to any one of embodiments 1 to 29, wherein the photon-irradiated streptococcal bacteria are administered to the subject in combination with an adjuvant.

Embodiment 31. The method according to any one of embodiments 1 to 30, wherein one, two or three separate doses of the photon-irradiated streptococcal bacteria are administered to the subject.

Embodiment 32. The method according to any one of embodiments 1 to 31, wherein the subject is a human.

Embodiment 33. The method according to any one of embodiments 1 to 32, wherein the photon-irradiated streptococcal bacteria are administered a total dosage of at least: 8 kilogray (kGy), 9kGy, 10kGy, 11kGy, 12kGy, 15kGy, 20kGy, 25kGy, 30 kGy, 40kGy, or 50 kGy of photon-irradiation.

Embodiment 34. The method according to any one of embodiments 1 to 33, wherein the photon-irradiated streptococcal bacteria comprise gamma-irradiated streptococcal bacteria, X-irradiated streptococcal bacteria, or a combination thereof.

Embodiment 35. The method according to any one of embodiments 1 to 33, wherein the photon-irradiated streptococcal bacteria comprise X-irradiated streptococcal bacteria.

Embodiment 36. The method according to any one of embodiments 1 to 33, wherein the photon-irradiated streptococcal bacteria comprise a combination of gamma-irradiated streptococcal bacteria and X-irradiated streptococcal bacteria.

Embodiment 37. The method according to embodiment 20 or embodiment 33, wherein the photon-irradiation is gamma-irradiation.

Embodiment 38. The method according to embodiment 20 or embodiment 33, wherein the photon-irradiation is X-irradiation.

Embodiment 39. The method according to embodiment 20 or embodiment 33, wherein the photon-irradiation is a combination of gamma-irradiation and X-irradiation.

Embodiment 40. The method according to any one of embodiments 1 to 39, wherein the photon-irradiated streptococcal bacteria comprise streptococcal Rx1 strain derivatives:
(i) comprise a gene encoding a defective LytA protein, a gene encoding defective pneumolysin, and a gene encoding defective PsaA protein;
(ii) comprise a gene encoding a defective LytA protein, a gene encoding defective pneumolysin, and in which a gene encoding PsaA protein is absent;
(iii) comprise a gene encoding a defective PsaA protein, a gene encoding defective pneumolysin, and in which a gene encoding LytA protein is absent; or
(iv) comprise a gene encoding defective pneumolysin, in which a gene encoding LytA protein is absent, and in which a gene encoding PsaA protein is absent.

Embodiment 41. A vaccine composition comprising photon-irradiated streptococcal bacteria and a pharmaceutically-acceptable excipient, diluent and/or carrier, wherein:
(i) the photon-irradiated streptococcal bacteria comprise. mutant streptococcal bacteria comprising one or more defective DNA repair proteins, and/or mutant streptococcal bacteria in which at least one type of DNA repair protein is absent; and/or
(ii) the photon-irradiated streptococcal bacteria comprise modified streptococcal bacteria comprising a sequence of DNA encoding an RNA transcript, wherein the RNA transcript comprises a region of self-complementarity capable of forming a double-stranded portion after transcription.

Embodiment 42. The vaccine composition according to embodiment 41, wherein the mutant streptococcal bacteria are *Streptococcus pneumoniae* mutants comprising a defect in one or more genes selected from. a gene encoding a DNA alkylation repair protein, a gene encoding DNA polymerase 4, hexA, hexB, mutS, radC, recA, recF, recN, recO, uvrA, uvrB, uvrC or uvrD.

Embodiment 43. The vaccine composition according to embodiment 41 or embodiment 42, wherein the modified streptococcal bacteria are modified *Streptococcus pneumoniae* bacteria and the portion of the double-stranded RNA transcript is at least. 10, 15, 20, 25, 30, 35, 40, 45, 50, 55, 60, 65 or 70 base pairs in length.

Embodiment 44. The vaccine composition according to any one of embodiments 41 to 43, wherein the photon-irradiated streptococcal bacteria comprise at least one recombinant DNA portion encoding an antigen or a component thereof that:
(i) inactivates or attenuates the bacteria; or
(ii) induces or enhances an immune response in the subject.

Embodiment 45. The vaccine composition according to embodiment 44, wherein the recombinant DNA portion replaces or disrupts an endogenous gene necessary for pathogenicity, infection, reproduction or any combination thereof.

Embodiment 46. The vaccine according to any one or more of embodiments 41 to 45, wherein the photon-irradiated streptococcal bacteria comprise streptococcal Rx1 strain derivative strains in which:
(i) any one or more of autolysin, hemolysin, pneumolysin, and/or PsaA protein is/are defective; and/or
(ii) any one or more of autolysin, hemolysin, and/or a PsaA protein is/are absent.

Embodiment 47. The vaccine according to embodiment 46, wherein the photon-irradiated streptococcal Rx1 strain derivatives:
(i) comprise any one or more of a gene encoding a defective autolysin protein, a gene encoding defective hemolysin, a gene encoding defective pneumolysin, and/or a gene encoding defective PsaA protein; or
(ii) are derivatives in which any one or more of a gene encoding autolysin, a gene encoding hemolysin, and/or a gene encoding PsaA protein, is/are absent.

Embodiment 48. The vaccine according to any one of embodiments 41 to 47, wherein the photon-irradiated streptococcal Rx1 strain derivatives:
(i) comprise a gene encoding defective LytA protein, and a gene encoding defective pneumolysin; or
(ii) do not contain the lytA gene, and comprise a gene encoding a defective pneumolysin.

Embodiment 49. The vaccine according to any one of embodiments 41 to 48, wherein the photon-irradiated mutant streptococcal bacteria comprise streptococcal Rx1 strain derivatives:
(i) comprise a gene encoding a defective LytA protein, a gene encoding defective pneumolysin, and a gene encoding defective PsaA protein;
(ii) comprise a gene encoding a defective LytA protein, a gene encoding defective pneumolysin, and in which a gene encoding PsaA protein is absent;
(iii) comprise a gene encoding a defective PsaA protein, a gene encoding defective pneumolysin, and in which a gene encoding LytA protein is absent; or
(iv) comprise a gene encoding defective pneumolysin, in which a gene encoding LytA protein is absent, and in which a gene encoding PsaA protein is absent.

Embodiment 50. The vaccine composition according to any one of embodiments 41 to 49, wherein the photon-irradiated streptococcal bacteria comprise whole-attenuated or whole-killed streptococcal bacteria.

Embodiment 51. The vaccine composition according to any one of embodiments 41 to 50, further comprising an adjuvant.

Embodiment 52. The vaccine composition according to any one of embodiments 41 to 51, wherein the vaccine composition is formulated for mucosal or intranasal administration or formulated for injection intramuscularly, subcutaneously or intradermally.

Embodiment 53. The vaccine composition according to any one of embodiments 41 to 52, wherein the photon-irradiated streptococcal bacteria comprise gamma-irradiated mutant streptococcal bacteria and/or gamma-irradiated modified streptococcal bacteria.

Embodiment 54. The vaccine composition according to any one of embodiments 41 to 52, wherein the photon-irradiated streptococcal bacteria comprise X-irradiated mutant streptococcal bacteria and/or X-irradiated modified streptococcal bacteria.

Embodiment 55. The vaccine composition according to any one of embodiments 41 to 52, wherein the photon-irradiated streptococcal bacteria comprise:
(i) a combination of gamma-irradiated and X-irradiated mutant streptococcal bacteria; and/or
(ii) a combination of gamma-irradiated and X-irradiated modified streptococcal bacteria.

Embodiment 56. A method for preparing the vaccine composition according to any one of embodiments 41 to 55, the method comprising:
(i) photon-irradiating a preparation of streptococcal bacteria to thereby attenuate or kill the bacteria; and
(ii) combining the photon-irradiated streptococcal bacteria with a pharmaceutically-acceptable excipient, diluent and/or carrier.

Embodiment 57. The method according to embodiment 56, wherein said photon-irradiating the preparation of streptococcal bacteria comprises exposing the bacteria to gamma-radiation.

Embodiment 58. The method according to embodiment 56, wherein said photon-irradiating the preparation of streptococcal bacteria comprises exposing the bacteria to X-radiation.

Embodiment 59. The method according to embodiment 56, wherein said photon-irradiating the preparation of streptococcal bacteria comprises exposing the bacteria to gamma-radiation and X-radiation.

Embodiment 60. A vaccine composition prepared by the method of any one of embodiments 56 to 59.

Embodiment 61. A vaccine composition according to any one of embodiments 41 to 55 or 60 for use in preventing or treating an infection by streptococcal bacteria.

Embodiment 62. Use of photon-irradiated streptococcal bacteria in the preparation of a medicament for preventing or treating an infection by streptococcal bacteria, wherein the medicament is the vaccine composition according to any one of embodiments 41 to 55 or 60.

Embodiment 63. The vaccine composition according to embodiment 61 or the use according to embodiment 62, wherein the infection by streptococcal bacteria is any one or more of a respiratory tract infection, pneumonia, ear infection, earache, middle ear infection, otitis media, sinusitis, meningitis, conjunctivitis, bacteraemia, septicaemia, a joint infection, a bone infection, septic arthritis, osteomyelitis, a soft tissue infection, cellulitis, myositis, periorbital cellulitis, an abscess, peritonitis, a cardiac infection, endocarditis, and pericarditis.

BRIEF DESCRIPTION OF THE FIGURES

Preferred embodiments of the present invention will now be described, by way of non-limiting example only, with reference to the accompanying figures wherein:

FIG. 7 is a graph showing (A) duration of median survival and (B) percentage survival in mice vaccinated with gamma-irradiated *S. pneumoniae* Rx1 (ΔLytA, PdT) against intranasal challenge with live *Streptococcus pneumoniae* strain D39 (serotype 2). *P=<0.05; γ-PN=gamma-irradiated *S. pneumoniae* Rx1 (ΔLytA, PdT);

FIG. 8 provides a series of graphs indicative of immunity in mice vaccinated with gamma-irradiated *S. pneumoniae* Rx1 (ΔLytA, PdT) against heterotypic challenge with EF3030 (serotype 19F) (FIG. 8A & FIG. 8B) or P9 (serotype 6A) (FIG. 8C). EF3030 bacterial counts were determined 96 hours post challenge in the lungs (FIG. 8A) and nasopharynx (FIG. 8B).

Figure 11:
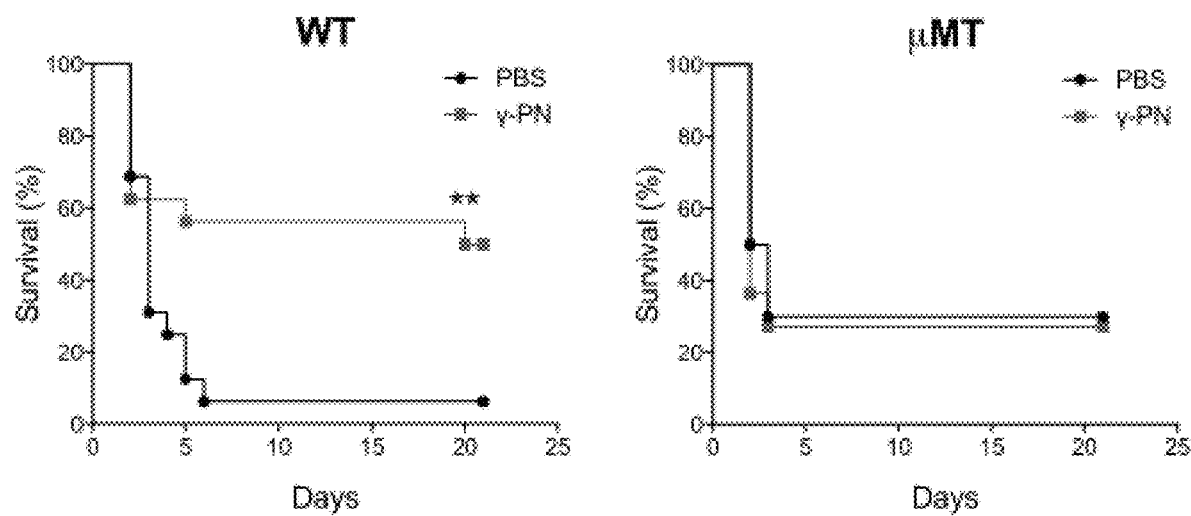
Figures 12A, 12B:
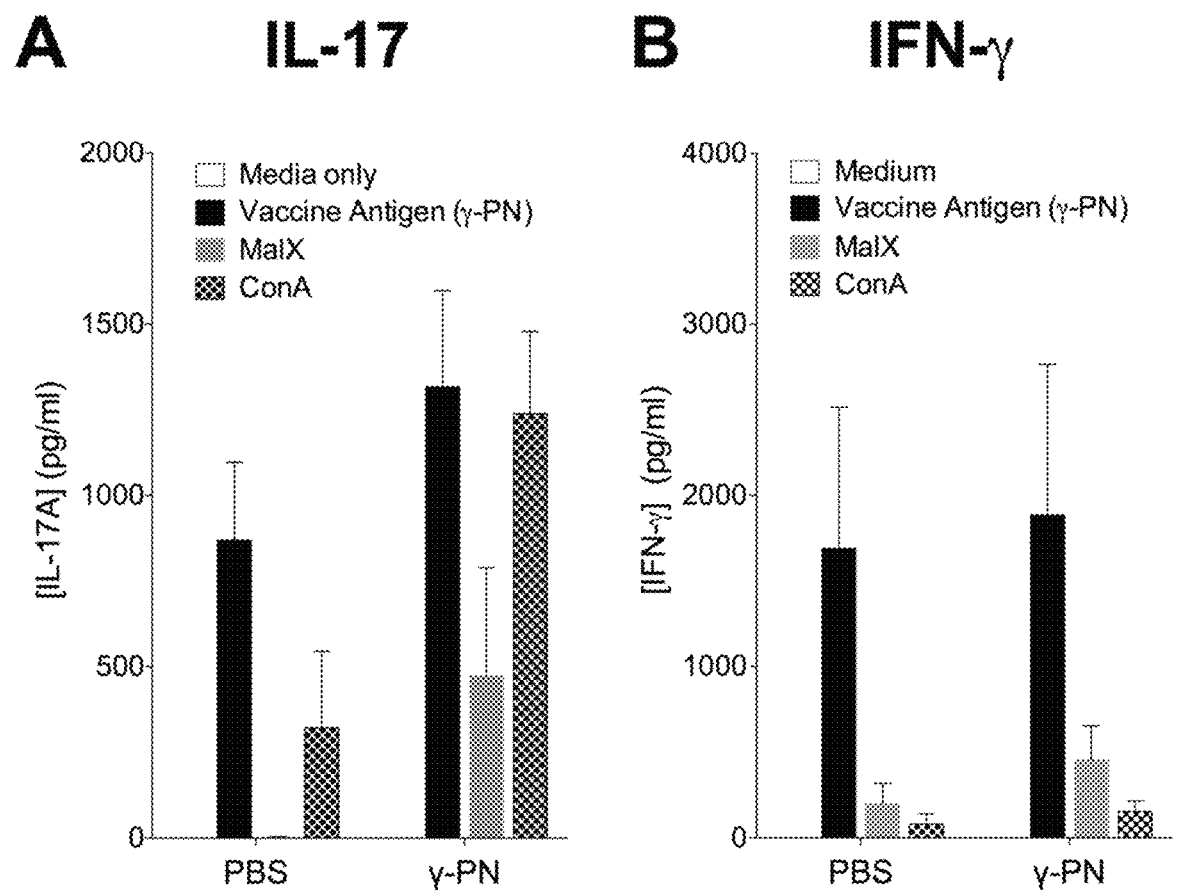
Figure 12C:
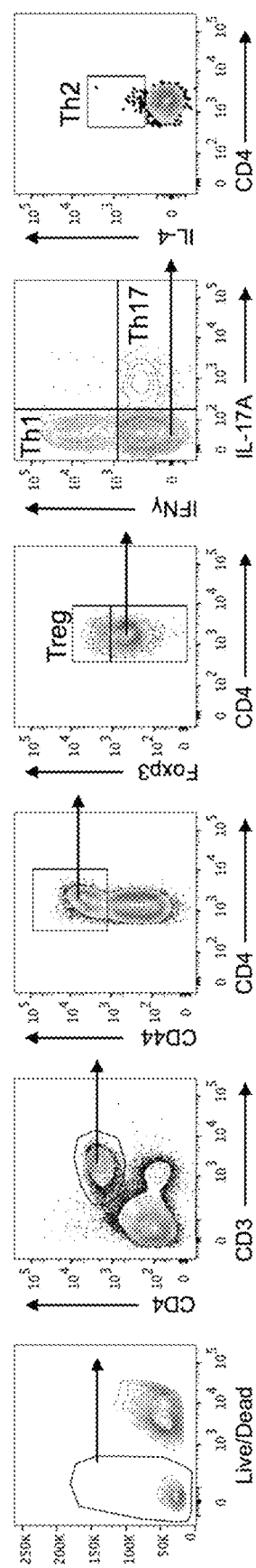
Figure 12D:
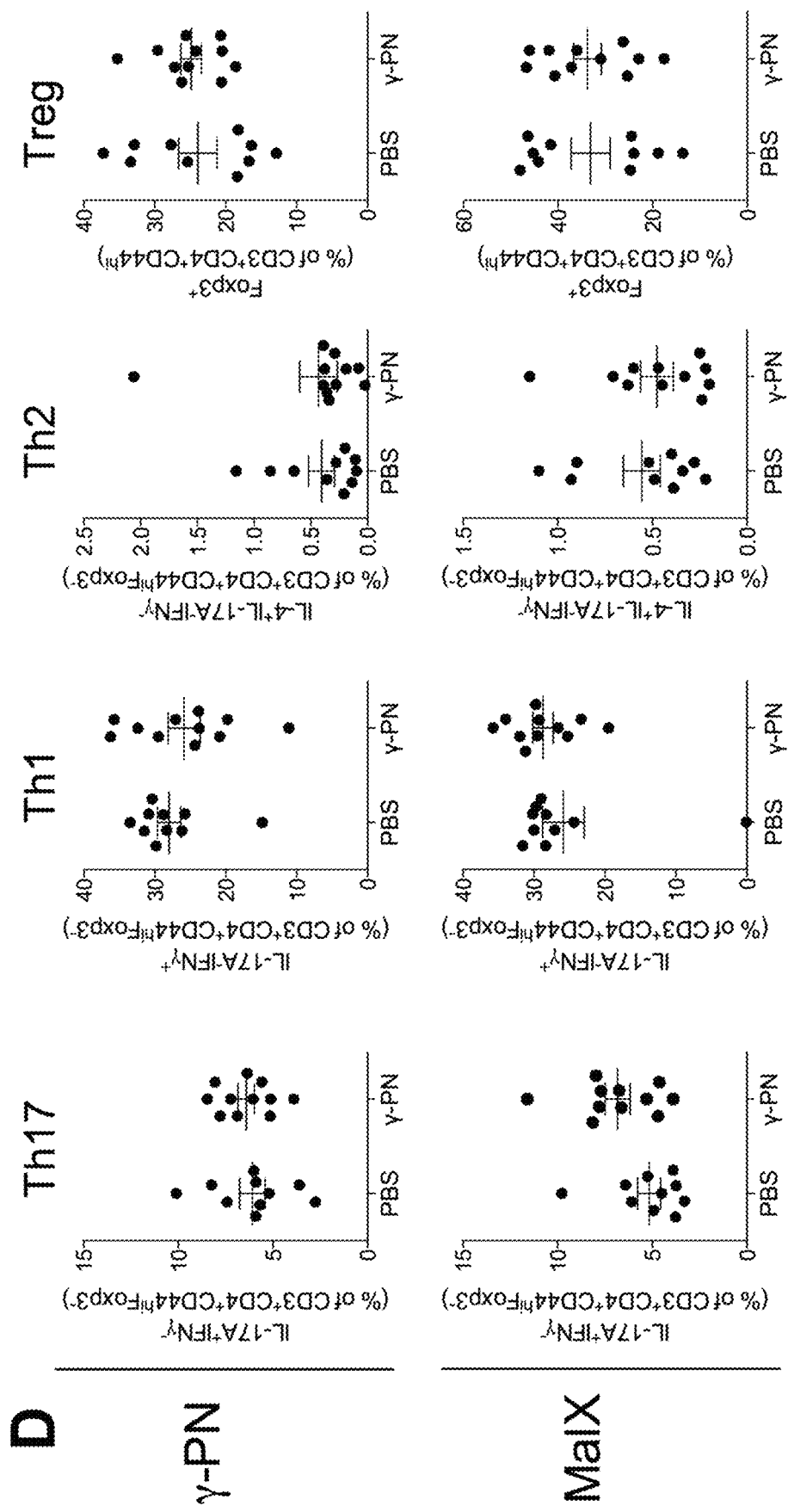
Figures 13A, 13B:
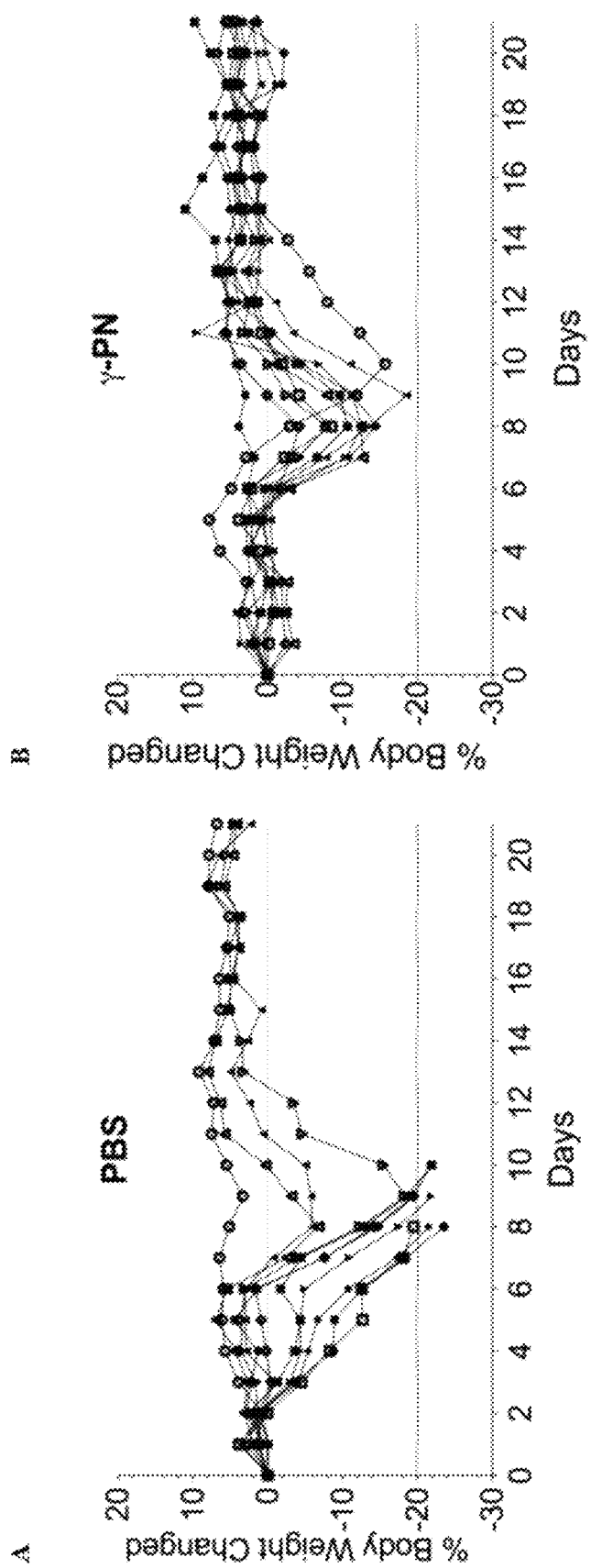
Figure 15A:
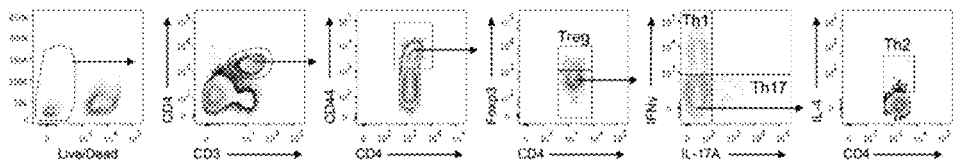
Figure 15B:
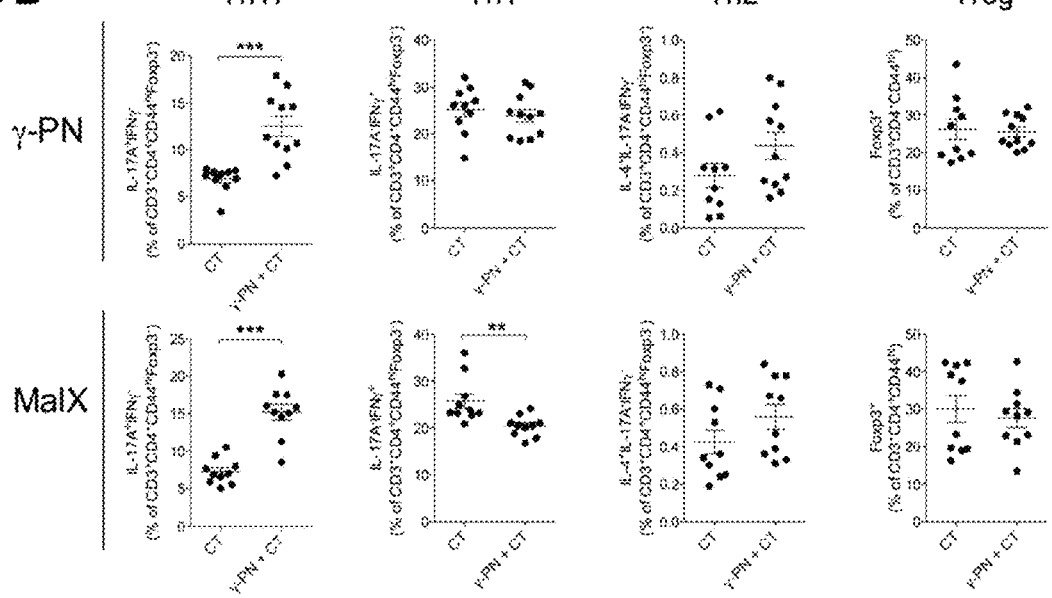
Figure 15C:
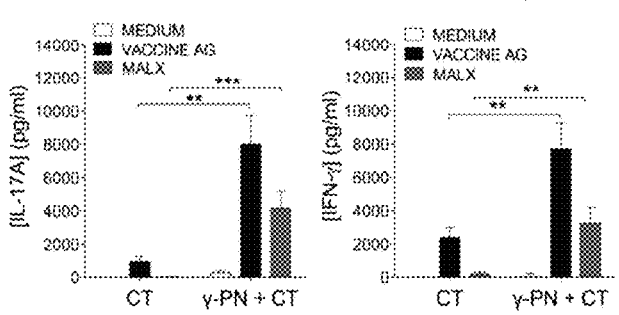
Figure 16:
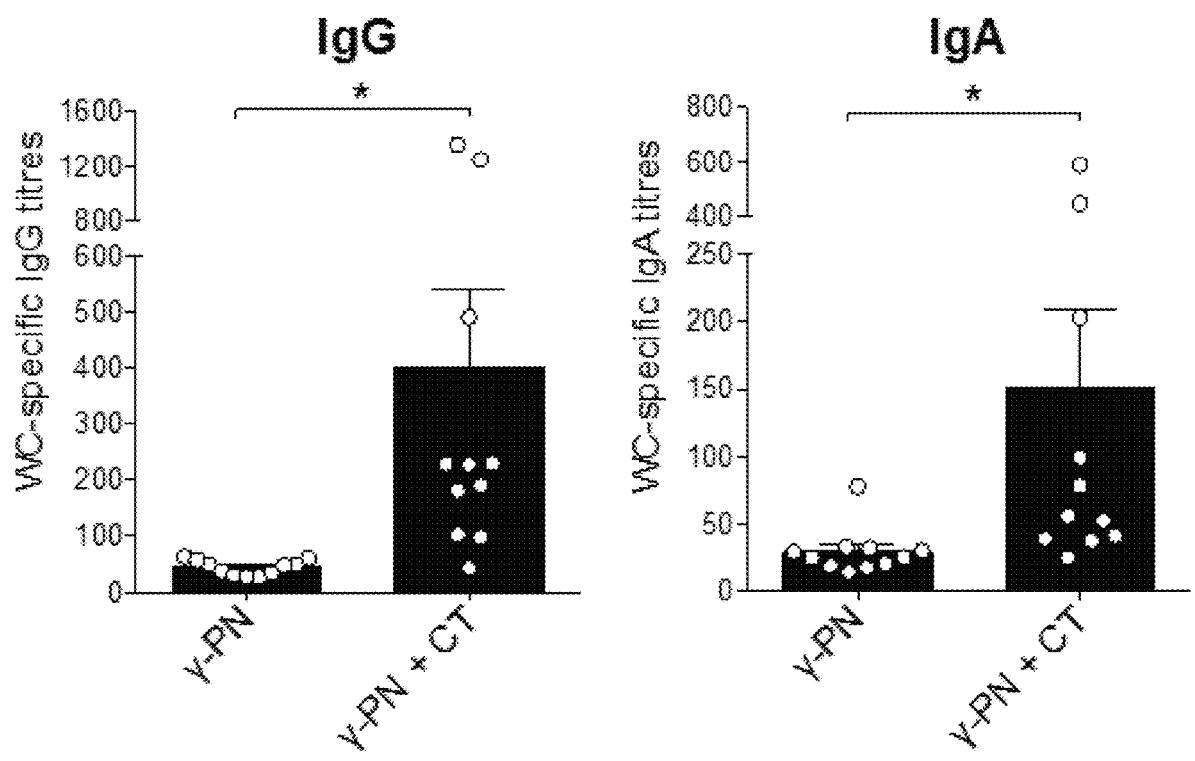
Figure 18:
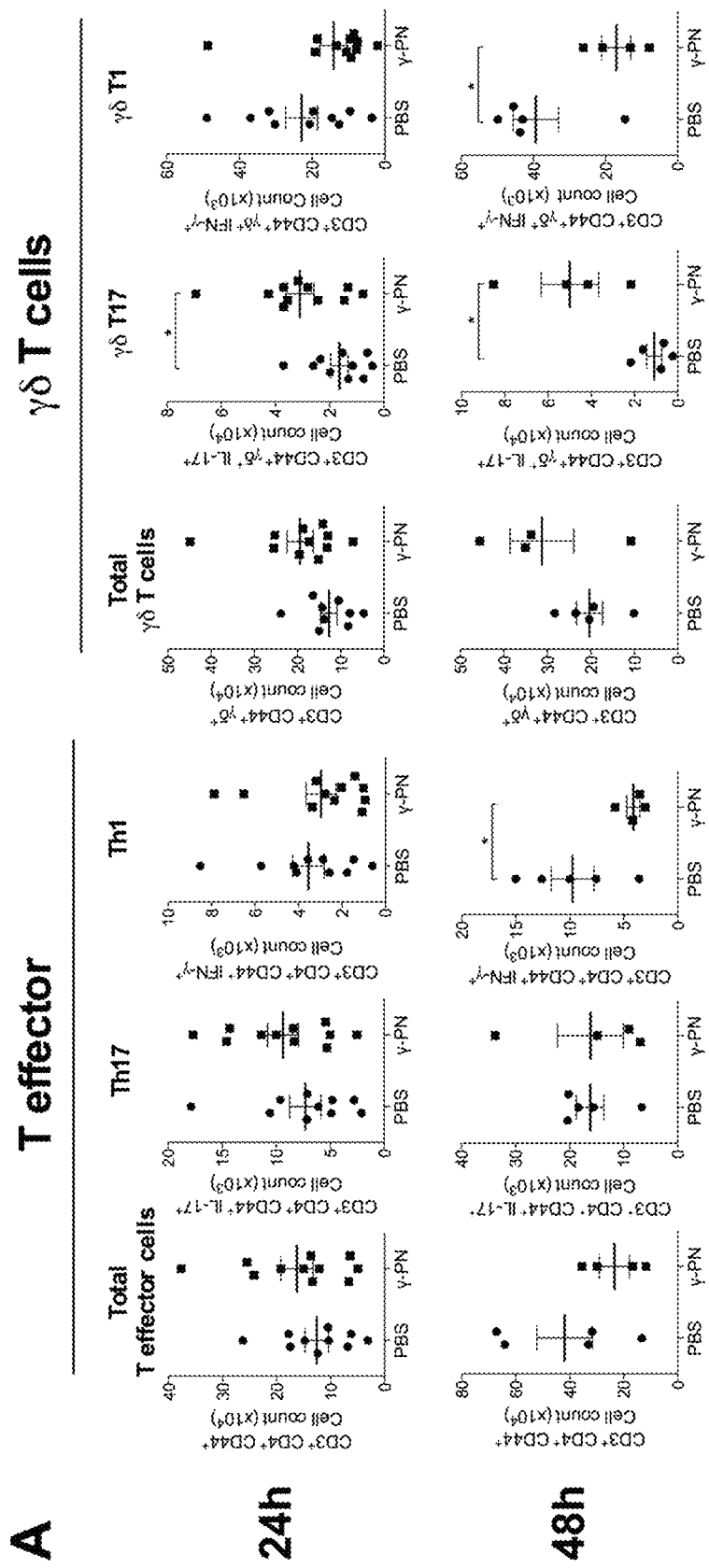
Figure 19A:
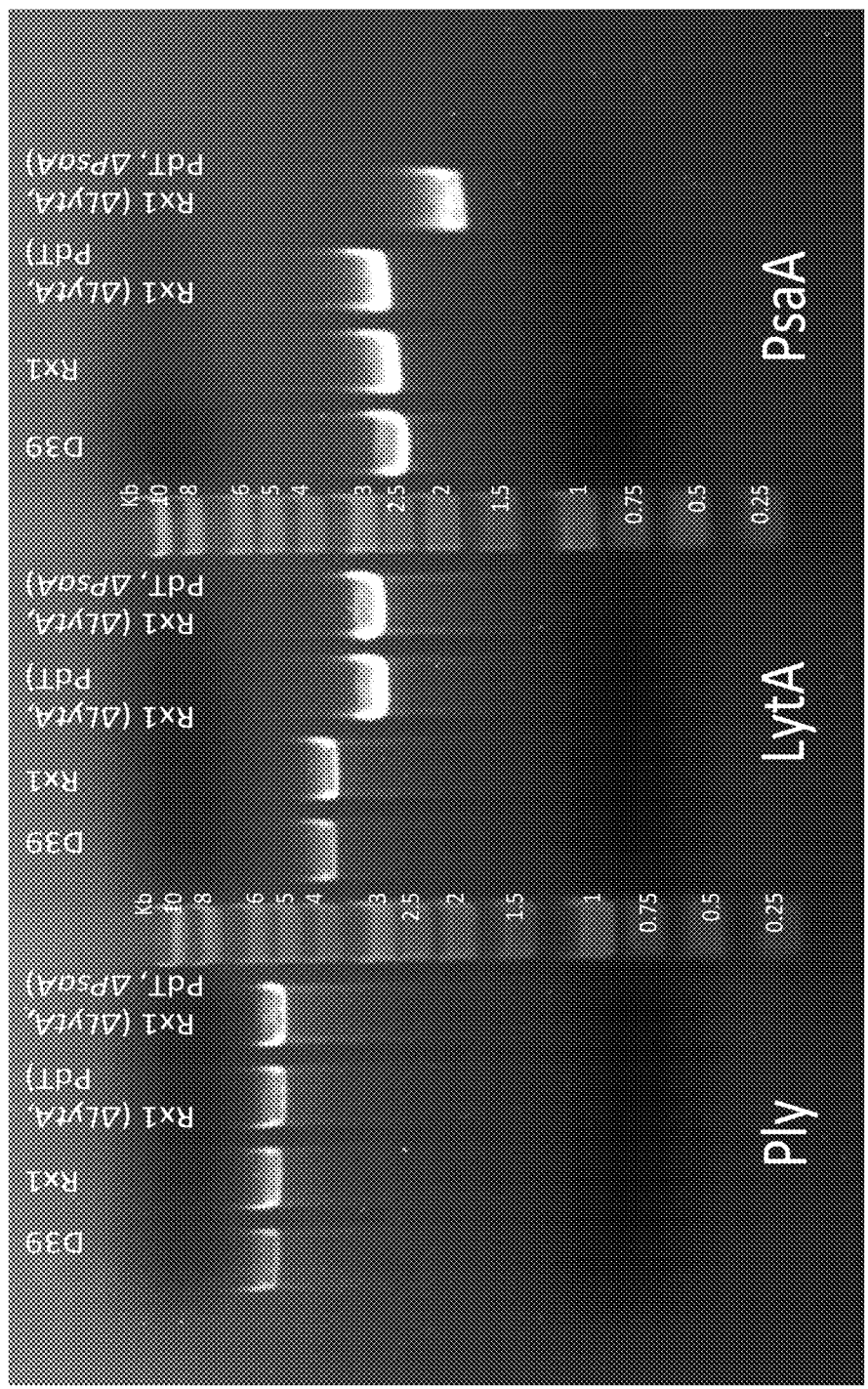
Figure 19B:
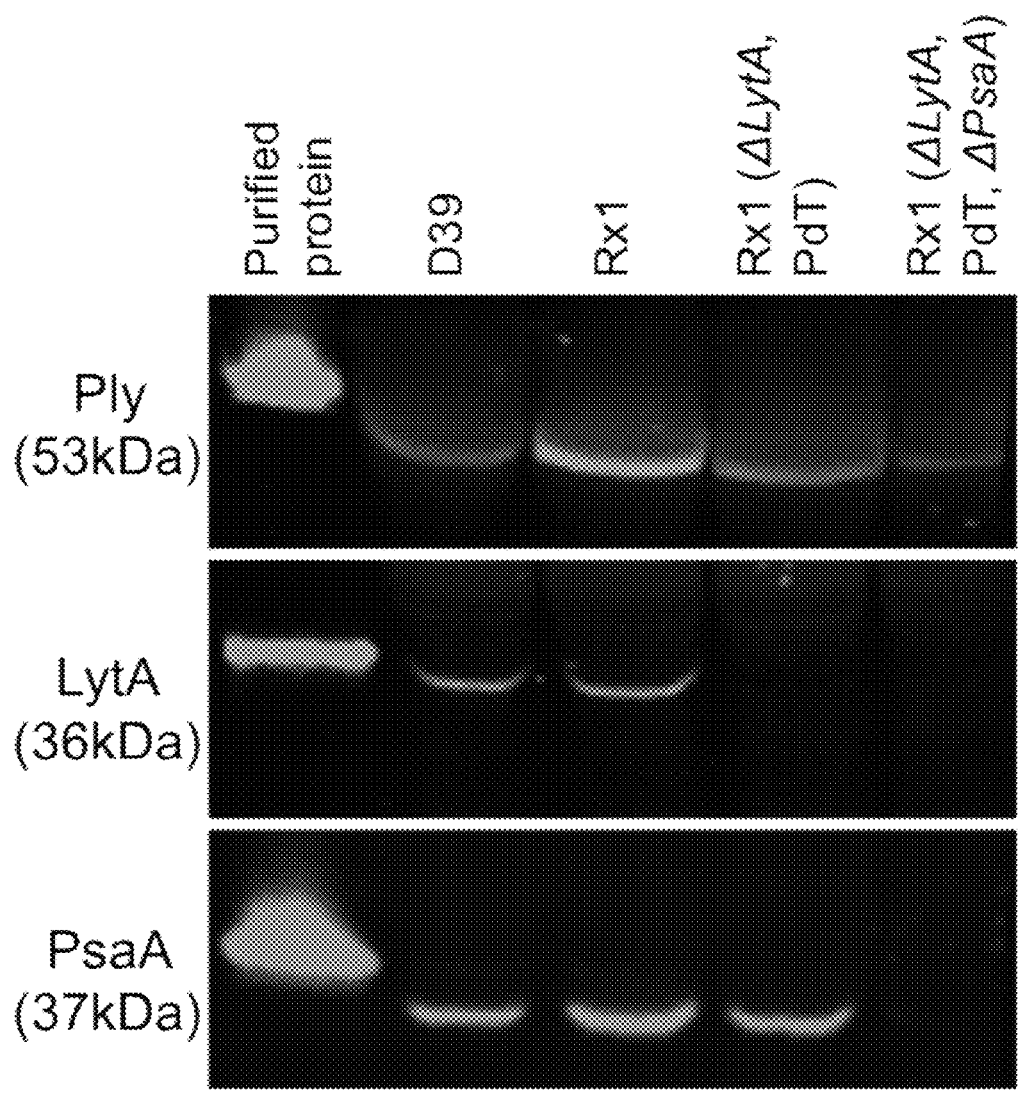
Figure 19C:
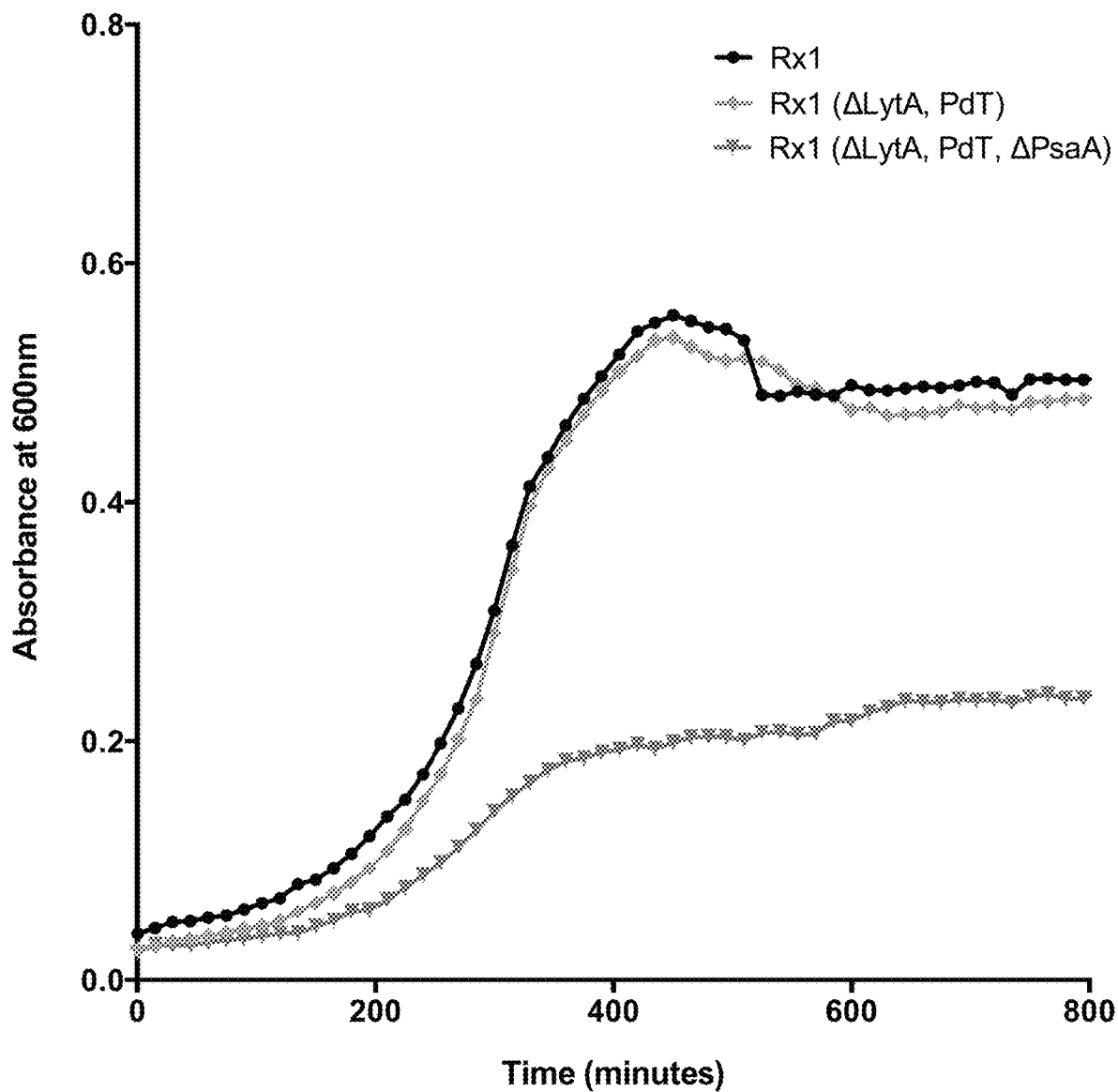
Figure 20:
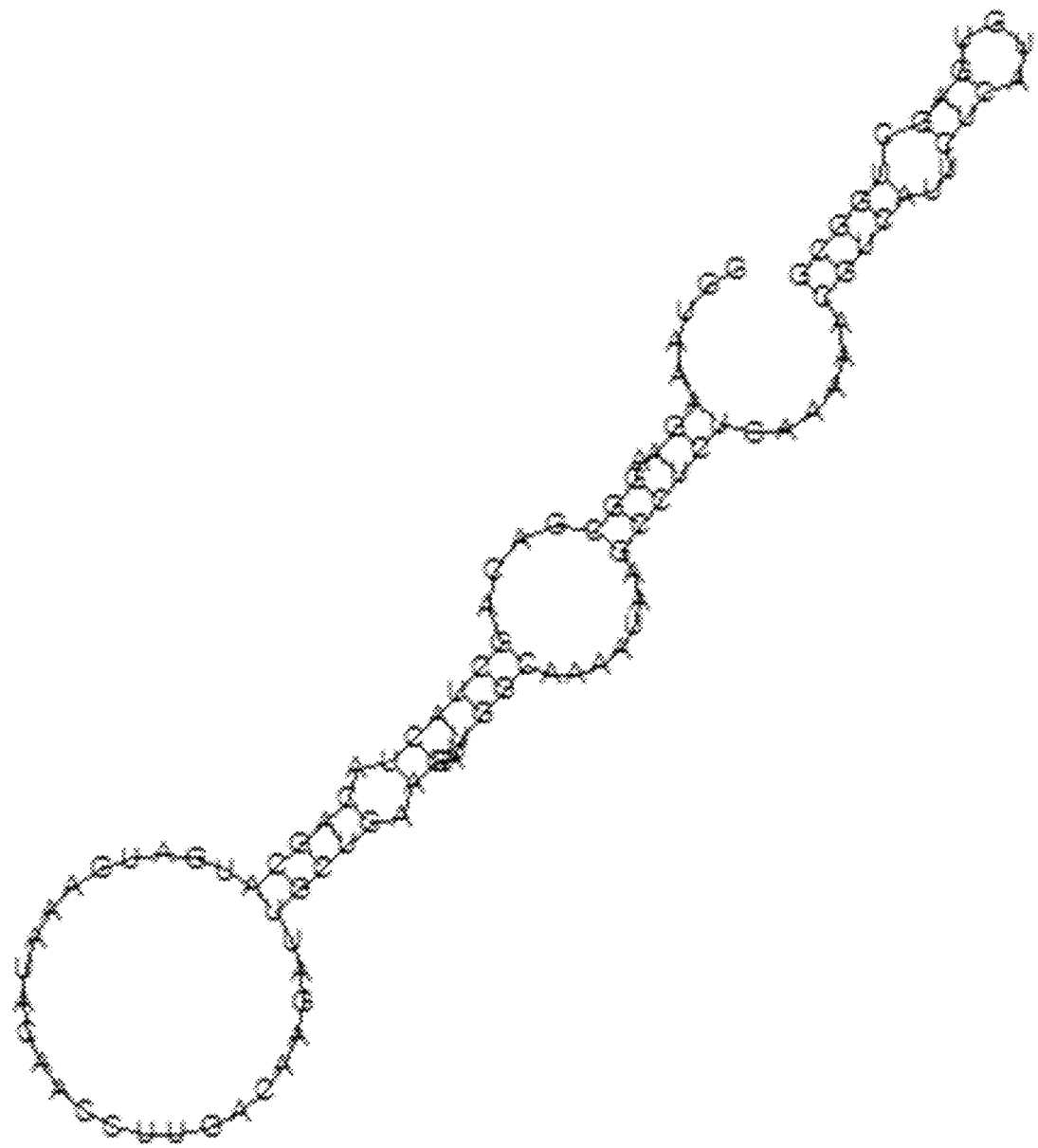
Figure 21A:
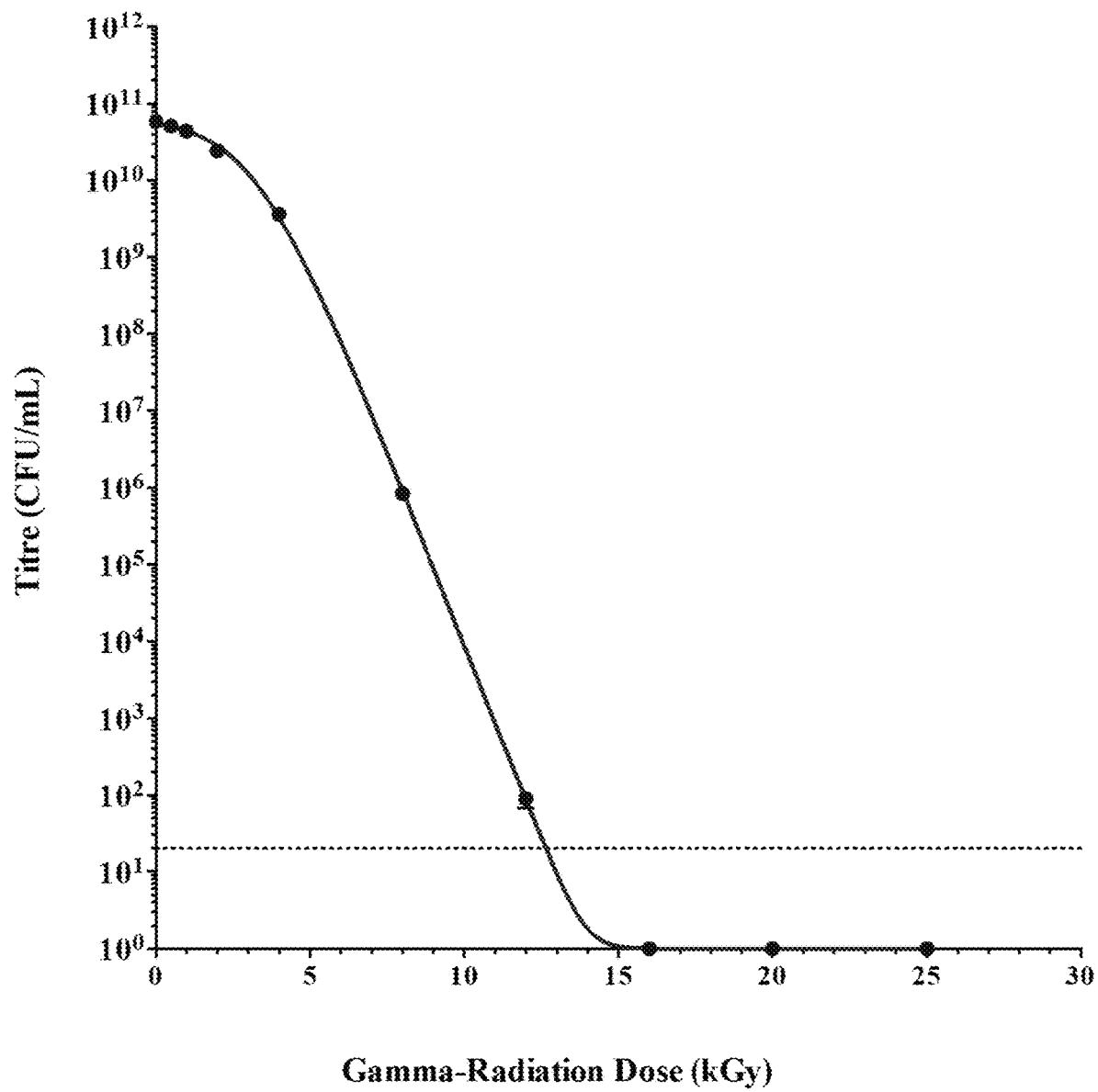
Figures 21B, 21C:
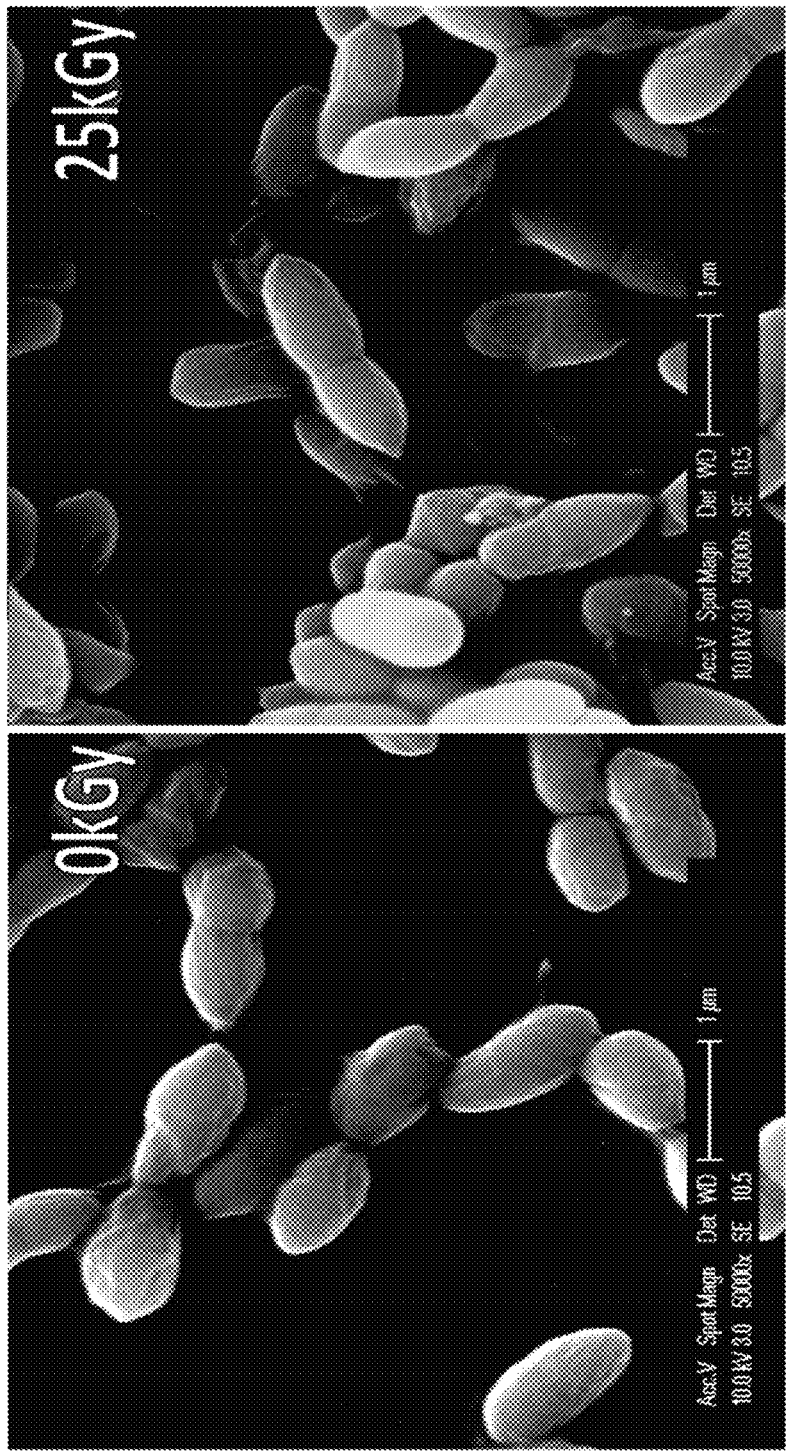

10A), and purified antigens Ply (FIG. 10B) and CbpA (FIG. 10C). γ-PN=gamma-irradiated *S. pneumoniae* Rx1 (ΔLytA, PdT);

FIG. 11 provides a graph showing the percentage survival of wild-type C57/BL6 and B-cell deficient C57/BL6 (μMT) mice vaccinated intranasally with gamma-irradiated *S. pneumoniae* Rx1 (ΔLytA, PdT) and challenged with a lethal dose of *Streptococcus pneumoniae* strain D39. **p=<0.01; γ-PN=gamma-irradiated *S. pneumoniae* Rx1 (ΔLytA, PdT);

FIG. 12 shows the results of cytokine analyses conducted on supernatants from cultured splenocytes derived from mice vaccinated intranasally with *S. pneumoniae* Rx1 (ΔLytA, PdT). Interleukin-17A (IL-17A) (FIG. 12A) and interferon-gamma (IFN-γ) levels (FIG. 12B) in supernatants from the splenocytes following stimulation with *S. pneumoniae* antigen MalX, ConA, or the whole gamma-irradiated Rx1 (ΔLytA, PdT) vaccine are indicated. FIGS. 12C and 12D show the results of intracellular cytokine staining performed on cultured splenocytes in the presence of MalX or the vaccine to gauge the proportion of Th1 cells (using IFN-γ+), Th2 cells (IL-4+), Th17 cells (IL-17+) and T-reg cells (Foxp3+) induced after 72 h of stimulation. γ-PN=gamma-irradiated *S. pneumoniae* Rx1 (ΔLytA, PdT);

FIG. 13 shows percentage change in body weight following challenge with influenza virus strain A/PR8 of (i) mice given PBS as a control (FIG. 13A) and (ii) mice intranasally vaccinated *S. pneumoniae* Rx1 (ΔLytA, PdT) (FIG. 13B) three weeks prior to A/PR8 challenge. γ-PN=gamma-irradiated *S. pneumoniae* Rx1 (ΔLytA, PdT);

FIG. 14 shows bacterial counts in the lungs (FIG. 14A) and nasopharynx (FIG. 14B) after challenge with *S. pneumoniae* strain EF3030 (serotype 19F) of mice that had been intranasally vaccinated with cholera toxin (CT) only (control) or *S. pneumoniae* Rx1 (ΔLytA, PdT) plus cholera toxin. FIG. 14C and FIG. 14D shows the duration of survival of mice challenged with *S. pneumoniae* strain D39 (serotype 2) or *S. pneumoniae* strain P9 (serotype 6A), respectively, that had been intranasally vaccinated with CT only (control) or *S. pneumoniae* Rx1 (ΔLytA, PdT) plus CT. *p=<0.05; **p=<0.01; γ-PN=gamma-irradiated *S. pneumoniae* Rx1 (ΔLytA, PdT);

FIG. 15 shows the results of intracellular cytokine staining performed to gauge the proportion of Th1 cells (using IFN-γ+), Th2 cells (IL-4+), Th17 cells (IL-17+) & T-reg cells (Foxp3+) induced after 72 h of stimulation of splenocytes with the gamma-irradiated *S. pneumoniae* Rx1 (ΔLytA, PdT) vaccine or MalX antigen from mice vaccinated intranasally with cholera toxin (CT) only (control) or *S. pneumoniae* Rx1 (ΔLytA, PdT) plus CT (FIG. 15A and FIG. 15B). Cytokine analyses were also conducted on supernatants from cultured splenocytes. Interleukin-17A (IL-17A) and interferon-gamma (IFN-γ) levels (FIG. 15C) in supernatants from splenocytes following stimulation with MalX or the gamma-irradiated *S. pneumoniae* Rx1 (ΔLytA, PdT) vaccine, are indicated. γ-PN=gamma-irradiated *S. pneumoniae* Rx1 (ΔLytA, PdT);

FIG. 16 shows the results of ELISAs measuring *S. pneumoniae*-specific antibody responses to un-irradiated whole Rx1 (ΔLytA, PdT) bacterial cells in serum from mice vaccinated intranasally with gamma-irradiated *S. pneumoniae* Rx1 (ΔLytA, PdT) in the presence or absence of cholera toxin adjuvant. γ-PN=gamma-irradiated *S. pneumoniae* Rx1 (ΔLytA, PdT);

FIG. 17 provides a graph showing the percentage survival of wild-type C57/BL6 mice vaccinated intranasally with gamma-irradiated *S. pneumoniae* Rx1 (ΔLytA, PdT) and challenged with a lethal dose of *S. pneumoniae* strain D39. Mice were injected with neutralising antibodies to IFN-γ or IL-17, or relevant isotype control antibodies at 24 h before challenge, 6 h post challenge and 48 h post challenge. *P=<0.05, **P=<0.01; γ-PN=gamma-irradiated *S. pneumoniae* Rx1 (ΔLytA, PdT);

FIG. 18 shows the total number of T effector cells (Th1 and Th17), γδ T cells (γδT1 and γδT17) and phagocytic cells (macrophages and neutrophils) in the lungs induced 24 and 48 hours after live challenge with *S. pneumoniae* D39 in mice vaccinated with gamma-irradiated *S. pneumoniae* Rx1 (ΔLytA, PdT) compared to un-vaccinated mice;

FIG. 19 shows the results of PCR and Western blot analyses of strains D39, Rx1, Rx1 (ΔLytA, PdT) and Rx1 (ΔLytA, PdT, ΔPsaA). It also shows growth of Rx1, Rx1 (ΔLytA, PdT) and Rx1 (ΔLytA, PdT, ΔPsaA). For PCR, the genetic loci for ply, lytA and psaA genes were amplified (FIG. 19A). For the Western blot, antisera against Ply, LytA and PsaA were used (FIG. 19B). For growth, bacteria were inoculated at A600 of 0.05 into SILAC RPMI 1640 Flex Media (supplemented with glucose) and statically cultured at 37° C. in 5% $CO_2$ (FIG. 19C). This confirms the successful deletion of the psaA gene from Rx1 (ΔLytA, PdT) to generate Rx1 (ΔLytA, PdT, ΔPsaA) and demonstrates the growth defect of the Rx1 (ΔLytA, PdT, ΔPsaA) strain in media not supplemented with $Mn^{2+}$;

FIG. 20 shows the predicted secondary structure of the mRNA transcript encoded by the ΔpsaA gene; and FIG. 21 provides a graph depicting *S. pneumoniae* Rx1 (ΔLytA, PdT, ΔPsaA) viability following exposure to various dosages of gamma-irradiation on dry ice (FIG. 21A). The scanning electron microscopy images of the physical morphology of *S. pneumoniae* Rx1 (ΔLytA, PdT, ΔPsaA) that had either not been irradiated (FIG. 21B) or irradiated at 25 kGy (FIG. 21C) are shown.

Figure 22:
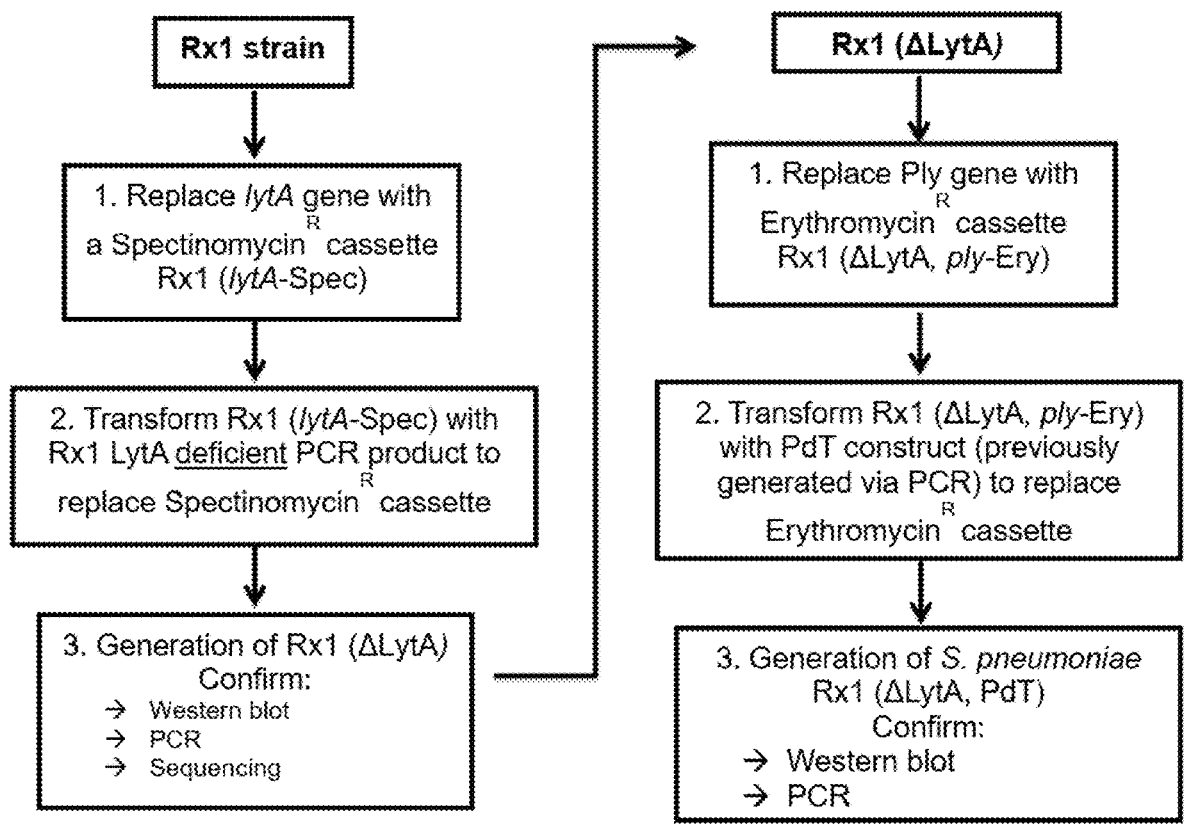

FIG. 22 is a flow chart illustrating a procedure adopted to modify strain Rx1 to remove the lytA gene coding for autolysin and to replace the ply gene coding for pneumolysin with a mutant derivative of pneumolysin expressing PdT.

FIG. 23 depicts LytA gene sequence, including flanking regions, of *Streptococcus pneumonia*. The lytA coding sequence for autolysin (LytA) is shown in italic/underline with the ATG start codon and TAA stop codon highlighted in bold/italics. The −35 and −10 and sigma70 promoter recognition sequences are shaded in light and dark grey, respectively. Squared/unbold nucleotides denote a potential transcription binding site(s) (TFBs) for RpoD. The bold A in the middle of the TFBs represent a predicted Transcription Start Site (TSS) position for the lytA mRNA. The upstream and downstream nucleotides that immediately flank the ATG start codon and TAA stop codon are squared/bold. The entire coding region of the lytA gene was deleted, in-frame, by slice-overlap extension PCR, such that the squared/bold nucleotide sequences in SEQ ID NO: 1 upstream and downstream of lytA are fused together.

FIG. 24A depicts a gene sequence of in *Streptococcus pneumoniae* strain Rx1ΔLytA (and derivatives) following deletion of the lytA gene. FIG. 24B is the messenger RNA (mRNA) transcript encoded by the ΔlytA gene. Ribonucleotides shown in bold black and underlined are predicted to form a typical double-stranded (ds) stem-loop structure permitting Rho-dependent termination.

Figure 25:
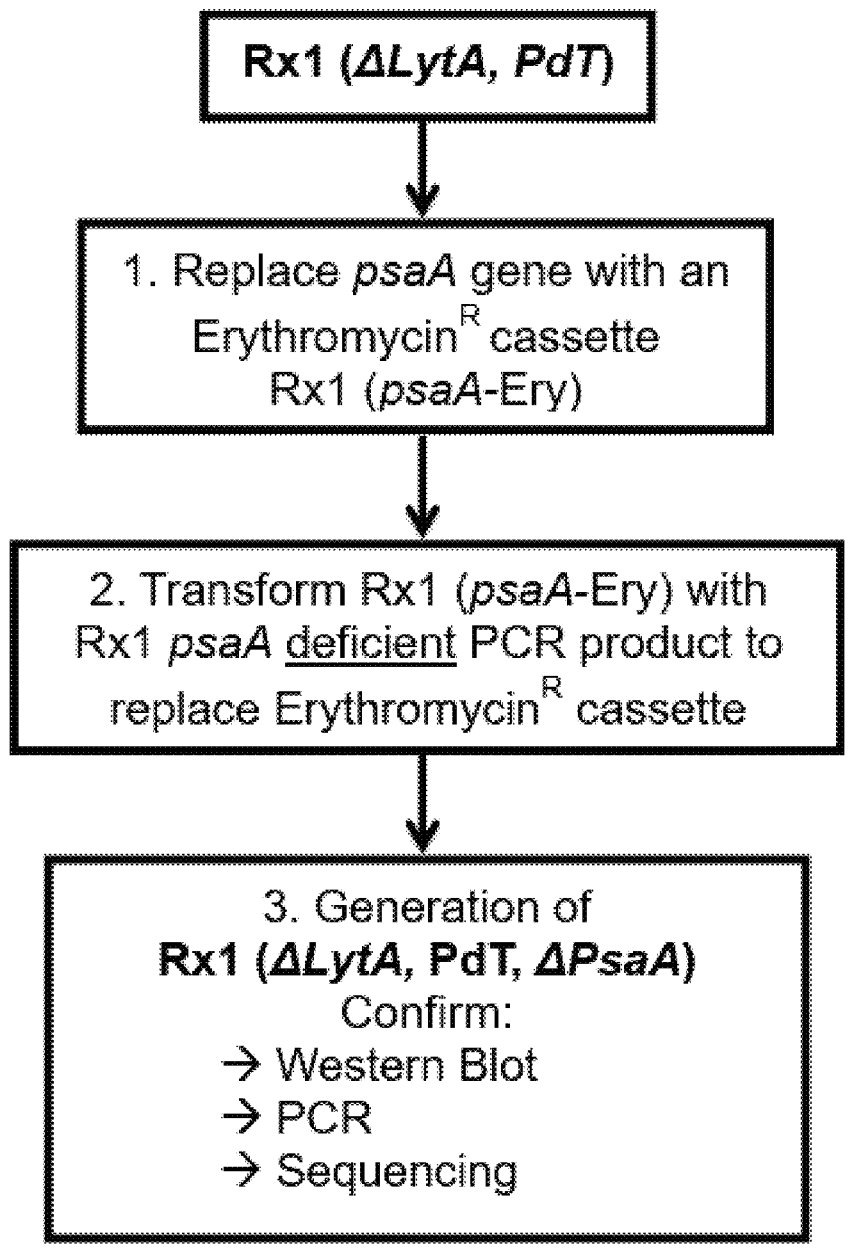

FIG. 25 is a flow chart illustrating a procedure adopted to modify strain Rx1(ΔLytA, PdT) to remove the psaA gene coding for pneumococcal surface antigen A.

FIG. 26 depicts PsaA gene sequence, including flanking regions, of *Streptococcus pneumonia*. The psaA coding sequence for pneumococcal surface antigen A (PsaA) is shown in italic/underline with the ATG start codon and TAA stop codon highlighted in bold/italics. The −35 and −10 and sigma70 promoter recognition sequences are shaded in light and dark grey, respectively. The bold G 9 nucleotides upstream of the ATG start codon is the predicted Transcription Start Site (TSS) for the PsaA mRNA. The nucleotides immediately upstream of the ATG start codon and 56 nucleotides upstream of TAA stop codon are squared/bold and constitute the sites for PCR primer annealing. The coding region of the psaA gene between the primer annealing sites was deleted by splice-overlap extension PCR, such that the squared/bold nucleotide sequences in SEQ ID NO: 4 in psaA are fused together.

FIG. 27A depicts a gene sequence in Streptococcus pneumoniae strain Rx1 ΔLytA, PdT, ΔPsaA following deletion of the psaA gene. FIG. 27B is the messenger RNA (mRNA) transcript coded by the ΔpsaA gene. Ribonucleotides shown in bold black and underlined are predicted to form a typical double-stranded (ds) stem-loop structure permitting Rho-dependent termination.

DEFINITIONS

As used in this application, the singular form "a", "an" and "the" include plural references unless the context clearly dictates otherwise. For example, the phrase "protein" also includes a plurality of proteins.

As used herein, the term "comprising" means "including." Variations of the word "comprising", such as "comprise" and "comprises," have correspondingly varied meanings. Thus, for example, a vaccine "comprising" gamma-irradiated streptococcal strain A may consist exclusively of gamma-irradiated streptococcal strain A or may include one or more additional components (e.g. gamma-irradiated streptococcal strain B).

As used herein the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

The term "therapeutically effective amount" as used herein, includes within its meaning a non-toxic but sufficient amount of an agent or composition for use in the present invention to provide the desired therapeutic effect. The exact amount required will vary from subject to subject depending on factors such as the species being treated, the age and general condition of the subject, the severity of the condition being treated, the particular agent being administered, the mode of administration and so forth. Thus, it is not possible to specify an exact "effective amount" applicable to all embodiments. However, for any given case, an appropriate "effective amount" may be determined by one of ordinary skill in the art using only routine experimentation.

As used herein the term "photon-radiation" will be understood to encompass both gamma-radiation (i.e. gamma-rays) and X-radiation (i.e. X-rays). Accordingly, a "photon-irradiated" material may be one that has been exposed to gamma-radiation and which has consequently become "gamma-irradiated", one that has been exposed to X-radiation and which has consequently become "X-irradiated", or both. By way of non-limiting example only, to become photon-irradiated a material may be subjected to photon-radiation at energies of at least 0.01 MeV, at least 0.1 MeV, at least 0.5 MeV, between 0.01 MeV and 0.5 MeV, between 0.01 MeV and 1 MeV, between 0.01 MeV and 10 MeV, between 0.5 MeV and 20 MeV, between 0.5 MeV and 15 MeV, between 0.5 MeV and 10 MeV, between 0.5 MeV and 5 MeV, between 0.5 MeV and 2 MeV, or between 1 MeV and 2 MeV (e.g. 1.25 MeV).

As used herein, the term "attenuated" in the context of bacteria will be understood to mean that the bacteria are capable of establishing only non-pathogenic infection in a host to which they are administered, for a time period sufficient to induce an immune response in the host. The bacteria are not however capable of establishing long-term infection or establishing pathogenic infection that is detrimental to a non-immunocompromised host to which the attenuated bacteria are administered.

As used herein the terms "induce", "inducing", "enhance" and "enhancing" in the context of immunity or an immune response refer to an increase in immunity or an immune response above existing levels which may be absent or measurable.

As used herein, the term "subject" includes any animal of economic, social or research importance including bovine, equine, ovine, primate, avian and rodent species. Hence, a "subject" may be a mammal such as, for example, a human or a non-human mammal (e.g. a pig, cat, dog, cow, horse, or sheep). Also included within the scope of this term are laboratory animals (e.g. rodents, rabbits, and the like), birds (e.g. poultry), fish and crustaceans.

As used herein the terms "prevent", "prevention" and "preventing" in the context of a given infection and/or a disease or condition arising from the infection will be understood to mean that a subject has a reduced propensity to develop the infection, and/or disease or condition upon exposure to a pathogenic organism causative of the infection, disease or condition. The reduced propensity to develop the infection and/or disease or condition will be understood to include both a diminished propensity and a lack of any propensity.

As used herein the terms "treat" and "treating" in the context of a given infection and/or a disease or condition arising from the infection will be understood to encompass reducing the number of pathogenic organisms infecting a subject and/or reducing any symptoms of the infection and/or symptoms of a disease or condition arising from the infection.

It will be understood that use of the term "about" herein in reference to a recited numerical value includes the recited numerical value and numerical values within plus or minus ten percent of the recited value.

It will be understood that use of the term "between" herein when referring to a range of numerical values encompasses the numerical values at each endpoint of the range. For example, a polypeptide of between 10 residues and 20 residues in length is inclusive of a polypeptide of 10 residues in length and a polypeptide of 20 residues in length.

Any description of prior art documents herein, or statements herein derived from or based on those documents, is not an admission that the documents or derived statements are part of the common general knowledge of the relevant art.

For the purposes of description all documents referred to herein are hereby incorporated by reference in their entirety unless otherwise stated.

DETAILED DESCRIPTION

The following detailed description conveys exemplary embodiments of the present invention in sufficient detail to enable those of ordinary skill in the art to practice the present invention. Features or limitations of the various embodiments described do not necessarily limit other embodiments of the present invention or the present invention as a whole. Hence, the following detailed description does not limit the scope of the present invention, which is defined only by the claims.

Currently used vaccines against streptococcal infection are generally polysaccharide vaccines containing purified capsular polysaccharides from multiple serotypes (most recently the PCV23 vaccine containing polysaccharides from 23 serotypes), or conjugated vaccines containing capsular polysaccharides conjugated to diphtheria toxoid or other protein antigens of non-streptococcal origin. Serotype replacement is a significant problem associated with polysaccharide vaccines, and conjugate vaccines induce immunity against only a subset of the serotypes covered by the polysaccharide vaccines. For example, there are more than 90 recognised serotypes of Streptococcus pneumoniae and most have been shown to cause disease. The immunity induced by currently available streptococcal vaccines is thus inadequate to establish broad immunity against the majority of streptococcal species and/or serotypes within certain pathogenic species. In contrast to viruses, the creation of safe live-attenuated bacterial vaccines is difficult. Comparatively, bacteria have a far larger number of genes and it is thus more difficult to preclude the reversion of mutant/attenuated bacteria back to a pathogenic form after administration to a vaccine recipient. Live bacterial vaccines are also unsuitable for administration to immunocompromised individuals such as those undergoing chemotherapy for malignancies, HIV patients, and young or elderly subjects. These individuals are effectively precluded from receiving any form of live attenuated streptococcal vaccine, despite being more susceptible to various forms of streptococcal infection.

The present invention provides vaccines capable of inducing heterotypic immunity against different streptococcal species and/or different streptococcal serotypes (also referred to herein as "vaccines of the invention" or "a vaccine of the invention"). The vaccines contain killed streptococcal bacteria thus alleviating potential issues arising from live attenuated vaccines. The vaccines are also capable of inducing immunity against a broad range of streptococcal species and/or serotypes, thus reducing the potential impact of serotype replacement.

Also provided herein are methods for manufacturing vaccines of the invention, as well as medicaments and pharmaceutical compositions comprising the vaccines.

The present invention also relates to methods of preventing or treating streptococcal infection in a subject. The methods involve administration of a vaccine of the invention to a subject. The vaccine may be administered for prophylactic or therapeutic purposes. The methods may induce heterotypic immunity in the subject against a plurality of different streptococcal species and/or subtypes.

Although not a required limitation, vaccines of the present invention are preferably formulated for and administered via mucosal surfaces. For example, the vaccines may be administered intranasally which in certain embodiments may stimulate more effective immune responses depending on the particular target disease or condition.

Streptococcal Vaccine Preparations

Streptococcal Strains

Vaccines of the invention are based on attenuated or whole killed streptococcal bacteria and derivatives thereof attenuated or killed by exposure to gamma-irradiation. The streptococcal bacteria may be pathogenic bacteria capable of establishing a detrimental infection in a host organism. Vaccines of the invention may comprise combinations of different streptococcal bacteria attenuated or killed by exposure to photon-radiation (e.g. gamma-radiation and/or X-radiation) including, for example, combinations of different streptococcal species, and/or combinations of different streptococcal serotypes within the same streptococcal species.

The streptococcal bacteria may, for example, be alpha-, beta-, or gamma-haemolytic streptococci, as classified according to well-characterised haemolytic properties or lack thereof in the case of gamma-haemolytic streptococcal bacteria.

Non-limiting examples of suitable alpha-haemolytic streptococcal bacteria include Streptococcus pneumoniae and viridans streptococci (e.g. S. mutans, S. sanguinis, S. mitis, S. oxalis, S. sobrinus, S. milleri). Also within the scope of the present invention are individual serotypes of these streptococcal species.

Non-limiting examples of suitable beta-haemolytic streptococcal bacteria include those classified under the Lancefield grouping (Groups A-H, L, N and R/S) based on the carbohydrate composition of cell wall bacterial antigens (polysaccharides). For example, the beta-haemolytic bacteria may include any one or more of S. pyogenes (Group A), S. agalactiae (Group B), S. equisimilis (Group C), S. equi (Group C), S. zooepidemicus (Group C), S. dysgalactiae (Group C), Enterococcus faecalis (Group D), S. bovis (Group D), S. milleri (Group E), S. mutans (Group E), S. anginosus (Group F), S. canis (Group G), S. dysgalactiae (Group G), S. sanguis (Group H), S. dysgalactiae (Group L), Lactococcus lactis (Group N), and S. suis (Group R/S). Also within the scope of the present invention are individual serotypes of these streptococcal species.

In some embodiments, vaccines of the invention comprise one or more serotypes of Streptococcus pneumoniae. Accordingly, the vaccines may comprise any one of more of S. pneumoniae serotypes 1, 2, 3, 4, 5, 6A, 6B, 6C, 6D, 7A, 7B, 7C, 7F, 8, 9A, 9L, 9N, 9V, 10A, 10B, 10C, 10F, 11A, 11B, 11C, 11D, 11F, 12A, 12B, 12F, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 27, 28A, 28F, 29, 31, 32A, 32F, 33A, 33B, 33C, 33D, 33F, 34, 35A, 35B, 35C, 35F, 36, 37, 38, 39, 40, 41A, 41F, 42, 43, 44, 45, 46, 47A, 47F, and/or 48.

In some embodiments, the vaccines comprise any one or more of S. pneumoniae serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F.

Streptococcal Derivatives

Vaccines of the present invention may comprise photon-irradiated (e.g. gamma-irradiated and/or X-irradiated) streptococcal derivatives. The streptococcal derivatives may be recombinant forms of streptococcal bacteria arising from artificial genetic manipulation, or naturally-occurring mutant forms of streptococcal bacteria. Without any particular limitation, the streptococcal derivatives may comprise one or more genetic modifications that reduce pathogenicity.

By way of non-limiting example only, the streptococcal derivatives may comprise a genetic alteration which disrupts or removes the capsule locus (cps). For example, any one or more of the S. pneumoniae cpsA, cpsB, cpsC, cpsD and/or cpsE genes, or homologous genes in other streptococcal species, may be modified in order to prevent, disrupt or modify capsule production (e.g. by recombination and the like). Alternatively, the streptococcal derivatives may have spontaneous mutations in these or other genes resulting in naturally-occurring non-encapsulated streptococcal bacteria. The streptococcal derivatives may lack all or at least a portion of the capsule locus. In some embodiments, the streptococcal derivatives lacking a capsule are *Streptococcus pneumoniae* strain Rx1, or Rx1 derivatives.

Additionally or alternatively, the streptococcal derivatives may comprise a genetic alteration which reduces or prevents the production or activity of other target proteins. By way of non-limiting example only, the genetic alteration may exist in: one or more genes encoding a choline-binding protein; one or more genes encoding an autolysin (e.g. *S. pneumoniae* lytA, lytB, lytC or homologous genes in other streptococcal bacteria); one or more genes that confer a nutrient/cofactor (e.g. a metal ion) requirement for growth (e.g. *S. pneumoniae* psaA or homologous genes in other streptococcal bacteria); one or more genes encoding a protective antigen (e.g. *S. pneumoniae* pspA or homologous genes in other streptococcal bacteria); and/or one or more genes encoding virulence determinants or regulators (e.g. *S. pneumoniae* codY, comC, comD, cps2A, csp4A, glpO, mgrA, nanA, nanB, pavA, pcpA, phtA, phtB, phtD, phtE, piuA, piaA, ply, prtA, psaA, psrP, rrgA, rrgB, spxB, and homologs of these genes in other streptococcal bacteria).

Additionally or alternatively, the streptococcal derivatives may comprise a genetic alteration resulting in an auxotroph with reduced pathogenicity and/or growth in vivo. By way of non-limiting example only, the genetic alteration may exist in one or more genes encoding a thymidylate synthase.

Additionally or alternatively, the streptococcal derivatives may comprise one or more (external) genes from: a streptococcal bacterium that is of the same species but a different serotype; a streptococcal bacterium that is from a different species; a non-streptococcal bacterium; or a human or a non-human mammal (e.g. a pig, cat, dog, cow, horse, or sheep); a laboratory animal (e.g. a rodent or rabbit); a bird; and/or a subject to which the recombinant streptococcal bacteria are to be administered. In some embodiments, the external gene or genes disrupt or otherwise inactivate one or more endogenous gene or genes (e.g. any one or more genes as set out in the paragraph directly above). In other embodiments, the external gene or genes do not disrupt or inactivate any endogenous gene. By way of non-limiting example only, the external gene or genes encode proteins that induce or enhance an immune response in a subject to which the streptococcal derivatives are administered. The immune response may be innate, adaptive, or both. In some embodiments, the external gene or genes encode an immunomodulator (e.g. a cytokine, chemokine, antibody, fusion protein, peptide, protein, and/or hormone). In other embodiments, the external gene or genes may comprise an antigen from another different family of bacteria (e.g. a *Mycoplasma pneumoniae* antigen, a *Haemophilus influenzae* antigen, a *Chlamydophila pneumoniae* antigen, a *Moraxella catarrhalis* antigen, a *Staphylococcus aureus* antigen), a viral antigen (e.g. an adenovirus antigen, a coronavirus antigen, an influenza virus antigen, a parainfluenza virus antigen, a metapneumovirus antigen, a rhinovirus antigen, a respiratory syncitial virus antigen, an HIV antigen, a hepatitis virus antigen, or a herpes virus antigen, a measles virus antigen, a mumps virus antigen, a papillomavirus virus antigen, a rubella virus antigen, a Varicella Zoster virus antigen), a fungal/yeast antigen, a helminthic antigen, and/or a protozoan antigen.

Additionally or alternatively, the streptococcal derivatives may comprise a genetic alteration causing the bacteria to overexpress one or more target genes. In this context, "overexpression" will be understood to mean a level of expression that is increased compared to expression of the same gene without the genetic modification in a corresponding streptococcal bacterium, under the same biological conditions. The overexpression of a given target gene may, for example, induce or enhance an immune response in a subject against streptococcal strains that are parental to the streptococcal derivatives administered and/or against the streptococcal derivatives themselves. By way of non-limiting example only, the genetic alteration may increase the production of one or more genes in the streptococcal derivatives encoding a protein capable of activating the complement system (e.g. *S. pneumoniae* cbpA, pspA, ply, or homologs of these genes in other streptococcal bacteria).

Additionally or alternatively, the streptococcal derivatives may comprise a genetic alteration causing defective DNA repair capacity. The use of vaccines comprising photon-irradiated (e.g. gamma-irradiated and/or X-irradiated) streptococcal derivatives with decreased capacity to repair DNA lesions arising from photon-irradiation may be advantageous insofar as the dose of photon-irradiation needed for attenuation or inactivation can be reduced, while vaccine efficacy and safety can conversely be increased. In some embodiments, the streptococcal derivatives comprise a genetic alteration that disrupts or inactivates expression of one or more genes encoding a protein in a mismatch repair system (e.g. *S. pneumoniae* hex locus or homologs of this locus in other streptococcal bacteria). In other embodiments, the streptococcal derivatives comprise a genetic alteration that disrupts or inactivates expression of one or more genes encoding a DNA alkylation repair protein (e.g. *S. pneumoniae* DNA polymerase 4, hexA, hexB, mutS, radC, recA, recF, recN, recO, uvrA, uvrB, uvrC, uvrD or homologs of these genes in other streptococcal bacteria).

Additionally or alternatively, the streptococcal derivatives may comprise a genetic alteration that facilitates production of a double-stranded RNA (dsRNA). The dsRNA may be mRNA or tRNA. Without limitation, the length of the dsRNA may be more than 10, more than 15, more than 20, more than 25, more than 30, more than 35, more than 40, more than 45, more than 50, more than 55, more than, more than 65 or more than 70 base pairs in length. Additionally or alternatively, the length of the dsRNA may be: between about 10 and about 70 base pairs (bp); between about 10 and about 50 base pairs (bp); between about 10 and about 30 base pairs (bp); between about 20 and about 70 base pairs (bp); between about 20 and about 60 base pairs (bp); between about 20 and about 50 base pairs (bp); between about 20 and about 40 base pairs (bp); between about 20 and about 30 base pairs (bp); between about 30 and about 70 base pairs (bp); between about 40 and about 70 base pairs (bp); between about 50 and about 70 base pairs (bp); between about 60 and about 70 base pairs (bp); between about 30 and about 60 base pairs (bp); between about 30 and about 50 base pairs (bp); or between about 30 and about 40 base pairs (bp); in length. In some embodiments, the dsRNA is a component of a larger RNA molecule that is otherwise single-stranded. The larger RNA molecule may comprise multiple dsRNA components. The dsRNA may be an internal component or an end component of the larger RNA molecule. In some embodiments, the dsRNA may comprise a termination stem-loop sequence. The dsRNA may arise from a region of self-complementarity within the larger RNA molecule. Coding region(s)/exon(s) within a given gene of a streptococcal derivative can be engineered to include one or more region(s) of self-complementarity and thereby produce a dsRNA portion when transcribed.

The dsRNA may be capable of recognition by Toll-like receptor (TLR) proteins expressed by cells in a subject to which the streptococcal derivatives are administered. The TLR proteins may be located in the endoplasmic reticulum and/or endosomal compartment of the cells. The TLR proteins may be Toll-like receptor 3 (TLR3) proteins. Without limitation, the cells may be any one or more of B lymphocytes, T lymphocytes, natural killer cells and/or dendritic cells. Recognition of the dsRNA by the TLR3 protein may induce an immune response in the subject. The immune response may be an innate immune response. The immune response may be an interferon type-1 response and/or comprise the release of inflammatory cytokines.

In general, streptococcal derivatives used in vaccines of the invention will have a significant degree of genetic similarity to the parent strain from which they derive. By way of non-limiting example, a "streptococcal derivative" as referred to herein may have more than 70%, more than 75%, more than 80%, more than 85%, more than 90%, more than 92%, more than 94%, more than 95%, more than 96%, more than 97%, more than 98%, or more than 99% sequence homology to the parent streptococcal strain from which it is derived. By way of further non-limiting example, a "streptococcal derivative" as referred to herein may comprise a genetic alteration in one, two, three, four, five or more than five genes or regulatory sequences necessary for expression of those genes, when compared to corresponding of its parent strain. The genetic alteration may increase, decrease, or prevent expression of the gene or genes in question.

In one non-limiting embodiment, the streptococcal bacteria derivative may be an Rx1 strain. The autolysin gene (lytA) gene may be deleted or rendered non-functional in the Rx1 derivative strain. Additionally or alternatively, the pneumolysin gene (ply) may be deleted or rendered non-functional in the Rx1 derivative strain. For example, the ply gene may be replaced with another gene such as a toxoid version of ply.

Additionally or alternatively, the pneumococcal surface antigen A gene (psaA) gene may be deleted or otherwise rendered non-functional. The psaA gene of *S. pneumoniae* encodes the pneumococcal surface antigen A (PsaA) involved in $Mn^{2+}$ transport and resistance to oxidative stress. A psaA-deletion mutant as described herein may be defective in growth in low $Mn^{2+}$ environments and/or defective in pneumococcal competence. In non-limiting embodiments, a psaA-deletion mutant of Rx1 (ΔLytA, PdT) may be used to create a vaccine candidate strain Rx1 (ΔLytA, PdT, ΔPsaA) with reduced virulence, reduced competence, and/or reduced growth in low $Mn^{2+}$ environments. These features may add additional biosecurity and biosafety to Rx1 (ΔLytA, PdT, ΔPsaA) making it a suitable vaccine candidate for preparing a gamma-irradiated *S. pneumoniae* vaccine. Furthermore, fermentor growth of Rx1 (ΔLytA, PdT, ΔPsaA) under $Mn^{2+}$ stress conditions may induce changes in gene expression that increases the level of production of protective antigens. An improved level of protection may thus be afforded by use of vaccine product with higher level of expression of protective antigens.

Techniques for the genetic manipulation of bacteria are well known to those of ordinary skill in the art (see, for example, Vennison "*Laboratory Manual for Genetic Engineering*", PHI Learning Pvt. Ltd., 2010; Zyskind and Bernstein, "*Recombinant DNA Laboratory Manual*", Elsevier, 2014; Bose, "*Genetic Manipulation of Staphylococci*" in "Methods in Molecular Biology", Springer Protocols, volume 1106, pages 101-111, 2014; Hakenbeck and Chhatwal, "*Molecular Biology of Streptococci*", Horizon Scientific Press, 2007; Morona et al., "*The effect that mutations in the conserved capsular polysaccharide biosynthesis genes cpsA, cpsB and cpsD have on virulence of Streptococcus pneumoniae*", J. Infect. Dis. 189: 1905-1913, 2004; Morona et al., "*Mutational analysis of the carboxy-terminal $[YGX]_4$ repeat domain of CpsD, an autophosphorylating tyrosine kinase required for capsule biosynthesis in Streptococcus pneumonia*", J. Bacteriol. 185: 3009-3019, 2003; McAllister et al., "*Molecular analysis of the psa permease complex of Streptococcus pneumoniae*", Mol. Microbiol. 53:889-901, 2004; Mandi et al., "*Identification of a novel pneumococcal vaccine antigen preferentially expressed during meningitis in mice*", J. Clin. Invest. 122:2208-2220, 2012.

Photon-Radiation

Streptococcal bacteria and derivatives thereof in vaccines of the invention may be exposed to photon-radiation. As noted above, the term "photon-radiation" will be understood to encompass both gamma-radiation (i.e. gamma-rays) and X-radiation (i.e. X-rays). Accordingly, "photon-irradiated" streptococcal bacteria or their derivatives may be "gamma-irradiated" by way of exposure to gamma-radiation (i.e. gamma-rays), "X-irradiated" by way of exposure to X-radiation (i.e. X-rays), or both. As known to those of ordinary skill in the art, X-rays are identical to gamma-rays except they are emitted by the passage of electrons through an electric field of a nucleus rather than the nucleus itself upon radioactive decay. By way of non-limiting example only, to become photon-irradiated a material may be subjected to photon-radiation at energies of at least 0.01 MeV, at least 0.1 MeV, at least 0.5 MeV, between 0.01 MeV and 0.5 MeV, between 0.01 MeV and 1 MeV, between 0.01 MeV and 10 MeV, between 0.5 MeV and 20 MeV, between 0.5 MeV and 15 MeV, between 0.5 MeV and 10 MeV, between 0.5 MeV and 5 MeV, between 0.5 MeV and 2 MeV, or between 1 MeV and 2 MeV (e.g. 1.25 MeV).

Streptococcal bacteria and derivatives thereof in vaccines of the invention may be gamma-irradiated. Any suitable source of gamma-radiation may be used. Suitable gamma emitters include, but are not limited to $Ba^{137}$, $Co^{60}$, $Cs^{137}$, $Ir^{192}$, $U^{235}$, $Se^{75}$ and $Yb^{169}$.

Gamma-irradiation of the streptococcal bacteria and their derivatives may be performed using commercially available devices, for example, a Gammacell irradiator manufactured by Atomic Energy of Canada Ltd., Canada (e.g. Gammacell 40 Irradiator, Gammacell 220 Irradiator, Gammacell 1000 irradiator, Gammacell 3000 irradiator), a gamma-irradiator manufactured by J. L. Shepherd and Associates (San Fernando, Calif., USA), or a Nordion Gamma Cell-1000 irradiator manufactured by Nordion Inc. (Kanata, Ontario, Canada). Other suitable devices are described, for example, in U.S. Pat. Nos. 3,557,370 and 3,567,938.

Additionally or alternatively, streptococcal bacteria and derivatives thereof in vaccines of the invention may be X-irradiated. Any suitable source of X-radiation may be used. Suitable sources of X-radiation include, but are not limited to, the eXelis® sterilization X-ray machine manufactured by IBA Industrial (Louvain-la-Neuve, Belgium). Other suitable devices include for example, the RS2400® and RS3400® manufactured by Rad Source Technologies Inc. (Suwanee, Ga., USA).

In general, the streptococcal bacteria and their derivatives are exposed to a dose of photon-radiation (e.g. gamma-radiation and/or X-radiation) sufficient to attenuate or inactivate the bacteria/derivatives. Preferably, the dose of photon-radiation is sufficient to attenuate or inactivate the bacteria and their derivatives without substantially disrupting the structure of antigens (e.g. surface antigens). The immunogenicity of antigenic determinants may therefore be retained by the photon-irradiated bacteria and their derivatives. Preferably, the dose of photon-radiation is administered to the bacteria or their derivatives over a period of time and at a level sufficient to ensure that all bacteria/derivatives under treatment are exposed without adversely affecting the structural integrity of antigenic determinants.

As known to those of ordinary skill in the art, a measure for an absorbed dose of radiation is the gray (Gy), which is defined as 1 joule of energy deposited in 1 kilogram of mass. An old unit of measure for this is the rad, which stands for "radiation absorbed dose", where 1 Gy=100 rad.

Streptococcal bacteria and derivatives thereof for use in accordance with the present invention may be exposed to a total dose of photon-radiation (e.g. gamma-radiation and/or X-radiation) in the range of about $1 \times 10^3$ rad and about $2 \times 10^9$ rad (or about 10 Gy to about $2 \times 10^4$ kGy). In certain embodiments of the invention, the streptococcal bacteria or derivatives are exposed to a total dose of X-radiation and/or gamma-radiation of between about $1 \times 10^3$ rad and about $2 \times 10^9$ rad, between about $1 \times 10^3$ rad and about $1 \times 10^9$ rad, between about $1 \times 10^3$ rad and about $1 \times 10^8$ rad, between about $1 \times 10^3$ rad and about $1 \times 10^7$ rad, between about $1 \times 10^3$ rad and about $1 \times 10^6$ rad, between about $1 \times 10^3$ rad and about $1 \times 10^5$ rad, between about $1 \times 10^3$ rad and about $1 \times 10^4$ rad, between about $1 \times 10^3$ rad and about $2 \times 10^9$ rad, between about $1 \times 10^4$ rad and about $2 \times 10^9$ rad, between about $1 \times 10^5$ rad and about $2 \times 10^9$ rad, between about $1 \times 10^6$ rad and about $2 \times 10^9$ rad, between about $1 \times 10^7$ rad and about $2 \times 10^9$ rad, between about $1 \times 10^8$ rad and about $2 \times 10^9$ rad or between about $1 \times 10^9$ rad and about $2 \times 10^9$ rad.

In some embodiments of the invention, the streptococcal bacteria or derivatives are exposed to a total dose of photon-radiation (e.g. X-radiation and/or gamma-radiation) of between about $6.5 \times 10^4$ rad and about $2 \times 10^7$ rad (about 0.65 KGy to about 200 kGy). In other embodiments of the invention, the streptococcal bacteria or their derivatives are exposed to a total photon-radiation dose of about 10 kGy to about 12 kGy, about 12 kGy to about 14 kGy, about 14 kGy to about 16 kGy, about 10 kGy to about 20 kGy, about 14 kGy about 20 kGy, more than 10 about 12 kGy to about 14 kGy, more than 12kGy, more than 14 kGy, more than 16 kGy, more than 18 kGy, more than 20 kGy, $1.26 \times 10^6$ rad (12.6 kGy), a total photon-radiation dose of about $1 \times 10^6$ rad (about 10 kGy) photon-rays, or a total photon-radiation dose of about $1 \times 10^5$ rad (1 KGy).

The optimal dose of photon-radiation (e.g. gamma-radiation and/or X-radiation) may be influenced by factors such as the medium in which the streptococcal bacteria or their derivatives are present, the amount of bacteria/derivatives to be treated, and/or the subtype or strain under treatment. Accordingly, the total dose of photon-radiation, the exposure time and/or the level of photon-radiation applied over the period of exposure may be optimised to enhance the effectiveness of the treatment.

The total dose of photon-radiation (e.g. X-radiation and/or gamma-radiation) may be administered to the streptococcal bacteria or their derivatives cumulatively over a period of time. For example, photon-radiation on may be administered to the bacteria/derivatives at a level lower than that of the total dose, over a time period sufficient to achieve the total dose of photon-radiation required.

In one embodiment, preparations of streptococcal bacteria or their derivatives are maintained in a frozen and/or lyophilised state while being exposed to photon-radiation (e.g. gamma-radiation and/or X-radiation). This may facilitate the preservation of biological integrity and avoid unnecessary damage of antigens thereby enhancing the immunogenicity of photon-irradiated bacterial preparations, and in particular, their ability to elicit cross-reactive/cross-protective immunity against, for example, heterologous subtypes. In general, a photon-radiation dose of 10-20 kGy (e.g. more than 10, more than 12, more than 14, more than 16, or more than 18 kGy) may be effective for treating preparations of frozen and/or lyophilised streptococcal bacteria or their derivatives.

As mentioned above, it is preferable that treatment with photon-radiation is sufficient to inactivate the bacteria/derivatives without substantially disrupting the structure of bacterial antigens. Attenuation and/or inactivation of the streptococcal bacteria or their derivatives may be assessed using methods generally known in the art.

For example, bacterial attenuation and/or inactivation can be assessed by determining the number of viable bacteria that form colonies on agar media (i.e. the colony forming units) after being treated with photon-radiation (e.g. gamma-radiation and/or X-radiation).

The integrity of antigenic determinants can be assessed, for example, by reactivity with panels of monospecific antisera raised against purified native antigenic components using Western blotting, FACs analysis, or enzymatic assays of surface components.

Prophylactic and Therapeutic Methods

The invention provides prophylactic methods for the prevention of streptococcal infection in a subject. Also provided are therapeutic methods for treating streptococcal infection in a subject. The methods comprise administering photon-irradiated streptococcal bacteria and/or photon-irradiated derivatives thereof to the subject, for example, in the form of a vaccine of the invention. The photon-irradiated streptococcal bacteria and/or derivatives thereof may be gamma-irradiated, X-irradiated, or both.

The methods induce or enhance the immune response against streptococcal bacteria in the subject. The immune response may be cross-protective/heterologous insofar as it may induce or enhance the immune response against multiple serotypes of streptococcal bacteria. The methods may also comprise administering multiple different photon-irradiated (e.g. gamma-irradiated, X-irradiated, or both) streptococcal species or derivatives thereof, to thereby generate immunity against multiple species of streptococcal bacteria and various serotypes thereof.

The methods may induce or enhance an immune response against any one or more of the following streptococcal bacterial species: *Streptococcus agalactiae, Streptococcus bovis, Streptococcus canis, Streptococcus dysgalactiae, Streptococcus equi, Streptococcus equinus, Streptococcus equisimilis, Enterococcus faecalis, Enterococcus faecium, Streptococcus iniae, S. milleri, Streptococcus mutans, Streptococcus pneumoniae, Streptococcus pyogenes, Streptococcus salivarius, Streptococcus sanguinis, Streptococcus suis* and *Streptococcus uberis*.

In some embodiments, the methods comprise preventing or treating a streptococcal infection caused by a given streptococcal species by administering to the subject a photon-irradiated (e.g. gamma-irradiated and/or X-irradiated) preparation of the same streptococcal species. The streptococcal species serotype causative of the infection may be different to the photon-irradiated streptococcal species serotype administered.

By way of non-limiting example only, the methods may be used to prevent or treat:

(i) an infection, disease or condition caused by any one or more serotypes of *Streptococcus agalactiae* by administering one or more photon-irradiated (e.g. gamma-irradiated and/or X-irradiated) serotype(s) of *Streptococcus agalactiae*. The photon-irradiated *Streptococcus agalactiae* serotype(s) administered may differ from the serotype(s) causative of the infection, disease or condition;

(ii) an infection, disease or condition caused by any one or more serotypes of *Streptococcus bovis* by administering one or more photon-irradiated (e.g. gamma-irradiated and/or X-irradiated) serotype(s) of *Streptococcus bovis*. The photon-irradiated *Streptococcus bovis* serotype(s) administered may differ from the serotype(s) causative of the infection, disease or condition;

(iii) an infection, disease or condition caused by any one or more serotypes of *Streptococcus canis* by administering one or more photon-irradiated (e.g. gamma-irradiated and/or X-irradiated) serotype(s) of *Streptococcus canis*. The photon-irradiated *Streptococcus canis* serotype(s) administered may differ from the serotype(s) causative of the infection, disease or condition;

(iv) an infection, disease or condition caused by any one or more serotypes of *Streptococcus dysgalactiae* by administering one or more photon-irradiated (e.g. gamma-irradiated and/or X-irradiated) serotype(s) of *Streptococcus dysgalactiae*. The photon-irradiated *Streptococcus dysgalactiae* serotype(s) administered may differ from the serotype(s) causative of the infection, disease or condition;

(v) an infection, disease or condition caused by any one or more serotypes of *Streptococcus equi* by administering one or more photon-irradiated (e.g. gamma-irradiated and/or X-irradiated) serotype(s) of *Streptococcus equi*. The photon-irradiated *Streptococcus equi* serotype(s) administered may differ from the serotype(s) causative of the infection, disease or condition;

(vi) an infection, disease or condition caused by any one or more serotypes of *Streptococcus equinus* by administering one or more photon-irradiated (e.g. gamma-irradiated and/or X-irradiated) serotype(s) of *Streptococcus equinus*. The photon-irradiated *Streptococcus equinus* serotype(s) administered may differ from the serotype(s) causative of the infection, disease or condition;

(vii) an infection, disease or condition caused by any one or more serotypes of *Streptococcus agalactiae* by administering one or more photon-irradiated (e.g. gamma-irradiated and/or X-irradiated) serotype(s) of *Streptococcus agalactiae*. The photon-irradiated *Streptococcus agalactiae* serotype(s) administered may differ from the serotype(s) causative of the infection, disease or condition;

(viii) an infection, disease or condition caused by any one or more serotypes of *Streptococcus equisimilis* by administering one or more photon-irradiated (e.g. gamma-irradiated and/or X-irradiated) serotype(s) of *Streptococcus equisimilis*. The photon-irradiated *Streptococcus equisimilis* serotype(s) administered may differ from the serotype(s) causative of the infection, disease or condition;

(ix) an infection, disease or condition caused by any one or more serotypes of *Enterococcus faecalis* by administering one or more photon-irradiated (e.g. gamma-irradiated and/or X-irradiated) serotype(s) of *Enterococcus faecalis*. The photon-irradiated *Enterococcus faecalis* serotype(s) administered may differ from the serotype(s) causative of the infection, disease or condition;

(x) an infection, disease or condition caused by any one or more serotypes of *Enterococcus faecium* by administering one or more photon-irradiated (e.g. gamma-irradiated and/or X-irradiated) serotype(s) of *Enterococcus faecium*. The photon-irradiated *Enterococcus faecium* serotype(s) administered may differ from the serotype(s) causative of the infection, disease or condition;

(xi) an infection, disease or condition caused by any one or more serotypes of *Streptococcus iniae* by administering one or more photon-irradiated (e.g. gamma-irradiated and/or X-irradiated) serotype(s) of *Streptococcus iniae*. The photon-irradiated *Streptococcus iniae* serotype(s) administered may differ from the serotype(s) causative of the infection, disease or condition;

(xii) an infection, disease or condition caused by any one or more serotypes of *Streptococcus milleri* by administering one or more photon-irradiated (e.g. gamma-irradiated and/or X-irradiated) serotype(s) of *Streptococcus milleri*. The photon-irradiated *Streptococcus milleri* serotype(s) administered may differ from the serotype(s) causative of the infection, disease or condition;

(xiii) an infection, disease or condition caused by any one or more serotypes of *Streptococcus mutans* by administering one or more photon-irradiated (e.g. gamma-irradiated and/or X-irradiated) serotype(s) of *Streptococcus mutans*. The photon-irradiated *Streptococcus mutans* serotype(s) administered may differ from the serotype(s) causative of the infection, disease or condition;

(xiv) an infection, disease or condition caused by any one or more serotypes of *Streptococcus pneumoniae* by administering one or more photon-irradiated (e.g. gamma-irradiated and/or X-irradiated) serotype(s) of *Streptococcus pneumoniae*. The photon-irradiated *Streptococcus pneumoniae* serotype(s) administered may differ from the serotype(s) causative of the infection, disease or condition;

(xv) an infection, disease or condition caused by any one or more serotypes of *Streptococcus pyogenes* by administering one or more photon-irradiated (e.g. gamma-irradiated and/or X-irradiated) serotype(s) of *Streptococcus pyogenes*. The photon-irradiated *Streptococcus pyogenes* serotype(s) administered may differ from the serotype(s) causative of the infection, disease or condition;

(xvi) an infection, disease or condition caused by any one or more serotypes of *Streptococcus salivarius* by administering one or more photon-irradiated (e.g. gamma-irradiated and/or X-irradiated) serotype(s) of *Streptococcus salivarius*. The photon-irradiated *Streptococcus salivarius* serotype(s) administered may differ from the serotype(s) causative of the infection, disease or condition;

(xvii) an infection, disease or condition caused by any one or more serotypes of *Streptococcus sanguinis* by administering one or more photon-irradiated (e.g. gamma-irradiated and/or X-irradiated) serotype(s) of *Streptococcus sanguinis*. The photon-irradiated *Streptococcus sanguinis* serotype(s) administered may differ from the serotype(s) causative of the infection, disease or condition;

(xviii) an infection, disease or condition caused by any one or more serotypes of *Streptococcus suis* by administering one or more photon-irradiated (e.g. gamma-irradiated and/or X-irradiated) serotype(s) of *Streptococcus suis*. The photon-irradiated *Streptococcus suis* serotype(s) administered may differ from the serotype(s) causative of the infection, disease or condition; and/or (xix) an infection, disease or condition caused by any one or more serotypes of *Streptococcus uberis* by administering one or more photon-irradiated (e.g. gamma-irradiated and/or X-irradiated) serotype(s) of *Streptococcus uberis*. The photon-irradiated *Streptococcus uberis* serotype(s) administered may differ from the serotype(s) causative of the infection, disease or condition.

In some embodiments, the methods are utilised to prevent or treat an infection, disease or condition caused by one or more serotypes of *Streptococcus pneumoniae*. The methods may comprise inducing an immune response in a subject against a plurality of different *S. pneumoniae* serotypes, by administering one or more serotypes of photon-irradiated (e.g. gamma-irradiated and/or X-irradiated) *S. pneumoniae* to the subject. In some embodiments the methods comprise administering a single photon-irradiated (e.g. gamma-irradiated and/or X-irradiated) serotype of *S. pneumoniae*.

In some embodiments, the methods comprise preventing or treating an infection, disease or condition caused by one or more serotypes of *Streptococcus pneumoniae*. The methods comprise administering to a subject at least one serotype of photon-irradiated (e.g. gamma-irradiated and/or X-irradiated) *S. pneumoniae*, and may induce an immune response in the subject against any one or more of *S. pneumoniae* serotypes 1, 2, 3, 4, 5, 6A, 6B, 6C, 6D, 7A, 7B, 7C, 7F, 8, 9A, 9L, 9N, 9V, 10A, 10B, 10C, 10F, 11A, 11B, 11C, 11D, 11F, 12A, 12B, 12F, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 27, 28A, 28F, 29, 31, 32A, 32F, 33A, 33B, 33C, 33D, 33F, 34, 35A, 35B, 35C, 35F, 36, 37, 38, 39, 40, 41A, 41F, 42, 43, 44, 45, 46, 47A, 47F, and/or 48. In some embodiments, the methods may induce an immune response in the subject against any one or more of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F. The photon-irradiated *S. pneumoniae* serotype(s) administered may differ from the serotype(s) causative of the infection, disease or condition.

The disease or condition may be any that is caused by infection of the particular species or serotype of streptococcal bacteria. By way of non-limiting example only, the disease or condition may be any one or more of: pneumonia, ear infection, earache, middle ear infection, otitis media, sinusitis, meningitis, conjunctivitis, bacteraemia, septicaemia, a joint infection, a bone infection, septic arthritis, osteomyelitis, a soft tissue infection, cellulitis, myositis, periorbital cellulitis, an abscess, peritonitis, a cardiac infection, endocarditis, and pericarditis.

The subject may be any animal of economic, social or research importance including bovine, equine, ovine, primate, avian and rodent species. Accordingly, the subject may be a mammal such as, for example, a human or a non-human mammal (e.g. a pig, cat, dog, cow, horse, or sheep). The subject may be a laboratory animal (e.g. a rodent such as a mouse, rat, or guinea pig; a rabbit, and the like), a bird (e.g. poultry), a fish or a crustacean.

The photon-irradiated (e.g. gamma-irradiated and/or X-irradiated) streptococcal bacteria and/or photon-irradiated derivatives thereof may be administered to the subject by any suitable route including, for example, parenteral (e.g. intradermal, intravenous, intraspinal, intraperitoneal, subcutaneous or intramuscular), oral, topical, or mucosal routes (e.g. intranasal). In some embodiments, administration is by the mucosal route. For example, the administration may be intranasal.

Without being limited to specific mechanism(s) of action, the methods may induce an immune response in the subject comprising one or more of the following:

(i) production of antibodies that bind specifically to antigen(s) of the streptococcal bacteria causative of the infection, disease or condition;

(ii) CD4$^+$ T lymphocyte responses specific for antigen(s) of the streptococcal bacteria causative of the infection, disease or condition;

(iii) CD8$^+$ T lymphocyte responses specific for antigen(s) of the streptococcal bacteria causative of the infection, disease or condition.

In some embodiments, the methods may induce an immune response in the subject that may be Interleukin-17A (IL-17A) dependent, IL-17A independent, and/or that comprises activation of the innate immune system including the production of cytokines (e.g. IFN-γ) and/or activation of Toll-like receptors (e.g. TLR-3). This may assist in reducing the activation threshold for B cells and/or enhancing the quality or quantity of antibody responses against antigens of interest.

By way of non-limiting example only, an immune response induced or enhanced in a subject by the method may be increased by at least about 10%, at least about 20%, at least about 25%, at least about 50%, at least about 75%, at least about 90%, at least about two-fold, at least about five-fold, at least about ten-fold, at least about twenty-fold, at least about fifty-fold, or at least about 100-fold, when compared to a suitable control. The suitable control may, for example, be a measurement of the same immune response prior to performing the method under otherwise similar, substantially identical, or identical conditions.

Methods for detecting and quantifying immune response are well known to those of ordinary skill in the field and include, for example, solid-phase heterogeneous assays (e.g. enzyme-linked immunosorbent assay), solution phase assays (e.g. electrochemiluminescence assay), amplified luminescent proximity homogeneous assays, flow cytometry, intracellular cytokine staining, functional T-cell assays, functional B-cell assays, functional monocyte-macrophage assays, dendritic and reticular endothelial cell assays, measurement of NK cell responses, oxidative burst assays, cytotoxic specific cell lysis assays, pentamer binding assays, and phagocytosis and apoptosis evaluation.

Vaccine Formulations

The streptococcal bacteria and their derivatives described herein may be incorporated into pharmaceutical compositions. The compositions can stimulate an immune response against pathogenic organisms capable of establishing infection in a host that may culminate in a disease or condition. Accordingly, the compositions may be vaccines, including preventative vaccines (i.e. vaccines administered for the purpose of preventing infections and/or diseases/conditions) and therapeutic vaccines (i.e. vaccines administered for the purpose of treating infections and/or diseases/conditions). A vaccine of the present invention may therefore be administered to a recipient for prophylactic, ameliorative, palliative, or therapeutic purposes. It will be understood that all such vaccines are collectively encompassed by reference herein to "vaccines of the invention" or a "vaccine of the invention". Non-limiting examples of suitable streptococcal bacteria and their derivatives suitable for incorporation into vaccines of the invention are described above in the subsections entitled "Streptococcal strains" and "Streptococcal derivatives". The streptococcal bacteria and their derivatives of the vaccines are attenuated or inactivated by photon-radiation (e.g. gamma-radiation and/or X-radiation). The photon-radiation may be applied to the bacteria/derivatives before, during or after combining them with other reagent(s) to provide a vaccine formulation.

Formulations

Vaccines of the invention may be prepared using methods known to those of ordinary skill in the art. Non-limiting examples of suitable methods are described in Gennaro et al. (Eds), (1990), "*Remington's Pharmaceutical Sciences*", Mack Publishing Co., Easton, Pa., USA, and methods for vaccine preparation are generally described in Voller et al., (1978), "*New Trends and Developments in Vaccines*", University Park Press, Baltimore, Md., USA.

The vaccines may comprise a pharmaceutically acceptable carrier, excipient, diluent and/or adjuvant. "Pharmaceutically acceptable" carriers, excipients, diluents and/or adjuvants are substances which as contemplated herein are substances which do not produce adverse reaction(s) when administered to a particular recipient such as a human or non-human animal. Pharmaceutically acceptable carriers, excipients, diluents and adjuvants are generally also compatible with other ingredients of the vaccine. Non-limiting examples of suitable excipients, diluents, and carriers can be found in the "*Handbook of Pharmaceutical Excipients*" 4th Edition, (2003) Rowe et al. (Eds), The Pharmaceutical Press, London, American Pharmaceutical Association, Washington.

Non-limiting examples of pharmaceutically acceptable carriers, excipients or diluents include demineralised or distilled water; saline solution; vegetable based oils such as peanut oil, safflower oil, olive oil, cottonseed oil, maize oil, sesame oils, *arachis* oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Vaccines of the present invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, or in a form suitable for parenteral administration, that is, intradermal, subcutaneous, intramuscular or intravenous injection.

Solid forms of the vaccines for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms of the vaccines for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions comprising the vaccines for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

For preparation of the vaccines as injectable solutions or suspensions, non-toxic parenterally acceptable diluents or carriers may be used such as Ringer's solution, isotonic saline, phosphate buffered saline, ethanol and 1,2 propylene glycol.

Vaccine emulsions for oral administration may further comprise one or more emulsifying agents. Suitable emulsifying agents include dispersing agents as exemplified above or natural gums such as guar gum, gum acacia or gum tragacanth.

Topical formulations of the vaccines comprise an active ingredient(s) (e.g. photon-irradiated streptococcal bacteria and/or derivatives thereof) together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

When formulated as drops, the vaccines may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. For example, sterilisation may be achieved by filtration followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

When formulated as lotions, the vaccines include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

When formulated as creams, ointments or pastes, the vaccines may be semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The vaccines may include any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The vaccines may be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The vaccines in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq.

Adjuvants

Adjuvant(s) may be included in vaccines of the invention, although experimental data provided herein demonstrates that photon-irradiated streptococcal bacteria and their derivatives can induce immunity without requiring such adjuvants. Accordingly, vaccines of the invention may or may not comprise an adjuvant.

In general, adjuvant activity in the context of a vaccine composition includes, but is not limited to, the ability to enhance the immune response (quantitatively or qualitatively) induced by immunogenic components in the vaccine (e.g. photon-irradiated streptococcal bacteria and/or derivatives thereof). This may reduce the dose or level of the immunogenic components required to produce an immune response and/or reduce the number or the frequency of immunisations required to produce the desired immune response.

Preferably, an adjuvant will enhance the immune response induced and/or enhanced by component(s) of the vaccine thereby improving protective efficacy. Preferably, the adjuvant will enable the induction of protective immunity utilising a lower dose of other active component(s) (e.g. photon-irradiated streptococcal bacteria and/or derivatives thereof).

Non-limiting examples of adjuvants suitable for inclusion in vaccines of the invention and methods for their preparation are described in "*Vaccine Adjuvants: Preparation Methods and Research Protocols (Methods in Molecular Medicine)*", (2000), Ohagan (Ed), Humana Press Inc. Any suitable adjuvant may be included in a vaccine of the invention.

Specific examples of such adjuvants include, but are not limited to, aluminium hydroxide; polypeptide adjuvants including interferons, interleukins, and other cytokines; AMPHIGEN, oil-in-water and water-in-oil emulsions; and saponins such as QuilA.

For example, an aluminium-based adjuvant may be utilised. Suitable aluminium-based adjuvants include, but are not limited to, aluminium hydroxide, aluminium phosphate and combinations thereof. Other specific examples of aluminium-based adjuvants that may be utilised are described in European Patent No. 1216053 and U.S. Pat. No. 6,372,223.

Oil in water emulsions may be utilised as adjuvants in vaccines of the invention. Oil in water emulsions are well known in the art. In general, the oil in water emulsion will comprise a metabolisable oil, for example, a fish oil, a vegetable oil, or a synthetic oil. Examples of suitable oil in water emulsions include those described in European Patent No. 0399843, U.S. Pat. No. 7,029,678 and PCT Publication No. WO 2007/006939. The oil in water emulsion may be utilised in combination with other adjuvants and/or immunostimulants.

Non-limiting examples of other suitable adjuvants include immunostimulants such as granulocyte-macrophage colony-stimulating factor (GM-CSF), monophosphoryl lipid A (MPL), cholera toxin (CT) or its constituent subunit, heat labile enterotoxin (LT) or its constituent subunit, toll-like receptor ligand adjuvants such as lipopolysaccharide (LPS) and derivatives thereof (e.g. monophosphoryl lipid A and 3-Deacylated monophosphoryl lipid A), muramyl dipeptide (MDP), Toll-like receptor (TLR) agonists (e.g. TLR-2, TLR-3 agonists) and F protein of Respiratory Syncytial Virus (RSV).

Adjuvants in vaccines of the invention may typically include emollients, emulsifiers, thickening agents, preservatives, bactericides and buffering agents. Another type of "self adjuvant" is provided by the conjugation of immunogenic peptides to lipids such as the water soluble lipopeptides Pam3Cys or its dipalmitoyl derivative Pam2Cys. Such adjuvants have the advantage of accompanying and immunogenic component into the antigen presenting cell (such as dendritic cells) and thus producing enhanced antigen presentation and activation of the cell at the same time (see, for example, Brown and Jackson, (2005), "*Lipid based self adjuvanting vaccines*", Current Drug Delivery, 23:83).

Suitable adjuvants are commercially available such as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminium salts such as aluminium hydroxide gel (alum) or aluminium phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

In certain embodiments, an adjuvant included in a vaccine of the invention may induce an immune response predominantly of the TH1 type. Suitable adjuvants for use in eliciting a predominantly TH1-type response include, for example, a combination of monophosphoryl lipid A, preferably 3-de-O-acylated monophosphoryl lipid A (3D-MPL) together with an aluminium salt. For example, the composition or vaccine may be formulated with adjuvant AS04 containing aluminium hydroxide (alum) and 3-O-deacylated monophosphorylated lipid A (MPL) such as described in Thoelen et al. (2001), "*A prophylactic hepatitis B vaccine with a novel adjuvant system*", Vaccine, 19:2400-2403. Other known adjuvants, which preferentially induce a TH1 type immune response, include CpG containing oligonucleotides. The oligonucleotides are characterised in that the CpG dinucleotide is unmethylated. Such oligonucleotides are known to those of ordinary skill in the field and are described, for example, in PCT Publication No. WO 1996/02555. Immunostimulatory DNA sequences are also described, for example, in Sato et al., (1996), "*Immunostimulatory DNA sequences necessary for effective intradermal gene immunization*", Science, 273:352-354.

Another example of an adjuvant is a saponin, preferably QS21 (Aquila Biopharmaceuticals Inc., Framingham, Mass.), which may be used alone or in combination with other adjuvants. For example, an enhanced adjuvant system may be utilised involving the combination of a monophosphoryl lipid A and saponin derivative, such as the combination of QS21 and 3D-MPL as described in PCT Publication No. WO 1994/00153, or a less reactogenic composition where the QS21 is quenched with cholesterol, as described in PCT publication No. WO 1996/33739. Other alternative formulations comprise an oil-in-water emulsion and tocopherol. An adjuvant formulation involving QS21, 3D-MPL and tocopherol in an oil-in-water emulsion is described in PCT Publication No. WO 1995/17210. An adjuvant included in a composition of the invention may include a formulation involving QS21, 3D-MPL and tocopherol in an oil in water emulsion such as described in PCT publication No. WO 1995/17210. In one embodiment a composition of the invention comprises the adjuvant Montanide ISA720 (M-ISA-720; Seppic, Fairfield, N.J.), an adjuvant based on a natural metabolisable oil.

Preferably, the adjuvant is a mucosal adjuvant effective in enhancing mucosal immunity and/or systemic immunity to immunogenic components administered via the mucosal route. Mucosal adjuvants may be broadly classified as those that facilitate vaccine delivery (e.g. liposomes, cochleates, live-attenuated vectors, poly D,L-lactide-co-glycolide or PLGA, chitans, DNA vaccines, mucoadhesives) to enhance the induction of protective immunity induced by other immunogenic components of the vaccine, and those having an immunostimulatory role (e.g. innate immunity associated toxin-based, cytokine-based etc.). Without limitation to a particular mechanism, it is postulated that the advantageous effects of mucosal adjuvants partially derive from an ability to assist the passage of immunogenic components in the vaccine across the mucosal barrier. Upon traversing the mucosal barrier, the mucosal adjuvant may enhance immunity, for example, by complement activation, the induction of cytokines, stimulation of antibody production or antibody type switching, stimulating antigen presenting cells, and/or influencing MHC class I and/or class II expression.

Routes of Administration

Vaccines of the invention may be administered to a recipient by standard routes, including, but not limited to, parenteral (e.g. intradermal, intravenous, intraspinal, intraperitoneal, subcutaneous or intramuscular), oral, topical, or mucosal routes (e.g. intranasal).

For example, the vaccines may be administered by a mucosal route. Non-limiting examples of acceptable routes of mucosal vaccine administration including intranasal, ocular, buccal, genital tract (vaginal), rectal, intratracheal, skin, and the gastrointestinal tract.

In some embodiments, vaccines of the invention are administered by the intranasal route. Without limitation to theory or particular mode(s) of action, intranasal administration of the vaccines may be advantageous for enhancing immunity against certain streptococcal infections in which bacteria infect the host via mucosal surfaces of the upper and/or lower respiratory tracts. In addition, mucosal vaccination (e.g. intranasal vaccination) may induce mucosal immunity not only in the respiratory tracts but also in distant mucosal sites including the genital mucosa.

Intranasal vaccines of the invention can be formulated, for example, in liquid form as nose drops, spray, or suitable for inhalation, as powder, as cream, or as emulsion. Nebulised or aerosolised intranasal vaccines may also be utilised. Administration of vaccines to mucosa of the upper and/or lower respiratory tract via inhalation of mists, powders, or sprays, or by intranasal administration of nose drops, swabs, powders, sprays, mists, aerosols, and the like is also contemplated.

In one embodiment, the vaccines for intranasal administration are provided in a freeze-dried powder form capable of re-constitution immediately prior to use. Powder vaccine formulations of vaccines and compositions of the present invention provide a means of overcoming refrigerated storage and distribution requirements associated with liquid-based vaccine stability and delivery. Dry powder formulations offer the advantage of being more stable and also do not support microbial growth.

The freeze-dried vaccines may induce levels of heterosubtypic immunity similar to that of non freeze-dried vaccines. The vaccines may be freeze-dried using any suitable technique known in the art. For example, liquid preparations of photon-irradiated streptococcal bacteria and/or derivatives thereof may be frozen in a dry ice—isopropanol slurry and lyophilized in a freeze Dryer (e.g. Virtis Model 10-324 Bench, Gardiner, N.Y.) for a suitable time period (e.g. 24 hours).

In one embodiment, a dry powder nasal vaccine of the invention is produced by generating spray-freeze-drying (SFD) particles (see, for example, Costantino et al., (2002), "*Protein spray freeze drying. 2. Effect of formulation variables on particle size and stability*", J Pharm Sci., 91:388-395; Costantino, et al., (2000), "*Protein spray-freeze drying. Effect of atomization conditions on particle size and stability*", Pharm Res., 17:1374-1383; Maa et al., (1999), "*Protein inhalation powders: spray drying vs spray freeze drying*", Pharm Res, 16:249-254; Carrasquillo et al., (2001); "*Non-aqueous encapsulation of excipient-stabilized spray-freeze dried BSA into poly(lactide-co-glycolide) microspheres results in release of native protein*", J Control Release, 76:199-208; Carrasquillo et al., (2001), "*Reduction of structural perturbations in bovine serum albumin by non-aqueous microencapsulation*", J Pharm Pharmacol., 53:115-120; and U.S. Pat. No. 6,569,458).

Preferred devices for intranasal administration of the vaccines are nasal spray devices (e.g. devices available commercially from Pfeiffer GmBH, Valois and Becton Dickinson). Non-limiting examples of suitable devices are described, for example, in Bommer, (1999), "*Advances in Nasal drug delivery Technology*", Pharmaceutical Technology Europe, p 26-33. Intranasal devices may produce droplets in the range 1 to 500 μm. Preferably, only a small percentage of droplets (e.g. <5%) are below 10 μm to minimise the chance of inhalation. Intranasal devices may be capable of bi-dose delivery, that is, the delivery of two subdoses of a single vaccination dose, one sub-dose to each nostril.

A vaccine of the invention may be administered to a recipient in isolation or in combination with other additional therapeutic agent(s). In embodiments where the vaccine is administered with therapeutic agent(s), the administration may be simultaneous or sequential (i.e. vaccine administration followed by administration of the agent(s) or vice versa). Thus, where a vaccine of the invention is administered to a subject in conjunction with another agent, both may be administered in a single composition at the same time, in separate compositions at the same time, or separately at different times.

Dosages

In general, vaccines of the invention are administered in a manner compatible with the route of administration and physical characteristics of the recipient (including health status) and in such a way that it is elicits the desired effect(s) (i.e. therapeutically effective, immunogenic and/or protective).

For example, the appropriate dosage of a given vaccine may depend on a variety of factors including, but not limited to, a subject's physical characteristics (e.g. age, weight, sex), whether the compound is being used as single agent or adjuvant therapy, the progression (i.e. pathological state) of a given streptococcal infection, and other factors that may be recognized by one skilled in the art. Various general considerations that may be considered when determining an appropriate dosage of a given vaccine of the invention are described, for example, in Gennaro et al. (Eds), (1990), "*Remington's Pharmaceutical Sciences*", Mack Publishing Co., Easton, Pa., USA; and Gilman et al., (Eds), (1990), "*Goodman And Gilman's: The Pharmacological Bases of Therapeutics*", Pergamon Press.

In general, vaccines of the invention may be administered to a patient in an amount of from about 50 micrograms to about 5 mg of active component(s) (i.e. photon-irradiated streptococcal bacteria and/or derivatives thereof). Dosage in an amount of from about 50 micrograms to about 500 micrograms is especially preferred.

One skilled in the art would be able, by routine experimentation, to determine an effective, non-toxic amount of photon-irradiated streptococcal bacteria or derivatives thereof to include in a vaccine of the invention for the desired therapeutic outcome.

Generally, an effective dosage is expected to be in the range of about 0.0001 mg to about 1000 mg of active component(s) (i.e. photon-irradiated streptococcal bacteria or derivatives thereof) per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$ of active component(s) (i.e. photon-irradiated streptococcal bacteria or derivatives thereof). Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

Typically, in therapeutic applications, the treatment would be for the duration of the infection, disease state or condition. Further, it will be apparent to one of ordinary skill in the art that the optimal quantity and spacing of individual dosages will be determined by the nature and extent of the infection, disease state or condition being treated, the form, route and site of administration, and the nature of the particular individual being treated. Also, such optimum conditions can be determined by conventional techniques.

In many instances, it will be desirable to have several or multiple administrations of a vaccine of present invention. For example, vaccines of the invention may be administered 1, 2, 3, 4, 5, 6, 7, 8, 9, 10, or more times. The administrations may be from about one to about twelve week intervals, and in certain embodiments from about one to about four week intervals. Periodic re-administration may be desirable in the case of recurrent exposure to a particular pathogen targeted by a vaccine of the invention.

It will also be apparent to one of ordinary skill in the art that the optimal course of treatment can be ascertained using conventional course of treatment determination tests.

The methods described herein may comprise administering a priming dose of a vaccine of the invention. The priming dose may be followed by a booster dose. The booster may be for the purpose of revaccination. In various embodiments, the vaccine is administered at least once, twice, three times or more. Vaccines of the invention may be administered to naïve recipients, being individuals seronegative for particular target strain(s) of streptococcal bacteria. Alternatively, the vaccines may be administered to primed recipients, being individuals seropositive for particular target strain(s) of streptococcal bacteria.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

EXAMPLES

The present invention will now be described with reference to specific Example(s), which should not be construed as in any way limiting.

Example One: Generation of a Pneumococcal Strain Suitable for Testing as a Universal Vaccine

*Streptococcus pneumoniae* strain Rx1 is a derivative of serotype 2 (D39), which lacks the outer capsule of the bacterium. This strain was genetically modified to remove the autolysin gene (lytA) as shown in the flow chart of FIG. 22. The resultant Rx1 (ΔLytA) strain was further modified by replacing the pneumolysin gene (ply) with a toxoid version of Ply, designated as PdT, as shown in the flow chart of FIG. 22.

Figure 1:
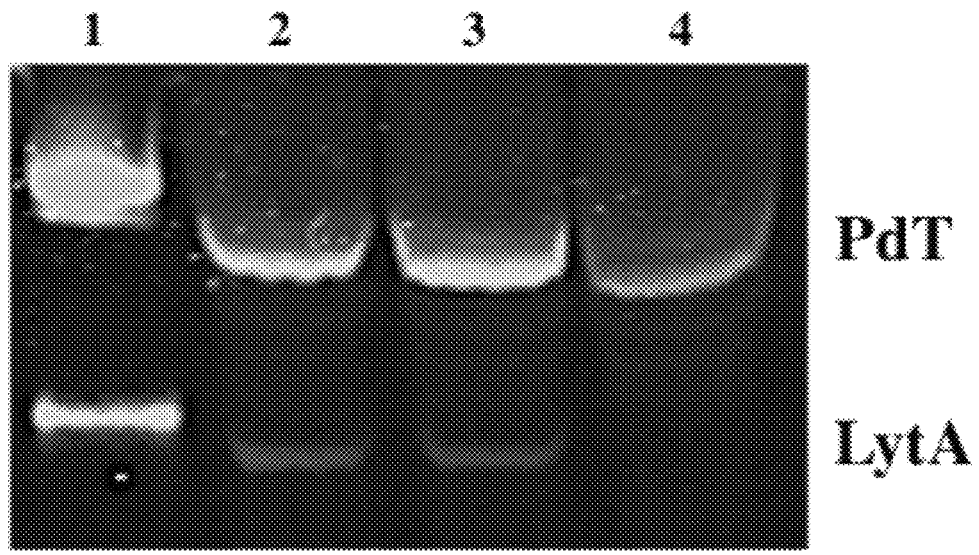
FIG. 1 shows the results of Western blot analysis detecting PdT and LytA in *S. pneumoniae* D39 and various derivatives using anti-LytA and anti-PdT antisera. This confirms the successful deletion of the lytA gene and the substitution of ply with the mutant gene coding for PdT, leading to the generation of a lytA null mutant (autolysin-deficient), pneumolysin mutant derivative (PdT) Rx1 strain, designated *S. pneumoniae* Rx1 (ΔLytA, PdT). Lanes: 1. Purified Ply and LytA (5 ng each) as a control; 2. *S. pneumoniae* D39; 3, *S. pneumoniae* Rx1; 4, Rx1 (ΔLytA, PdT) vaccine strain (pre-irradiation). The recombinant purified Ply and LytA proteins are larger in size due to the presence of a His6-tag.

PCR and Western blot were performed after each transformation step to further confirm successful transformations, and sequencing confirmed the successful generation of a lytA deficient, pneumolysin mutant (PdT) Rx1 strain, designated *S. pneumoniae* Rx1 (ΔLytA, PdT) (FIG. 1).

Figure 2:
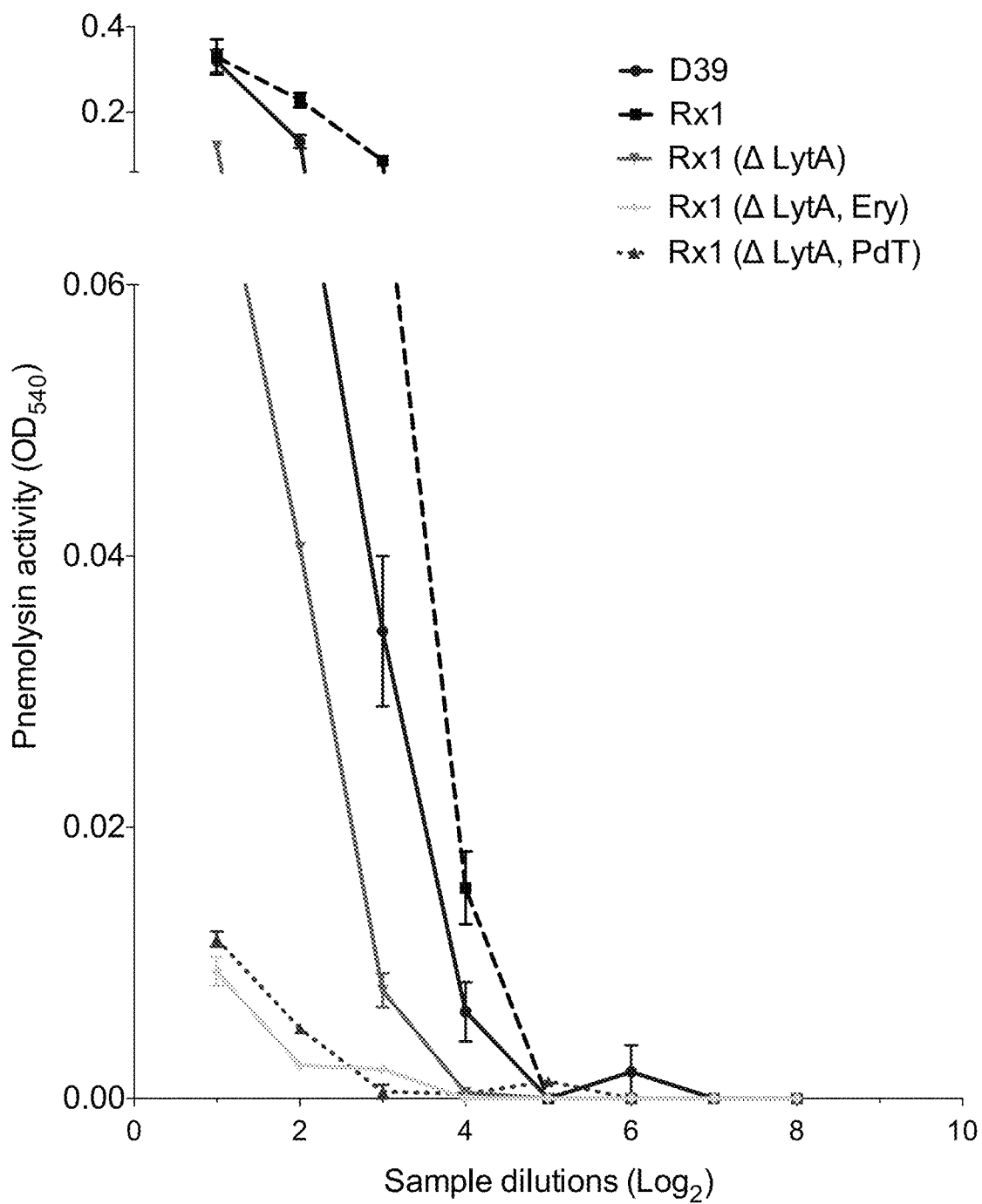
FIG. 2 shows the results of a haemolytic assay performed to confirm the lack of haemolytic activity in the derivative Rx1 strain *S. pneumoniae* Rx1 (ΔLytA, PdT) carrying the PdT mutant form of pneumolysin.

A haemolytic assay was performed on each derivative to confirm the lack of haemolytic activity in the derivative strain carrying the PdT mutant form of pneumolysin (FIG. 2).

Western blot, PCR and sequencing thus confirmed the successful generation of *Streptococcus pneumoniae* strain *S. pneumoniae* Rx1 (ΔLytA, PdT).

Example Two: Secondary Structure Analysis of mRNA Transcript from the ΔlytA Gene Analyses were performed to predict the secondary structure of the ΔlytA gene mRNA transcript.

The DNA sequence of the lytA gene of strain Rx1, prior to deletion, including flanking regions, is shown in SEQ ID NO: 1 (FIG. 23). The entire coding region of the lytA gene from the ATG (start codon) through to the TAA (stop codon) was deleted, in-frame, by splice-overlap extension PCR. The resultant ΔlytA gene sequence is shown in SEQ ID NO: 2 (FIG. 24A). The mRNA transcript coded by the ΔlytA gene sequence is shown in SEQ ID NO: 3 (FIG. 24B).

Figure 3:
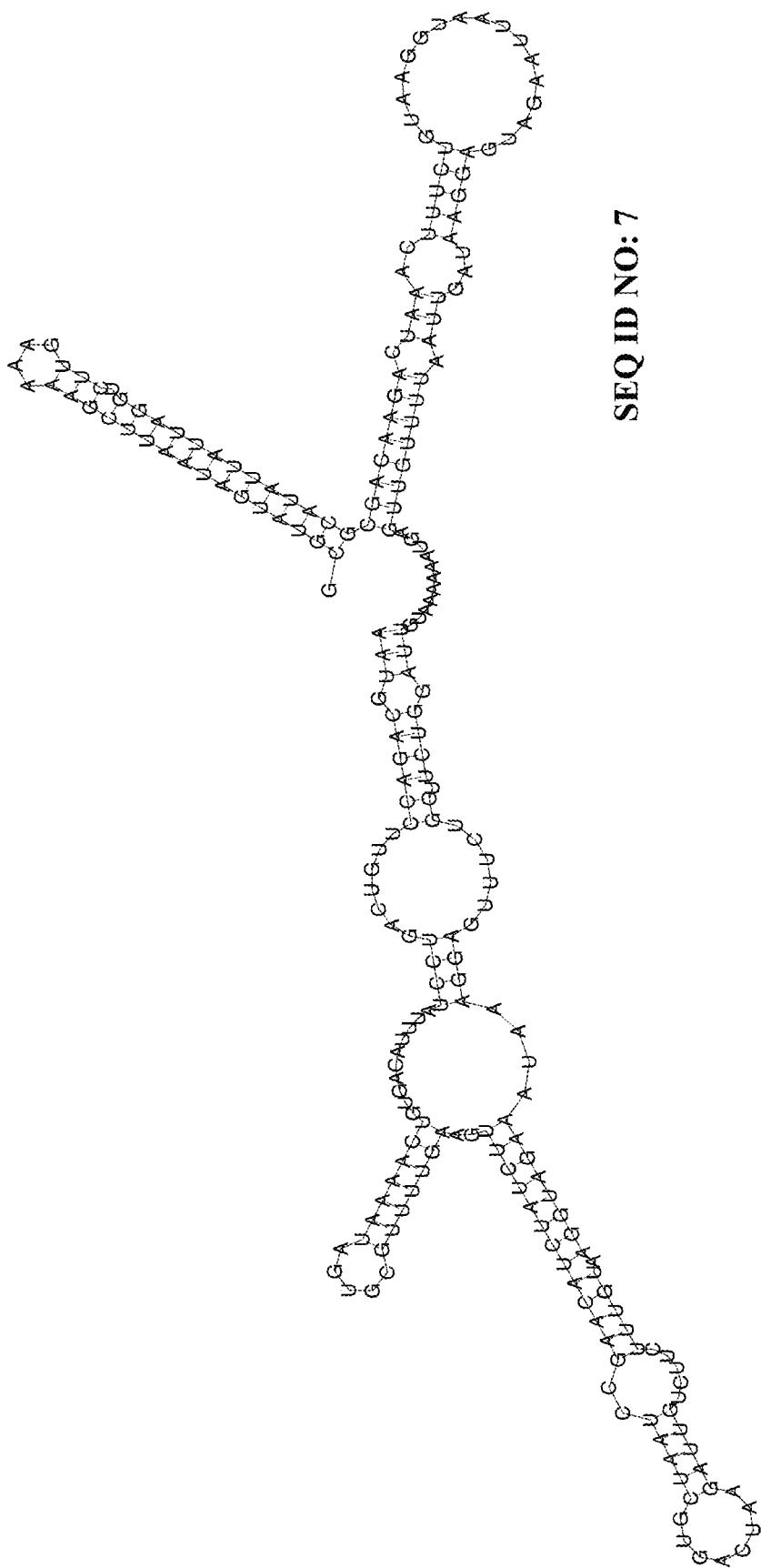
FIG. 3 shows the predicted secondary structure of the mRNA transcript encoded by the ΔlytA gene.

The secondary structure of the mRNA transcript was predicted using RNAfold (RNAfold WebServer ([http://rna.tbi.univie.ac.at/cgi-bin/RNAfold.cgi]) and is shown in FIG. 3. The predicted secondary structure of the mRNA transcript shown in FIG. 3 is anticipated to have a minimum free energy of -52.80 kcal/mol. The predicted double-stranded termination stem-loop sequence shown underlined in black, bold in SEQ ID NO: 3 is predicted to have a minimum free energy of -18.10 kcal/mol.

The lytA coding sequence for autolysin (LytA) is shown in italic/underline with the ATG start codon and TAA stop codon highlighted in bold/italics. The −35 and −10 and sigma70 promoter recognition sequences are shaded in light and dark grey, respectively. Squared/unbold nucleotides denote a potential transcription binding site(s) (TFBs) for RpoD. The bold A in the middle of the TFBs represent a predicted Transcription Start Site (TSS) position for the lytA mRNA. The upstream and downstream nucleotides that immediately flank the ATG start codon and TAA stop codon are squared/bold.

The entire coding region of the lytA gene was deleted, in-frame, by slice-overlap extension PCR, such that the squared/bold nucleotide sequences in SEQ ID NO: 1 upstream and downstream of lytA are fused together.

Example Three: Effect of Gamma-Irradiation Doses and Conditions on the Viability and Morphology of *S. pneumoniae* Rx1 (ΔLytA, PdT)

The effect of gamma-irradiation on the viability and morphology of concentrated vaccine samples at different irradiation doses and conditions was tested.

Figures 4A, 4B:
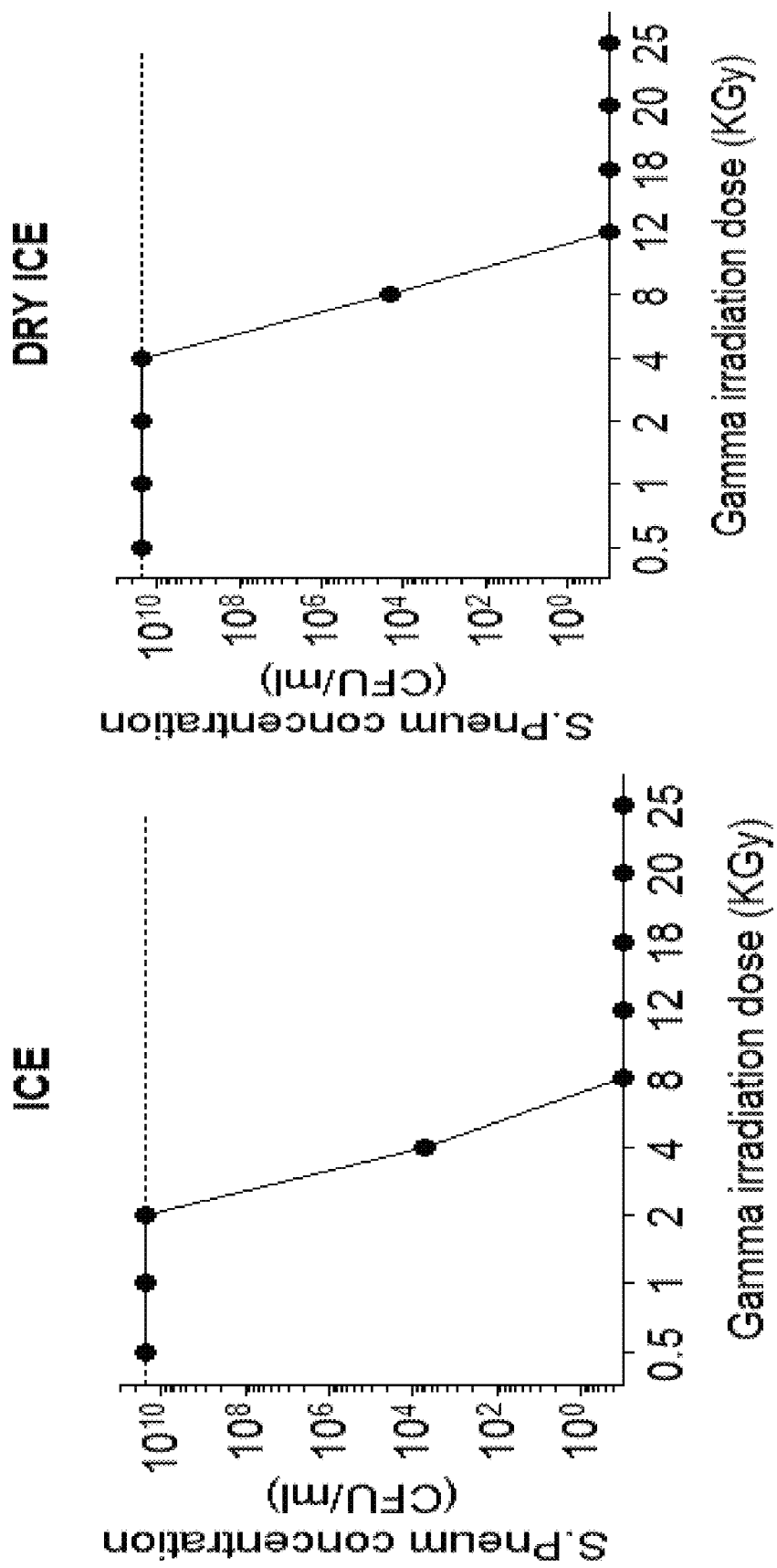
FIG. 4 provides graphs depicting *S. pneumoniae* Rx1 (ΔLytA, PdT) viability following exposure to various dosages of gamma-irradiation on ice (FIG. 4A) or dry ice (FIG. 4B)
Figure 5:
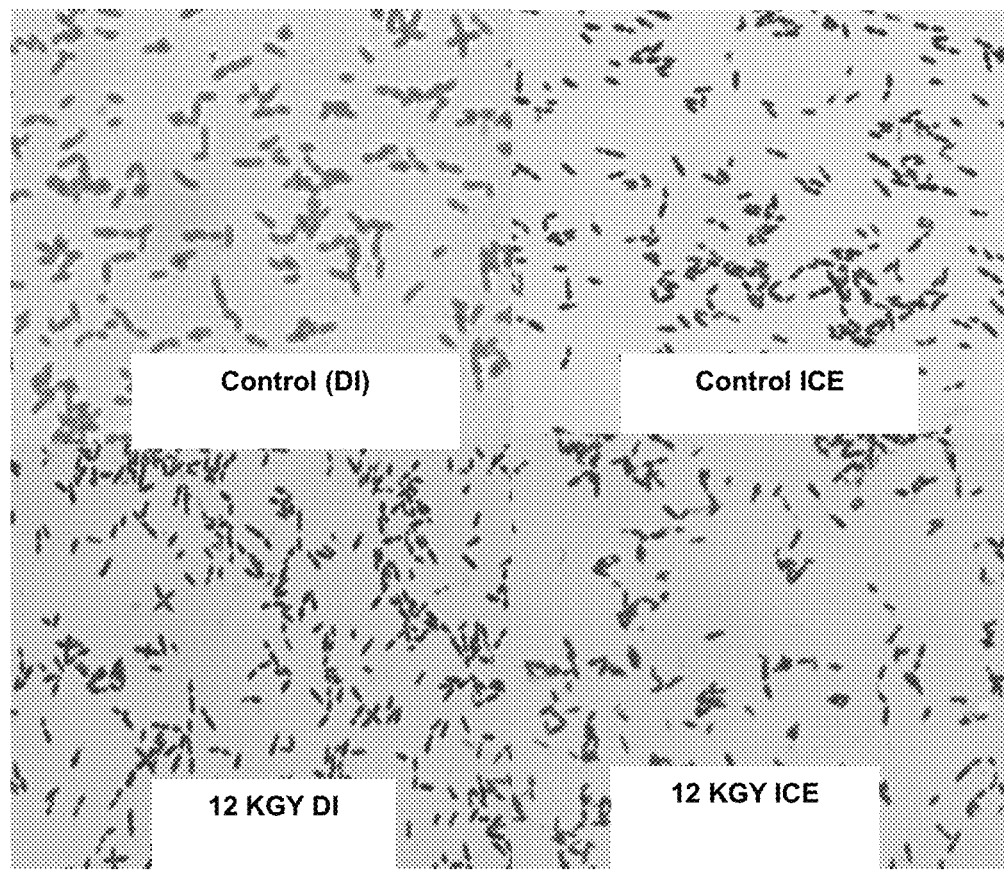
FIG. 5 provides images of gram-stained *S. pneumoniae* Rx1 (ΔLytA, PdT) indicative of the effect of gamma-irradiation on physical morphology. DI: dry ice; KGY: kilogray.
Figure 6:
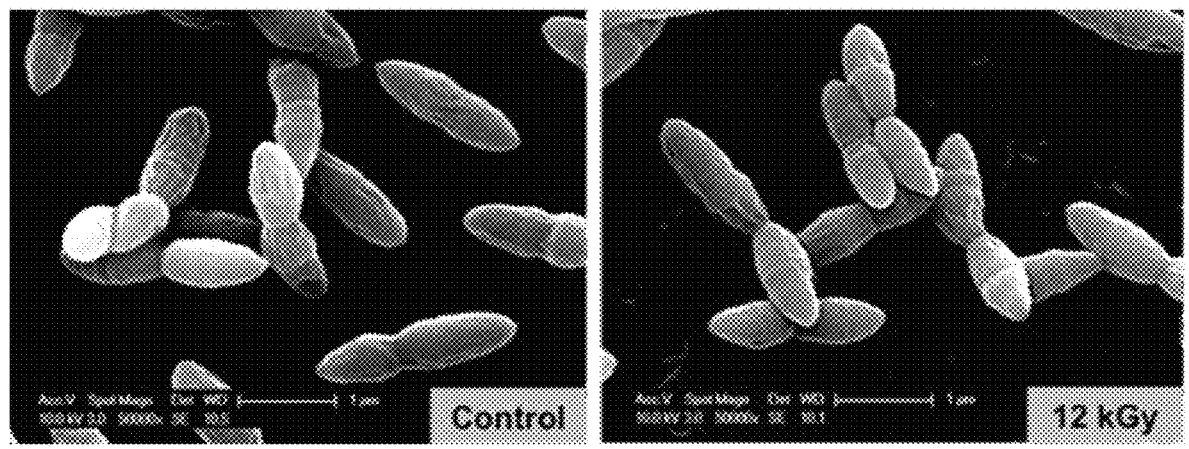
FIG. 6 provides scanning electron microscopy images of *S. pneumoniae* Rx1 (ΔLytA, PdT) indicative of the effect of gamma-irradiation on physical morphology.

*S. pneumoniae* Rx1 (ΔLytA, PdT) was cultured in THY broth to obtain a cell density of $10^8$ colony forming units (CFU)/ml. The bacteria were concentrated via centrifugation, washed with PBS, re-centrifuged and resuspended in PBS-10% glycerol at a final concentration of $1\times10^{10}$ CFU/ml. The stock *S. pneumoniae* Rx1 (ΔLytA, PdT) ($1\times10^{10}$ CFU/ml) was gamma-irradiated at various doses of irradiation (0.5-25 kGy) and temperature conditions, on ice or dry ice (DI). Post gamma-irradiation, samples of the vaccine were plated out onto blood agar plates to assess viability and confirm inactivation (FIG. 4A and FIG. 4B). The Gram stain and scanning electron microscopy were performed to determine the effect of gamma-irradiation on the physical morphology of the bacteria (FIG. 5 and FIG. 6, respectively).

Gamma-irradiation did not affect the morphology of the bacteria. Left hand image shows un-irradiated control bacteria whereas the right hand image shows the morphology of bacteria after irradiation at 12 kGy, which is the minimum dose required for complete inactivation of the sample irradiated on dry ice.

Example Four: Duration of Survival in Mice Vaccinated with Gamma-Irradiated *S. pneumoniae* Rx1 (ΔLytA, PdT) Following Challenge with Live *Streptococcus pneumoniae* Strain D39

Experiments were performed to determine if gamma-irradiated Rx1 (ΔLytA, PdT prepared using gamma-irradiation at 12KGY on DI is able to confer protection against a lethal challenge with live *Steptococcccus pneumoniae* strain D39 (serotype 2).

Mice were vaccinated intranasally with two doses of gamma-irradiated *S. pneumoniae* Rx1 (ΔLytA, PdT) (12 KGY DI) ($1\times10^8$ CFU/dose) at a two week interval. Two weeks after the second vaccination dose, mice were challenged with $1\times10^6$ CFU of *Steptococccus pneumoniae* D39 and monitored for time of survival and percent survival over a period of 21 days (FIG. 7A and FIG. 7B).

The vaccine was able to provide significant protection against lethal challenge with *Steptococccus pneumoniae* D39. Gamma-irradiated *S. pneumoniae* Rx1 (ΔLytA, PdT) was thus observed to afford protection against intranasal challenge with live *Streptococcus pneumoniae* strain D39.

Example Five: Immunity in Mice Vaccinated with *S. pneumoniae* Rx1 (ΔLytA, PdT) Following Heterotypic Challenge with Either *Streptococcus pneumoniae* Strains EF3030 (Serotype 19F) or P9 (Serotype 6A)

Figure 8C:
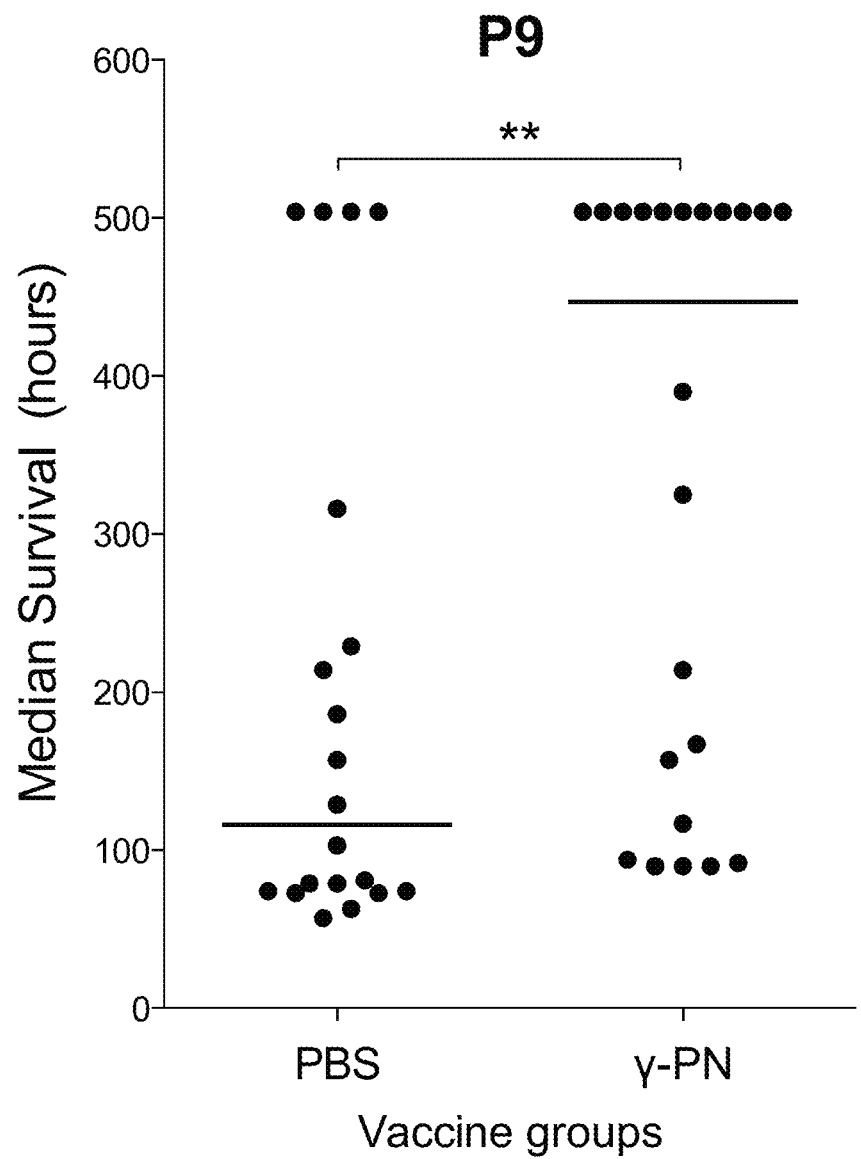
FIG. 8C shows the duration of survival in mice 21 days post challenge with P9. γ-PN=gamma-irradiated *S. pneumoniae* Rx1 (ΔLytA, PdT)

To determine if gamma-irradiated *S. pneumoniae* Rx1 (ΔLytA, PdT) (12KGY DI) is able to confer protection against heterotypic challenge with EF3030 (serotype 19F) or P9 (serotype 6A), mice were vaccinated intranasally with two doses of *S. pneumoniae* Rx1 (ΔLytA, PdT) (12 KGY DI) ($1\times10^8$ CFU/dose). Two weeks after the second vaccination dose, mice were infected with $1\times10^7$ CFU of EF3030 or $5\times10^6$ CFU of P9. Following EF3030 challenge, 96 hours post infection, the lungs and nasopharynx were harvested to determine bacterial counts (see FIG. 8A and FIG. 8B, respectively). Following P9 challenge, mice were monitored for survival for 21 days (FIG. 8C).

The vaccine was able to provide protection against heterotypic challenge as shown by a significant decrease in *S. pneumoniae* EF3030 counts in the lungs and a significant difference in median survival following *S. pneumoniae* P9 challenge.

Example Six: Induction of *S. pneumoniae*-Specific Serum Antibody Responses in Mice Intranasally Vaccinated with *S. pneumoniae* Rx1 (ΔLytA, PdT)

Analyses were conducted to determine whether gamma-irradiated *S. pneumoniae* Rx1 (ΔLytA, PdT) (12KGY DI) is able to induce *S. pneumoniae*-specific antibody responses following intranasal vaccination.

Mice were vaccinated intranasally with two doses of gamma-irradiated *S. pneumoniae* Rx1 (ΔLytA, PdT) (12 KGY DI) ($1\times10^8$ CFU/dose) and blood was collected two weeks after the second vaccination dose. ELISA was conducted to determine antigen specific IgG responses in the serum for the following antigens: Ply, NanA, CbpA and GlpO. In addition, ELISA was used to determine the IgG and IgA antibody responses to PspA and to un-irradiated whole Rx1 (ΔLytA, PdT) bacterial cells.

Figure 9:
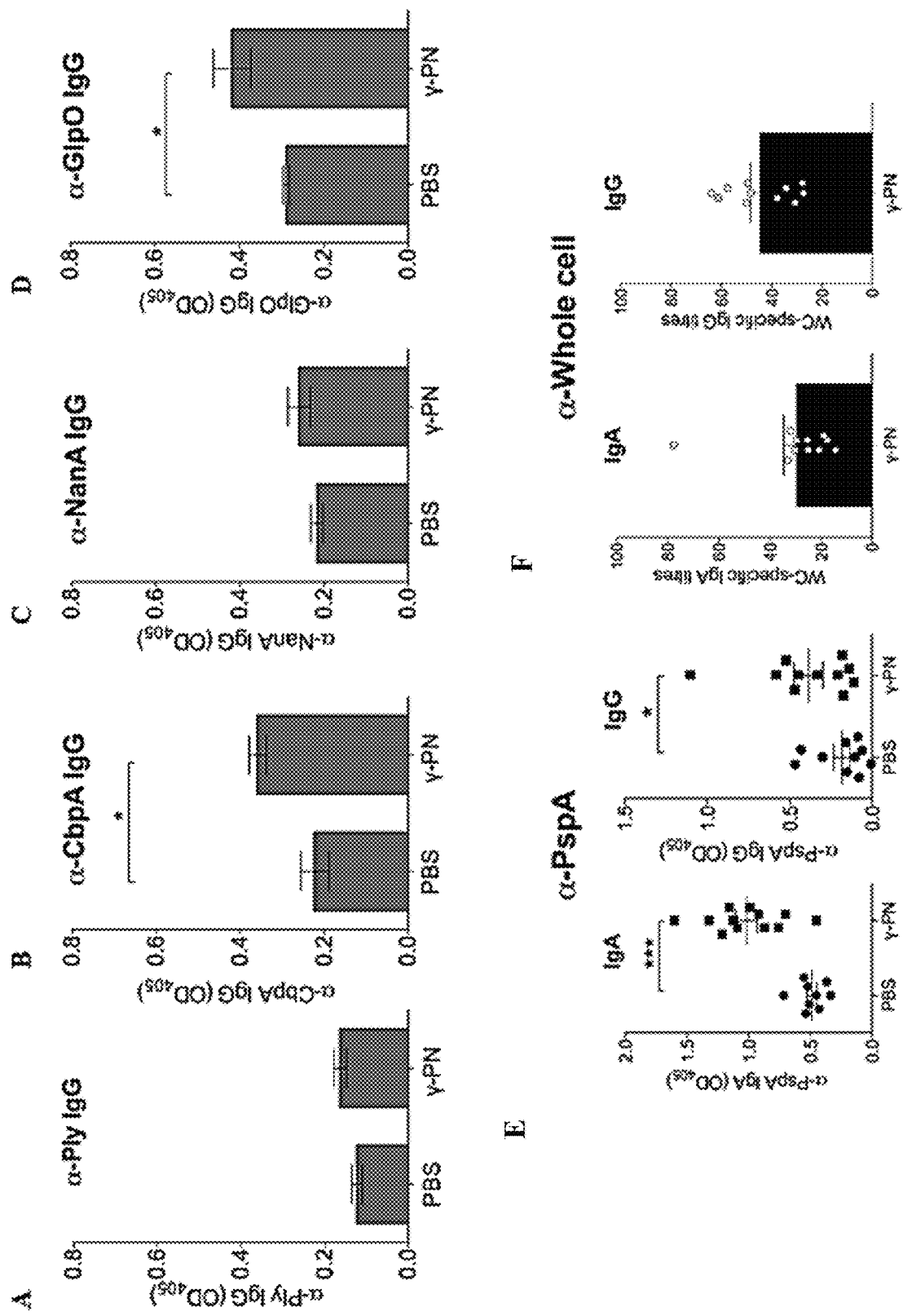
FIG. 9 provides a series of graphs showing the results of ELISAs measuring *S. pneumoniae*-specific antibody responses in mice vaccinated intranasally with gamma-irradiated *S. pneumoniae* Rx1 (ΔLytA, PdT). Individual graphs show specific IgG responses in serum for antigens Ply, CbpA, GlpO and NanA; and IgG and IgA antibody responses to PspA and to un-irradiated whole Rx1 (ΔLytA, PdT) bacterial cells. Mice were vaccinated with γ-PN (gamma-irradiated *S. pneumoniae* Rx1 (ΔLytA, PdT)) or were unvaccinated (PBS control)

There were detectable antibody responses to CbpA, GlpO, PspA and to the whole pneumococcus following intranasal vaccination with gamma-irradiated *S. pneumoniae* Rx1 (ΔLytA, PdT) (FIG. 9).

Example Seven: Induction of *S. pneumoniae* Specific Antibody Responses in Mice Vaccinated with *S. pneumoniae* Rx1 (ΔLytA, PdT) Intraperitoneally Further experiments were conducted to determine if intraperitoneal vaccination is able to induce high-level *Streptococcus pneumoniae*-specific antibody responses.

Figures 10A, 10B, 10C:
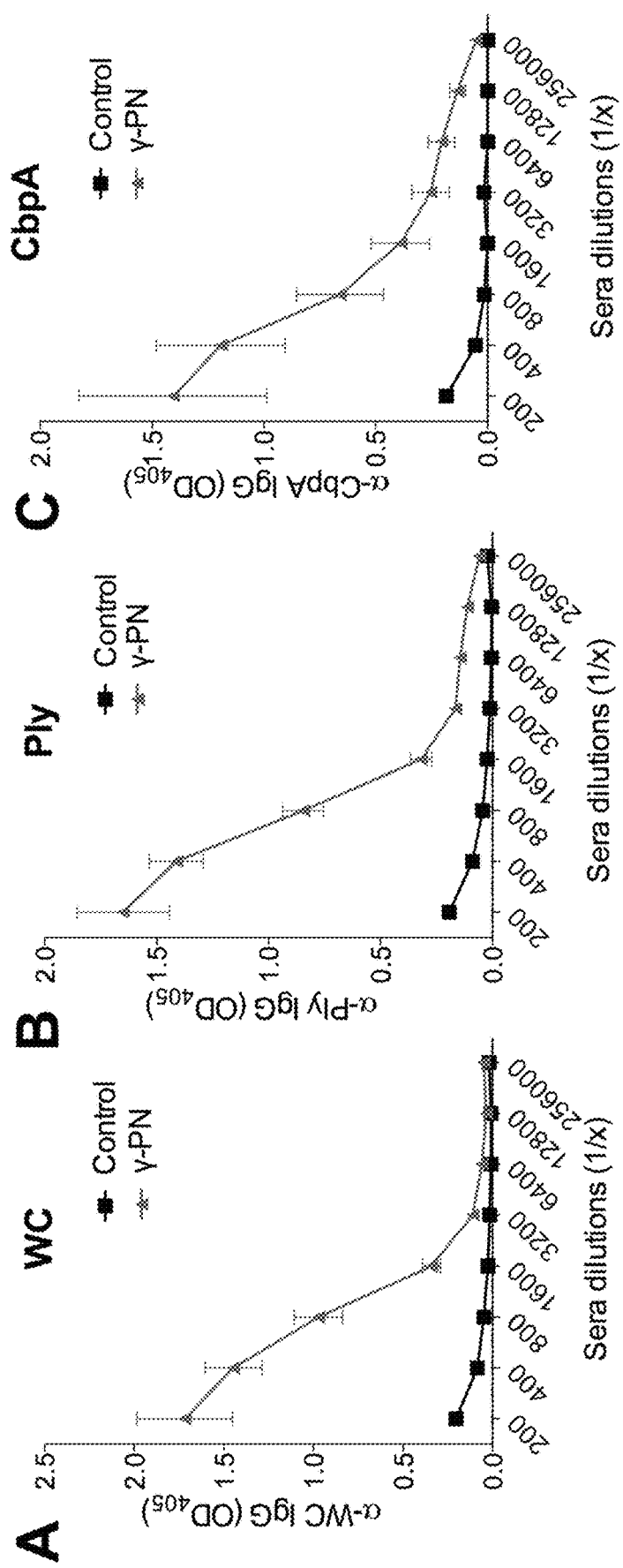
FIG. 10 provides a series of graphs showing the results of ELISAs measuring *S. pneumoniae*-specific antibody responses in mice vaccinated intraperitoneally with gamma-irradiated *S. pneumoniae* Rx1 (ΔLytA, PdT). Individual graphs show specific IgG titres in serum against a whole cell lysate of *S. pneumoniae* Rx1 (ΔLytA, PdT) cells (WC) (FIG.

Mice were vaccinated intraperitoneally with two doses of gamma-irradiated *S. pneumoniae* Rx1 (ΔLytA, PdT) (12 KGY DI) ($1 \times 10^8$ CFU/dose) and blood was collected two weeks after the second vaccination dose. ELISA was used to determine antigen specific IgG titres in the serum for the following antigens: a whole cell lysate of *Streptococcus pneumoniae* Rx1 (ΔLytA, PdT) cells (WC) (FIG. 10A), Ply (FIG. 10B) and CbpA (FIG. 10C).

The vaccine induced significant high-level antibody titres when injected intraperitoneally.

Example Eight: Role of B Lymphocytes in Protective Immunity Induced by Intranasally Administered *S. pneumoniae* Rx1 (ΔLytA, PdT)

The involvement of B-cells in immune responses induced by *S. pneumoniae* Rx1 (ΔLytA, PdT) was assessed.

Wild-type C57BL/6 mice (WT) and B-cell deficient C57BL/6 (μMT) mice (that are B-cell deficient) were vaccinated intranasally with two doses of gamma-irradiated *S. pneumoniae* Rx1 (ΔLytA, PdT) (12 KGY DI) ($1 \times 10^8$ CFU/dose). Two weeks after the second vaccination dose the mice were challenged intranasally with a lethal dose of *Streptococcus pneumoniae* D39 and survival was monitored for 21 days. Percentage survival is shown in FIG. 11.

Vaccination of WT mice with gamma-irradiated *S. pneumoniae* Rx1 (ΔLytA, PdT) resulted in significant protection against lethal challenge with D39 in comparison to the relative WT control mice (that received PBS rather than the vaccine). In contrast, vaccination of μMT mice with gamma-irradiated *S. pneumoniae* Rx1 (ΔLytA, PdT) showed no evidence of increased protection relative to the respective μMT control mice (that received PBS rather than the vaccine). These results indicate that B-cells are therefore essential for the intranasally administered gamma-irradiated *S. pneumoniae* Rx1 (ΔLytA, PdT) vaccine to induce protective immunity against *Streptococcus pneumoniae*.

Example Nine: Analysis of T-Lymphocyte Responses in Protective Immunity Induced by Intranasal Administration of Gamma-Irradiated *S. pneumoniae* Rx1 (ΔLytA, PdT)

T-lymphocyte responses were assessed following vaccination with gamma-irradiated *S. pneumoniae* Rx1 (ΔLytA, PdT).

Mice were vaccinated intranasally with two doses of gamma-irradiated *S. pneumoniae* Rx1 (ΔLytA, PdT) (12 KGY DI) ($1 \times 10^8$ CFU/dose) and spleens were harvested two weeks after the second vaccination dose. Splenocytes were then stimulated with either the vaccine antigen, MalX protein or Media alone (−control) for 72 hours. Post 72 hours, the supernatants from cell cultures were collected to determine cytokine levels by ELISA (IL-17A and IFN-γ) (FIG. 12A and FIG. 12B).

Intracellular cytokine staining was performed to examine the proportion of Th1 cells (using IFN-γ+), Th2 cells (IL-4+), Th17 cells (IL-17+) and T-reg cells (Foxp3+) following antigen stimulation (FIG. 12C and FIG. 12D).

Vaccination with gamma-irradiated *S. pneumoniae* Rx1 (ΔLytA, PdT) appears to provide no increase in IL-17A or IFN-γ levels in the supernatant following stimulation of splenocytes with the vaccine antigen or MalX as confirmed by ELISA. Similarly, there were no alterations in the proportions of Th1, Th2, Th17 or Tregs as determined by intracellular cytokine staining.

Example Ten: Challenge with Influenza Virus Following Intranasal Administration of Gamma-Irradiated *S. pneumoniae* Rx1 (ΔLytA, PdT)

Analyses were conducted to determine if prior vaccination with gamma-irradiated *S. pneumoniae* Rx1 (ΔLytA, PdT) has any adverse effect on challenge with influenza.

Mice were vaccinated intranasally with two doses of gamma-irradiated *S. pneumoniae* Rx1 (ΔLytA, PdT) (12 KGY DI) ($1 \times 10^8$ CFU/dose). Two weeks after the second vaccination dose, mice were challenged with influenza virus A/PR8 (~100 TCID50) and monitored for weight loss and survival (FIG. 13B). Control mice were given PBS instead of being vaccinated with gamma-irradiated *S. pneumoniae* Rx1 (ΔLytA, PdT) and then challenged with influenza virus A/PR8 (~100 TCID50) and monitored for weight loss and survival (FIG. 13A).

Prior vaccination with gamma-irradiated *S. pneumoniae* Rx1 (ΔLytA, PdT) showed no adverse effects when mice were subsequently challenged with live influenza virus. There is some evidence that prior vaccination with gamma-irradiated *S. pneumoniae* Rx1 (ΔLytA, PdT) offers some protection to influenza challenge, as indicated by all vaccinated mice surviving challenge with influenza strain A/PR8. This suggests some beneficial bystander effects.

Example Eleven: Effect of Cholera Toxin Adjuvant on *S. pneumoniae* Rx1 (ΔLytA, PdT) Efficacy Gamma-irradiated *S. pneumoniae* Rx1 (ΔLytA, PdT) was combined with the prototype adjuvant Cholera Toxin (CT) to assess whether adjuvants can increase the efficacy of the vaccine.

Mice were vaccinated intranasally with two doses of 1 μg CT (as the control) or two doses of gamma-irradiated *S. pneumoniae* Rx1 (ΔLytA, PdT) (12 KGY DI) ($1 \times 10^8$ CFU/dose) plus 1 μg CT.

Two weeks after the second vaccination dose, mice were challenged with $1 \times 10^7$ CFU of *S. pneumoniae* EF3030, with $1 \times 10^6$ CFU of *S. pneumoniae* D39 or with $5 \times 10^6$ CFU of *S. pneumoniae* P9. Following EF3030 infection, seven days later the lungs and nasopharynx were harvested to determine bacterial counts (FIG. 14A and FIG. 14B).

Following D39 or P9 challenge, mice were monitored for survival for 21 days (FIG. 14C and FIG. 14D).

Vaccination with gamma-irradiated *S. pneumoniae* Rx1 (ΔLytA, PdT) with CT adjuvant resulted in significant decreases in bacterial counts in the lungs compared to the non-vaccinated control, post infection with live EF3030. The vaccine with CT afforded significant protection to lethal challenge with live D39 and P9.

To determine the type of immune responses induced by the gamma-irradiated *S. pneumoniae* Rx1 (ΔLytA, PdT) vaccine with cholera toxin as the adjuvant, spleens and serum were harvested two weeks after the second vaccination dose from mice vaccinated intranasally with two doses of gamma-irradiated *S. pneumoniae* Rx1 (ΔLytA, PdT) (12 KGY DI) (1×10$^8$ CFU/dose), with or without the addition of 1 µg CT. Splenocytes were stimulated with either the vaccine antigen, MalX or Media alone (−control) for 72 hours. Post 72 hours, intracellular cytokine staining was performed to look for the proportion of Th1 cells (using IFN-γ+), Th2 cells (IL-4+), Th17 cells (IL-17+) & T-reg cells (Foxp3$^+$) induced after 72 h of stimulation. (FIG. 15A and FIG. 15B). The supernatants from cell cultures were harvested to look for cytokines (IL-17A and IFN-γ) (FIG. 15C and FIG. 15D).

Intranasal vaccination with gamma-irradiated *S. pneumoniae* Rx1 (ΔLytA, PdT) with CT polarised a Th17 response as indicated by an increase in the number of Th17 cells evidenced by intracellular cytokine staining and an increase in IL-17A in the supernatant following stimulation with gamma-irradiated *S. pneumoniae* Rx1 (ΔLytA, PdT) or MalX.

Serum IgA & IgG titres to whole Rx1 (ΔLytA, PdT) cells were determined by ELISA (FIG. 16). Mice immunised with gamma-irradiated *S. pneumoniae* Rx1 (ΔLytA, PdT) in the presence of CT adjuvant showed elevated antibody responses compared to mice immunised with vaccine strain alone.

Example Twelve: Role of Cytokines in Protective Immunity Induced by Intranasally Administered Gamma-Irradiated *S. pneumoniae* Rx1 (ΔLytA, PdT)

The involvement of IFN-γ and IL-7 in vaccine efficacy in immune responses induced by gamma-irradiated *S. pneumoniae* Rx1 (ΔLytA, PdT) was assessed.

Wild-type C57BL/6 mice (WT) were vaccinated intranasally with two doses of gamma-irradiated *S. pneumoniae* Rx1 (ΔLytA, PdT) (1×10$^8$ CFU/dose). Two weeks after the second vaccination dose, mice were injected with 200 µg of neutralising antibodies to IFN-γ or IL-17, or relevant isotype control antibodies at 24 h before challenge, 6 h post challenge and 48 h post challenge (FIGS. 17A and 17B). Mice were challenged intranasally with a lethal dose of *Streptococcus pneumoniae* D39 and survival was monitored for 21 days. Percentage survival is shown.

Administration of either isotype control antibodies did not alter the protective efficacy of the vaccine against D39 challenge. Importantly, vaccination induced significant protection in immunized mice despite IFN-γ neutralisation when compared to their relative control (FIG. 17A). In contrast, this protection was abolished by IL-17A neutralisation (FIG. 17B). These data demonstrate that the mechanisms of protection elicited by gamma-irradiated *S. pneumoniae* Rx1 (ΔLytA, PdT) are IL-17A-dependent and IFN-γ-independent.

Example Thirteen: Gamma-Irradiated *S. pneumoniae* Rx1 (ΔLytA, PdT) Induces Innate IL-17 Responses The source of IL-17 dependent protection was accessed. Wild-type C57BL/6 mice (WT) were vaccinated intranasally with two doses of gamma-irradiated *S. pneumoniae* Rx1 (ΔLytA, PdT) (1×10$^8$ CFU/dose). Two weeks after the second vaccination dose, the mice were challenged with *Streptococcus pneumoniae* D39. 24 and 48 hours post challenge, the lung was harvested and analysed for the proportion of T effector cells (Th1 and Th17), γδ T cells (γδT1 and γδT17) and phagocytic cells (macrophages and neutrophils). Gamma-irradiated *S. pneumoniae* Rx1 (ΔLytA, PdT) vaccination did not alter the total number of T effector cells or the relative populations of Th1 or Th17 cells in the lung 24 hours post D39 challenge (FIG. 18A). Similar results were observed at 48 hours for Total T effector cells and Th17 cells. There was a significant decrease in Th1 cell numbers in immunized mice relative to the PBS-treated controls at 48 hours post challenge. In contrast to T effector cells, intranasal vaccination with the gamma-irradiated *S. pneumoniae* Rx1 (ΔLytA, PdT) induced significant changes in γδ T cell populations in the lung post D39 challenge (FIG. 18A). Whilst the total number of γδ T cells in the lung of vaccinated mice was not significantly different relative to non-immunized mice, the data indicates that immunized mice specifically enhanced γδT17 cell numbers in the lungs at 24 hours which was further enhanced at 48 hours post challenge. There was a decrease in γδT1 cell numbers in vaccinated mice at 24 hours, leading to a significant difference detected at 48 hours relative to the control animals. Overall, these data demonstrate that the gamma-irradiated *S. pneumoniae* Rx1 (ΔLytA, PdT) vaccine promotes a significant increase in γδT17 cell responses associated with a significant decrease in Th1 and γδT1 cells and no difference in the Th17 population. Therefore, the data suggests that γδT17 cells may be a potential innate source of IL-17A involved in mediating protective immunity in vaccinated mice.

The relative numbers of macrophages and neutrophils in the lungs of mice 24 h and 48 h after challenge with *S. pneumoniae* D39 was compared in mice that had been vaccinated with gamma-irradiated *S. pneumoniae* Rx1 (ΔLytA, PdT) or not vaccinated (PBS controls) (FIG. 18B). The numbers of either cell type remained similar at 24 h and 48 h post-challenge in the vaccinated animals, whereas in the PBS control mice there was a significant increase in macrophages in the lungs between 24 h and 48 h post-challenge. This was also apparent for neutrophils.

Example Fourteen: Generation of a Pneumococcal Derivative with a Genetic Alteration in a Gene Encoding a Virulence Determinant

*Streptococcus pneumoniae* strain Rx1 (ΔLytA, PdT) was further genetically modified by removing the gene encoding the pneumococcal surface antigen A (PsaA), as shown in the flow chart of FIG. 25.

PCR, sequencing and Western Blot were performed after each transformation step to confirm successful transformations had occurred and to confirm the generation of Rx1 (ΔLytA, PdT, ΔPsaA) strain (FIG. 19A and FIG. 19B). FIG. 19C confirms the successful deletion of the psaA gene from Rx1 (ΔLytA, PdT) to generate Rx1 (ΔLytA, PdT, ΔPsaA) and demonstrates the growth defect of the Rx1 (ΔLytA, PdT, ΔPsaA) strain in media not supplemented with Mn$^{2+}$.

Western blot, PCR and sequencing thus confirmed the successful generation of *Streptococcus pneumoniae* strain Rx1 (ΔLytA, PdT, ΔPsaA).

Example Fifteen: Secondary Structure Analysis of mRNA Transcript from the ΔpsaA Gene Analyses were performed to predict the secondary structure of the ΔpsaA gene mRNA transcript.

The DNA sequence of the psaA gene of strain Rx1 (ΔLytA, PdT), prior to deletion, including flanking regions, is shown in SEQ ID NO: 4 (FIG. 26). A total of 865 nucleotides were deleted by splice-overlap extension PCR mutagenesis resulting in the deletion of the region from transcription start site through to the sequence beginning GTAAA, 56 nucleotides upstream of the stop codon. The resultant ΔpsaA gene sequence is shown in SEQ ID NO: 5 (FIG. 27A). The mRNA transcript coded by the ΔpsaA gene sequence is shown in SEQ ID NO: 6 (FIG. 27B).

The secondary structure of the mRNA transcript was predicted using RNAfold (RNAfold WebServer ([http://ma.tbi.univie.ac.at/cgi-bin/RNAfold.cgi]) and is shown in FIG. 20. The predicted secondary structure of the mRNA transcript encoded by the ΔpsaA gene shown in FIG. 20 is anticipated to have a minimum free energy of −20.20 kcal/mol.

The psaA coding sequence for pneumococcal surface antigen A (PsaA) is shown in italic/underline with the ATG start codon and TAA stop codon highlighted in bold/italics. The −35 and −10 and sigma70 promoter recognition sequences are shaded in light and dark grey, respectively. The bold G 9 nucleotides upstream of the ATG start codon is the predicted Transcription Start Site (TSS) for the PsaA mRNA. The nucleotides immediately upstream of the ATG start codon and 56 nucleotides upstream of TAA stop codon are squared/bold and constitute the sites for PCR primer annealing.

The coding region of the psaA gene between the primer annealing sites was deleted by splice-overlap extension PCR, such that the squared/bold nucleotide sequences in SEQ ID NO: 4 in psaA are fused together.

Example Sixteen: Effect of Gamma-Irradiation Doses and Conditions on the Viability and Morphology of S. pneumoniae Rx1 (ΔLytA, PdT, ΔPsaA)

The effect of gamma-irradiation on the viability and morphology of concentrated vaccine samples at different irradiation doses.

S. pneumoniae Rx1 (ΔLytA, PdT, ΔPsaA) was cultured in THY broth to obtain a cell density of $10^8$ colony forming units (CFU)/ml. The bacteria were concentrated via centrifugation, washed with PBS, re-centrifuged and resuspended in PBS-10% glycerol at a final concentration of $1 \times 10^{10}$ CFU/ml. The stock S. pneumoniae Rx1 (ΔLytA, PdT, ΔPsaA) ($1 \times 10^{10}$ CFU/ml) was gamma-irradiated at various doses of irradiation (0.5-25 kGy) on dry ice (DI). Post gamma-irradiation samples of the vaccine strain were plated out onto blood agar plates to assess viability and confirm inactivation (FIG. 21A). Scanning electron microscopy of the physical morphology of S. pneumoniae Rx1 (ΔLytA, PdT, ΔPsaA) that had either not been irradiated (FIG. 21B) or irradiated at 25 kGy (FIG. 21C) are shown. Gamma-irradiation did not affect the gross morphology of the bacteria.

The invention claimed is:

1. A vaccine composition comprising photon-irradiated streptococcal bacteria and a pharmaceutically-acceptable excipient, diluent and/or carrier, wherein the streptococcal bacteria are defective in Mn2+ ion transport prior to being photon-irradiated.

2. The vaccine composition of claim 1, wherein:
 the streptococcal bacteria comprise a gene encoding defective PsaA protein; or
 (ii) gene/s encoding PsaA protein is/are absent in the streptococcal bacteria.

3. The vaccine composition of claim 1, wherein the excipient, diluent and/or carrier is a liquid.

4. The vaccine composition of claim 3, wherein the liquid is any one or more of water, oil, liquid paraffin, ethylene glycol, propylene glycol, polyethylene glycol, ethanol, propanol, isopropanol, glycerol, fatty alcohols, triglycerides or mixtures thereof.

5. The vaccine composition of claim 1, wherein the excipient, diluent and/or carrier comprises any one or more of demineralised or distilled water, saline solution, vegetable based oil, silicone oil, mineral oil, soft paraffin or squalane, cellulose derivatives, fatty acid esters, polyvinylpyrridone; agar; carrageenan, gum tragacanth, gum acacia, petroleum jelly, Ringer's solution, isotonic saline, phosphate buffered saline, ethanol and 1,2 propylene glycol.

6. The vaccine composition of claim 1, further comprising a dispersing agent or a suspending agent.

7. The vaccine composition of claim 6, wherein the suspending agent is any one or more of sodium carboxymethylcellulose, methylcellulose, hydroxypropylmethyl-cellulose, poly-vinyl-pyrrolidone, sodium alginate and acetyl alcohol.

8. The vaccine composition of claim 6, wherein the dispersing agent is any one or more of lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate.

9. The vaccine composition of claim 1, wherein the vaccine does not comprise an adjuvant.

10. The vaccine composition of claim 1, wherein the streptococcal bacteria comprise at least one unencapsulated Streptococcal serotype, or at least one unencapsulated Streptococcus pneumoniae serotype.

11. The vaccine composition of claim 1, wherein the streptococcal bacteria are Streptococcus pneumoniae.

12. The vaccine composition of claim 1, wherein:
 (i) the streptococcal bacteria comprise any one or more of a defective autolysin protein, a defective hemolysin protein, and a defective pneumolysin protein; and/or
 (ii) gene/s encoding any one or more of autolysin protein, hemolysin protein, or pneumolysin protein is/are absent in the streptococcal bacteria.

13. The vaccine composition of claim 12, wherein the autolysin is LytA.

14. The vaccine composition of claim 1, wherein the streptococcal bacteria further comprise at least one recombinant DNA portion encoding an antigen or a component thereof that:
 (i) inactivates or attenuates the bacteria; or
 (ii) induces or enhances an immune response in a subject.

15. The vaccine composition of claim 14, wherein the recombinant DNA portion replaces or disrupts an endogenous gene necessary for pathogenicity, infection, reproduction or any combination thereof.

16. The vaccine composition of claim 1, wherein the photon-irradiated streptococcal bacteria comprise whole-attenuated or whole-killed streptococcal bacteria.

17. The vaccine composition according to claim 1, further comprising an adjuvant.

18. The vaccine composition of claim 1, wherein the vaccine composition is formulated for mucosal or intranasal administration or formulated for injection intramuscularly, subcutaneously or intradermally.

19. The vaccine composition of claim 1, wherein the streptococcal bacteria comprise gamma-irradiated mutant streptococcal bacteria and/or gamma-irradiated modified streptococcal bacteria.

20. The vaccine composition of claim 1, wherein the streptococcal bacteria comprise X-irradiated mutant streptococcal bacteria and/or X-irradiated modified streptococcal bacteria.

* * * * *

SEQUENCE LISTING

```
<160> NUMBER OF SEQ ID NOS: 8

<210> SEQ ID NO 1
<211> LENGTH: 1324
<212> TYPE: DNA
<213> ORGANISM: Streptococcus pneumoniae

<400> SEQUENCE: 1
tgaaaatagt taacagact tttgacttct tttatatgat ataataaagt atagtattta      60 tgaaaggac atatagagac tgtaaaaata tacttttgaa aatctttta gtctggggtg     120 ttattgtaga tagaatgcag accttgtcag tcctatttac agtgtcaaaa tagtgcgttt    180
tgaagttcta tctacaagcc taatcgtgac taagattgtc ttctttgtaa ggtagaaata    240
aaggagtttc tggttctgga ttgtaaaaaa tgagttgttt taattgataa ggagtagaat    300
atggaaatta atgtgagtaa attaagaaca gatttgcctc aagtcggcgt gcaaccatat    360
aggcaagtac acgcacactc aactgggaat ccgcattcaa ccgtacagaa tgaagcggat    420
tatcactggc ggaaagaccc agaattaggt tttttctcgc acattgttgg gaacggttgc    480
atcatgcagg taggacctgt tgataatggt gcctgggacg ttgggggcgg ttggaatgct    540
gagacctatg cagcggttga actgattgaa agccattcaa ccaaagaaga gttcatgacg    600
gactaccgcc tttatatcga actcttacgc aatctagcag atgaagcagg tttgccgaaa    660
acgcttgata cagggagttt agctggaatt aaaacgcacg agtattgcac gaataaccaa    720
ccaaacaacc actcagacca cgttgaccct tatccatatc ttgctaaatg gggcattagc    780
cgtgagcagt ttaagcatga tattgagaac ggcttgacga ttgaaacagg ctggcagaag    840
aatgacactg gctactggta cgtacattca gacggctctt atccaaaaga caagtttgag    900
```

```
aaaatcaatg gcacttggta ctactttgac agttcaggct atatgcttgc agaccgctgg      960
aggaagcaca cagacggcaa ctggtactgg ttcgacaact caggcgaaat ggctacaggc     1020
tggaagaaaa tcgctgataa gtggtactat ttcaacgaag aaggtgccat gaagacaggc     1080
tgggtcaagt acaaggacac ttggtactac ttagacgcta agaaggcgc catggtatca      1140 aatgccttta tccagtcagc ggacggaaca ggctggtact acctcaaacc agacggaaca     1200
ctggcagaca agccagaatt cacagtagag ccagatggct tgattacagt aaaataataa     1260
tggaatgtct ttcaaatcag aacagcgcat attattaggt cttgaaaaag cttaatagta     1320
tgcg                                                                  1324

<210> SEQ ID NO 2
<211> LENGTH: 367
<212> TYPE: DNA
<213> ORGANISM: Streptococcus pneumoniae

<400> SEQUENCE: 2
tgaaaatagt ttaacagact tttgacttct tttatatgat ataataaagt atagtattta       60
tgaaaaggac atatagagac tgtaaaaata tactttttgaa atctttttta gtctggggtg     120
ttattgtaga tagaatgcag accttgtcag tcctatttac agtgtcaaaa tagtgcgttt     180
tgaagttcta tctacaagcc taatcgtgac taagattgtc ttctttgtaa ggtagaaata     240
aaggagtttc tggttctgga ttgtaaaaaa tgagttgttt taattgataa ggagtagaat     300
taatggaatg tctttcaaat cagaacagcg catattatta ggtcttgaaa agcttaata      360 gtatgcg                                                              367

<210> SEQ ID NO 3
<211> LENGTH: 234
<212> TYPE: RNA
<213> ORGANISM: Streptococcus pneumoniae

<400> SEQUENCE: 3
aaugcagacc uugucagucc uauuuacagu gucaaaauag ugcguuuuga aguucuaucu       60
acaagccuaa ucgugacuaa gauugucuuc uuuguaaggu agaauaaag gaguuucugg      120 uucuggauug uaaaaaauga guuguuuuaa uugauaagga guagaauuaa uggaaugucu     180
uucaaaucag aacagcgcau auuauuaggu cuugaaaaag cuuaauagua ugcg           234

<210> SEQ ID NO 4
<211> LENGTH: 1140
<212> TYPE: DNA
<213> ORGANISM: Streptococcus pneumoniae

<400> SEQUENCE: 4
cagttttggg actctttatt ggctatagtt ttaatgttgc ggcaggttct agtatcgtgc       60
ttacagctgc tagtttcttt ctcattagct tctttatcgc tcccaaacaa cgatatttga     120
aactgaaaaa taaacatttg ttaaaataag ggcaaagcc taataaatt ggaggatcta       180 atgaaaaaat taggtacatt actcgttctc tttctttctg caatcattct tgtagcatgt     240
gctagcggaa aaaagatac aacttctggt caaaaactaa aagttgttgc tacaaactca      300
atcatcgctg atattactaa aaatattgct ggtgacaaaa ttgaccttca tagtatcgtt     360
ccgattgggc aagacccaca cgaatacgaa ccacttcctg aagacgttaa gaaaacttct     420
gaggctgatt tgattttcta taacggtatc aaccttgaaa caggtggcaa tgcttggttt     480
```

```
acaaaattgg tagaaaatgc caagaaaact gaaaacaaag actacttcgc agtcagcgac      540
ggcgttgatg ttatctacct tgaaggtcaa aatgaaaaag gaaaagaaga cccacacgct      600
tggcttaacc ttgaaaacgg tattattttt gctaaaaata tcgccaaaca attgagcgcc      660
aaagacccta acaataaaga attctatgaa aaaatctca aagaatatac tgataagtta       720
gacaaacttg ataaagaaag taaggataaa tttaataaga tccctgctga aaagaaactc      780
attgtaacca gcgaaggagc attcaaatac ttctctaaag cctatggtgt tccaagtgcc      840
tacatctggg aaatcaatac tgaagaagaa ggaactcctg aacaaatcaa gaccttggtt      900
gaaaaacttc gccaaacaaa agttccatca ctctttgtag aatcaagtgt ggatgaccgt      960
ccaatgaaaa ctgtttctca agacacaaac atcccaatct acgcacaaat ctttactgac     1020
tctatcgcag aacaaggtaa agaaggcgac agctactaca gcatgatgaa atacaacctt     1080
gacaagattg ctgaaggatt ggcaaaataa gcctctgaaa acgtcattc tcatgtgagc      1140
```

<210> SEQ ID NO 5
<211> LENGTH: 281
<212> TYPE: DNA
<213> ORGANISM: Streptococcus pneumoniae

<400> SEQUENCE: 5

```
cagttttggg actctttatt ggctatagtt ttaatgttgc ggcaggttct agtatcgtgc       60
ttacagctgc tagtttctt ctcattagct tctttatcgc tcccaaacaa cgatatttga      120
aactgaaaaa taaacatttg ttaaaataag gggcaaagcc ctaataaatt gggtaaagaa      180
ggcgacagct actacagcat gatgaaatac aaccttgaca agattgctga aggattggca      240
aaataagcct ctgaaaaacg tcattctcat gtgagctggc g                         281
```

<210> SEQ ID NO 6
<211> LENGTH: 110
<212> TYPE: RNA
<213> ORGANISM: Streptococcus pneumoniae

<400> SEQUENCE: 6

```
gguaaagaag gcgacagcua cuacagcaug augaaauaca accuugacaa gauugcugaa       60
ggauuggcaa auaagccuc ugaaaaacgu cauucucaug ugagcuggcg                  110
```

<210> SEQ ID NO 7
<211> LENGTH: 234
<212> TYPE: RNA
<213> ORGANISM: Streptococcus pneumoniae

<400> SEQUENCE: 7

```
gcguaugaua uuucgaaaaa guucuggauu auuauacgcg acaagacuaa acuuucugua       60
agguaauuaa gaugaggaau aguuaauuuu guugaguaaa aaucuuagg ucuuggucuu      120 ugaggaaaua aagauggaau guuucuucug uuagaaucag ugcuaauccg aacaucuauc     180
uugaaguuuu gcgugauaaa acugugacau uuauccugac uguuccagac guaa           234
```

<210> SEQ ID NO 8
<211> LENGTH: 108
<212> TYPE: RNA
<213> ORGANISM: Streptococcus pneumoniae

```
<400> SEQUENCE: 8
gguaaagaag gcgacagcua cuacagcaug augaaauaca accuugacaa gauugcugaa         60
gauggcaaaa uaagccucug aaaaacguca uucucaugug agcuggcg                    108
```